United States Patent
Scheib et al.

(10) Patent No.: US 11,337,770 B2
(45) Date of Patent: *May 24, 2022

(54) STERILE ADAPTER DRIVE DISKS FOR USE IN A ROBOTIC SURGICAL SYSTEM

(71) Applicant: Verb Surgical Inc., Santa Clara, CA (US)

(72) Inventors: Charles J. Scheib, Loveland, OH (US); Jaime Hernandez, San Jose, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 199 days.

This patent is subject to a terminal disclaimer.

(21) Appl. No.: 16/748,425

(22) Filed: Jan. 21, 2020

(65) Prior Publication Data

US 2020/0229885 A1 Jul. 23, 2020

Related U.S. Application Data

(63) Continuation of application No. 15/849,429, filed on Dec. 20, 2017, now Pat. No. 10,582,980.

(Continued)

(51) Int. Cl.
*B32B 3/10* (2006.01)
*A61B 46/10* (2016.01)
(Continued)

(52) U.S. Cl.
CPC ........ *A61B 46/10* (2016.02); *A61B 17/00234* (2013.01); *A61B 34/30* (2016.02); *A61B 34/35* (2016.02); *A61B 34/70* (2016.02); *A61B 46/40* (2016.02); *A61B 90/06* (2016.02); *A61B 90/40* (2016.02); *B25J 15/0466* (2013.01); *B29C 45/0053* (2013.01); *B29C 65/02* (2013.01);
(Continued)

(58) Field of Classification Search
None
See application file for complete search history.

(56) References Cited

U.S. PATENT DOCUMENTS 4,564,270 A 1/1986 Willie
5,255,422 A 10/1993 Russo
(Continued)

FOREIGN PATENT DOCUMENTS

CN 1227476 A 9/1999
CN 102630154 A 8/2012
(Continued)

OTHER PUBLICATIONS

Australian Examination Report of the Australian Patent Office dated Jun. 18, 2019 for related Australian Patent Application No. 2017379816.
(Continued)

*Primary Examiner* — Christopher M Polley
(74) *Attorney, Agent, or Firm* — Womble Bond Dickinson (US) LLP

(57) ABSTRACT

Generally, a sterile adapter for use in robotic surgery may include a frame configured to be interposed between a tool driver and a surgical tool, a plate assembly coupled to the frame, and at least one rotatable coupler supported by the plate assembly and configured to communicate torque from an output drive of the tool driver to an input drive of the surgical tool.

20 Claims, 34 Drawing Sheets

Related U.S. Application Data

(60) Provisional application No. 62/436,981, filed on Dec. 20, 2016, provisional application No. 62/436,965, filed on Dec. 20, 2016, provisional application No. 62/436,957, filed on Dec. 20, 2016, provisional application No. 62/436,974, filed on Dec. 20, 2016.

(51) Int. Cl.
*A61B 90/00* (2016.01)
*B25J 15/04* (2006.01)
*A61B 34/35* (2016.01)
*A61B 34/30* (2016.01)
*A61B 34/00* (2016.01)
*A61B 90/40* (2016.01)
*A61B 17/00* (2006.01)
*A61B 46/00* (2016.01)
*B29C 45/00* (2006.01)
*B29C 65/02* (2006.01)
*G01V 8/16* (2006.01)
*B29L 31/00* (2006.01)

(52) U.S. Cl.
CPC .............. *A61B 34/25* (2016.02); *A61B 34/74* (2016.02); *A61B 34/76* (2016.02); *A61B 90/361* (2016.02); *A61B 2017/00115* (2013.01); *A61B 2017/00199* (2013.01); *A61B 2017/00203* (2013.01); *A61B 2017/00207* (2013.01); *A61B 2017/00216* (2013.01); *A61B 2017/00221* (2013.01); *A61B 2017/00477* (2013.01); *A61B 2017/00486* (2013.01); *A61B 2017/00876* (2013.01); *A61B 2034/302* (2016.02); *A61B 2034/742* (2016.02); *A61B 2034/743* (2016.02); *A61B 2034/744* (2016.02); *A61B 2090/0811* (2016.02); *A61B 2090/0812* (2016.02); *A61B 2090/0813* (2016.02); *B29L 2031/7546* (2013.01); *G01V 8/16* (2013.01); *Y10S 901/41* (2013.01); *Y10S 901/46* (2013.01); *Y10S 901/47* (2013.01); *Y10S 901/49* (2013.01)

(56) References Cited

U.S. PATENT DOCUMENTS

| | | | |
|---|---|---|---|
| 6,331,181 | B1 | 12/2001 | Tierney et al. |
| 7,048,745 | B2 | 5/2006 | Tierney et al. |
| 9,478,882 | B1 | 10/2016 | Schmidt et al. |
| 9,687,312 | B2 | 6/2017 | Dachs et al. |
| 2002/0032451 | A1 | 3/2002 | Tiernet et al. |
| 2002/0032452 | A1 | 3/2002 | Tierney et al. |
| 2004/0049205 | A1 | 3/2004 | Lee et al. |
| 2004/0172011 | A1 | 9/2004 | Jordan et al. |
| 2006/0191138 | A1 | 8/2006 | Takashima et al. |
| 2007/0137372 | A1 | 6/2007 | Devegenzo et al. |
| 2007/0142824 | A1 | 6/2007 | Devengenzo et al. |
| 2007/0151390 | A1 | 7/2007 | Blumenkranz et al. |
| 2008/0103491 | A1 | 5/2008 | Omori et al. |
| 2008/0119870 | A1 | 5/2008 | Williams |
| 2008/0140088 | A1 | 6/2008 | Orban, III |
| 2008/0177284 | A1 | 7/2008 | Lee et al. |
| 2009/0024145 | A1 | 1/2009 | Meade et al. |
| 2009/0248039 | A1* | 10/2009 | Cooper .................. A61B 34/30 606/130 |
| 2010/0170519 | A1 | 7/2010 | Romo et al. |
| 2010/0331858 | A1 | 12/2010 | Simaan et al. |
| 2011/0124035 | A1 | 5/2011 | Broadley et al. |
| 2012/0132450 | A1 | 5/2012 | Timm et al. |
| 2012/0209291 | A1 | 8/2012 | Anderson et al. |
| 2012/0230060 | A1 | 9/2012 | Tanaka et al. |
| 2012/0239060 | A1 | 9/2012 | Orbann |
| 2012/0253330 | A1 | 10/2012 | Ries |
| 2013/0310866 | A1 | 11/2013 | Belagali |
| 2013/0345732 | A1 | 12/2013 | Dannaher et al. |
| 2014/0001231 | A1 | 1/2014 | Shelton et al. |
| 2014/0128886 | A1 | 5/2014 | Holop et al. |
| 2014/0148808 | A1 | 5/2014 | Inkpen et al. |
| 2015/0202009 | A1 | 7/2015 | Nussbaumer et al. |
| 2015/0230871 | A1 | 8/2015 | Sayler et al. |
| 2015/0245873 | A1 | 9/2015 | Hong et al. |
| 2015/0257841 | A1 | 9/2015 | Dachs, II |
| 2015/0305815 | A1 | 10/2015 | Holop et al. |
| 2016/0000449 | A1 | 1/2016 | Aman et al. |
| 2016/0058513 | A1 | 3/2016 | Giorgi |
| 2016/0121143 | A1 | 5/2016 | Mumaw et al. |
| 2016/0206391 | A1 | 7/2016 | Deodhar |
| 2016/0317759 | A1 | 11/2016 | Lorberbaum et al. |
| 2016/0361049 | A1 | 12/2016 | Dachs et al. |
| 2016/0361127 | A1 | 12/2016 | Dachs et al. |
| 2016/0361131 | A1 | 12/2016 | Dachs, II et al. |
| 2017/0082806 | A1 | 3/2017 | Van et al. |
| 2018/0078034 | A1 | 3/2018 | Savall et al. |
| 2018/0116737 | A1 | 5/2018 | Bajo et al. |
| 2018/0168752 | A1 | 6/2018 | Scheib et al. |
| 2018/0168761 | A1 | 6/2018 | Vargas et al. |
| 2018/0168762 | A1 | 6/2018 | Scheib et al. |
| 2018/0168763 | A1 | 6/2018 | Scheib et al. |
| 2018/0200021 | A1 | 7/2018 | Scheib et al. |
| 2018/0206931 | A1 | 7/2018 | Scheib |

FOREIGN PATENT DOCUMENTS

| | | |
|---|---|---|
| CN | 103533908 A | 1/2014 |
| CN | 103619279 A | 3/2014 |
| CN | 104582625 A | 4/2015 |
| CN | 105611892 A | 5/2016 |
| CN | 106164726 A | 11/2016 |
| JP | 60-036043 | 2/1985 |
| JP | 2007-167643 A | 7/2007 |
| JP | 2009-524491 | 7/2009 |
| JP | 2011-516120 A | 5/2011 |
| JP | 2014-004483 | 1/2014 |
| JP | 2014-512876 A | 5/2014 |
| JP | 2017-512528 A | 5/2017 |
| JP | 2017-512561 A | 5/2017 |
| KR | 10-2016-0132904 A | 11/2016 |
| WO | 2011/037394 A2 | 3/2011 |
| WO | 2015/023834 A1 | 2/2015 |
| WO | 2015/142792 A1 | 9/2015 |
| WO | 2015/150149 A1 | 10/2015 |

OTHER PUBLICATIONS

Communication pursuant to Rules 70(2) and 70a(2) EPC of the European Patent Office dated Jun. 3, 2020 for related European Patent Application No. 17885280.2.
Examination Report of the Australian Patent Office dated Jun. 30, 2020 for related Australian Patent Application No. 2020200350.
Examiner's Report of the Canadian Patent Office dated Jun. 15, 2020 for Canadian Patent Application No. 3,043,933.
Extended European Search Report of the European Patent Office dated May 12, 2020 for related European Patent Application No. 17885280.2.
Final Office Action of the US Patent Office dated Mar. 23, 2020 for related U.S. Appl. No. 15/849,419.
First Office Action of the Chinese Patent Office dated May 7, 2020 for related Chinese Patent Application No. 201780004183.6.
International Search Report of the PCT Patent Office dated May 8, 2018 for PCT Patent Application No. PCT/US2017/067320.
Non Final Office Action of the US Patent Office dated Dec. 11, 2019 for related U.S. Appl. No. 15/847,518.
Non Final Office Action of the US Patent Office dated Nov. 29, 2019 for related U.S. Appl. No. 15/849,450.
Notice of Allowance of the US Patent Offfice dated Mar. 10, 2020 for related U.S. Appl. No. 15/849,450.
Notice of Reasons for Refusal of the Japanese Patent Office dated May 20, 2020 for related Japanese Patent Application No. 2019-529616.

(56) References Cited

OTHER PUBLICATIONS

Notice of Reasons for Refusal of the Japanese Patent Office dated May 27, 2020 for related Japanese Patent Application No. 2019-529255.
Notification of Transmittal or Search Report and Written Opinion of the PCT Patent Office dated May 8, 2018 for PCT Patent Application No. PCT/US2017/067320.
Partial Supplementary European Search Report of the European Patent Office dated Jun. 15, 2020 for related European Patent Application No. 17885373.5.
Search Report of the Chinese Patent Office dated Apr. 23, 2020 for related Chinese Patent Application No. 201780004183.6.
Search Report of the Japanese Patent Office dated Apr. 1, 2020 for related Japanese Patent Application No. 2019-529616.
U.S. Patent Application filed on Dec. 19, 2017, by Scheib et al., U.S. Appl. No. 15/847,518.
U.S. Patent Application filed on Dec. 19, 2017, by Scheib et al., U.S. Appl. No. 15/847,562.
U.S. Patent Application filed on Dec. 19, 2017, by Scheib et al., U.S. Appl. No. 15/847,638.
U.S. Patent Application filed on Dec. 20, 2017, by Scheib et al., U.S. Appl. No. 15/849,419.
U.S. Patent Application filed on Dec. 20, 2017, by Scheib et al., U.S. Appl. No. 15/849,429.
U.S. Patent Application filed on Dec. 20, 2017, by Scheib et al., U.S. Appl. No. 15/849,443.
U.S. Patent Application filed on Dec. 20, 2017, by Scheib et al., U.S. Appl. No. 15/849,450.
Written Opinion of the PCT Patent Office dated May 8, 2018 for related PCT Patent Application No. PCT/US2017/067320.
Australian Examination Report dated Nov. 21, 2020, for related Australian Appln. No. 2020203096 4 Pages.
PCT Search Report and Written Opinion dated Mar. 6, 2018, for related PCT Appln. No. PCT/US2017/067706 18 Pages.
Australian Examination Report dated Jun. 18, 2019, for related Australian Appln. No. 2017379917 4 Pages.
International Preliminary Report on Patentability dated Jun. 25, 2019, for related PCT Appln. No. PCT/US2017/067706 16 Pages.
Advisory Action of the U.S. Patent Office dated Jun. 2, 2020 for related U.S. Appl. No. 15/847,562.
Advisory Action of the U.S. Patent Office dated Jun. 4, 2020 for related U.S. Appl. No. 15/849,419.
Advisory Action of the U.S. Patent Office dated May 8, 2020 for related U.S. Appl. No. 15/849,443.
Decision of Refusal of the Japanese Patent Office dated Dec. 8, 2020 for related Japanese Patent Application No. 2019-529255.
Decision to Grant a Patent of the Japanese Patent Office dated Dec. 28, 2020 for related Japanese Patent Application No. 2019-529616.
Examiner's Report of the Canadian Patent Office dated Jun. 12, 2020 for related Canadian Patent Application No. 3043788.
Final Office Action of the U.S. Patent Office dated Feb. 26, 2020 for related U.S. Appl. No. 15/849,443.
Final Office Action of the U.S. Patent Office dated Feb. 28, 2020 for related U.S. Appl. No. 15/847,562.
Non-Final Office Action of the U.S. Patent Office dated Aug. 15, 2019 for related U.S. Appl. No. 15/847,638.
Non-Final Office Action of the U.S. Patent Office dated Aug. 22, 2019 for related U.S. Appl. No. 15/849,429.
Non-Final Office Action of the U.S. Patent Office dated Jul. 15, 2020 for related U.S. Appl. No. 15/849,443.
Non-Final Office Action of the U.S. Patent Office dated Nov. 7, 2019 for related U.S. Appl. No. 15/847,562.
Non-Final Office Action of the U.S. Patent Office dated Oct. 17, 2019 for related U.S. Appl. No. 15/849,419.
Non-Final Office Action of the U.S. Patent Office dated Oct. 30, 2019 for related U.S. Appl. No. 15/849,443.
U.S. Appl. No. 62/432,538, filed Dec. 9, 2016.
Notice of Allowance of the U.S. Patent Office dated Dec. 11, 2020 for related U.S. Appl. No. 15/849,443.
Notice of Allowance of the U.S. Patent Office dated Dec. 19, 2019 for related U.S. Appl. No. 15/847,638.
Notice of Allowance of the U.S. Patent Office dated Dec. 28, 2020 for related U.S. Appl. No. 15/847,562.
Notice of Allowance of the U.S. Patent Office dated Jun. 25, 2020 for related U.S. Appl. No. 15/847,518.
Notice of Allowance of the U.S. Patent Office dated Mar. 25, 2020 for related U.S. Appl. No. 15/847,638.
Notice of Allowance of the U.S. Patent Office dated Nov. 27, 2020 for related U.S. Appl. No. 15/847,562.
Notice of Allowance of the U.S. Patent Office dated Oct. 1, 2020 for related U.S. Appl. No. 15/849,419.
Notice of Allowance of the U.S. Patent Office dated Oct. 23, 2019 for related U.S. Appl. No. 15/849,429.
Notice of Allowance of the U.S. Patent Office dated Sep. 23, 2020 for related U.S. Appl. No. 15/847,562.
Notification of Reason for Refusal of the Korean Patent Office dated Oct. 30, 2020 for related Korean Patent Application No. 10-2019-7017032.
Notification of Reason for Refusal of the Korean Patent Office dated Oct. 30, 2020 for related Korean Patent Application No. 10-2019-7017038.
First Office Action of the Chinese Patent Office dated Feb. 19, 2021 for related Chinese Patent Application No. 201780004172.8.
Search Report of the Chinese Patent Office dated Jan. 26, 2021 for related Chinese Patent Application No. 201780004183.6.
Second Office Action of the Chinese Patent Office dated Feb. 2, 2021 for related Chinese Patent Application No. 201780004183.6.
Notification of Reasons for Refusal for Japanese Application No. 2021-009014 dated Sep. 14, 2021, 7 pages.
Notice of Preliminary Rejection for Korean Application No. 10-2021-7022776 dated Oct. 22, 2021, 8 pages.
Examination Report for Australian Application No. 2020203096 dated Feb. 12, 2021, 4 pages.
Office Action for Chinese Application No. 2017800041728 dated Oct. 27, 2021, 4 pages.
Preliminary Office Action for Brazilian Application No. BR112019010317-1 dated Feb. 15, 2022, 5 pages.
Preliminary Office Action for Brazilian Application No. BR112019010623.5 dated Feb. 15, 2022, 5 pages.
Notification of Reasons for Rejection for Japanese Application No. 2021-065429 dated Mar. 15, 2022, 12 pages.

\* cited by examiner

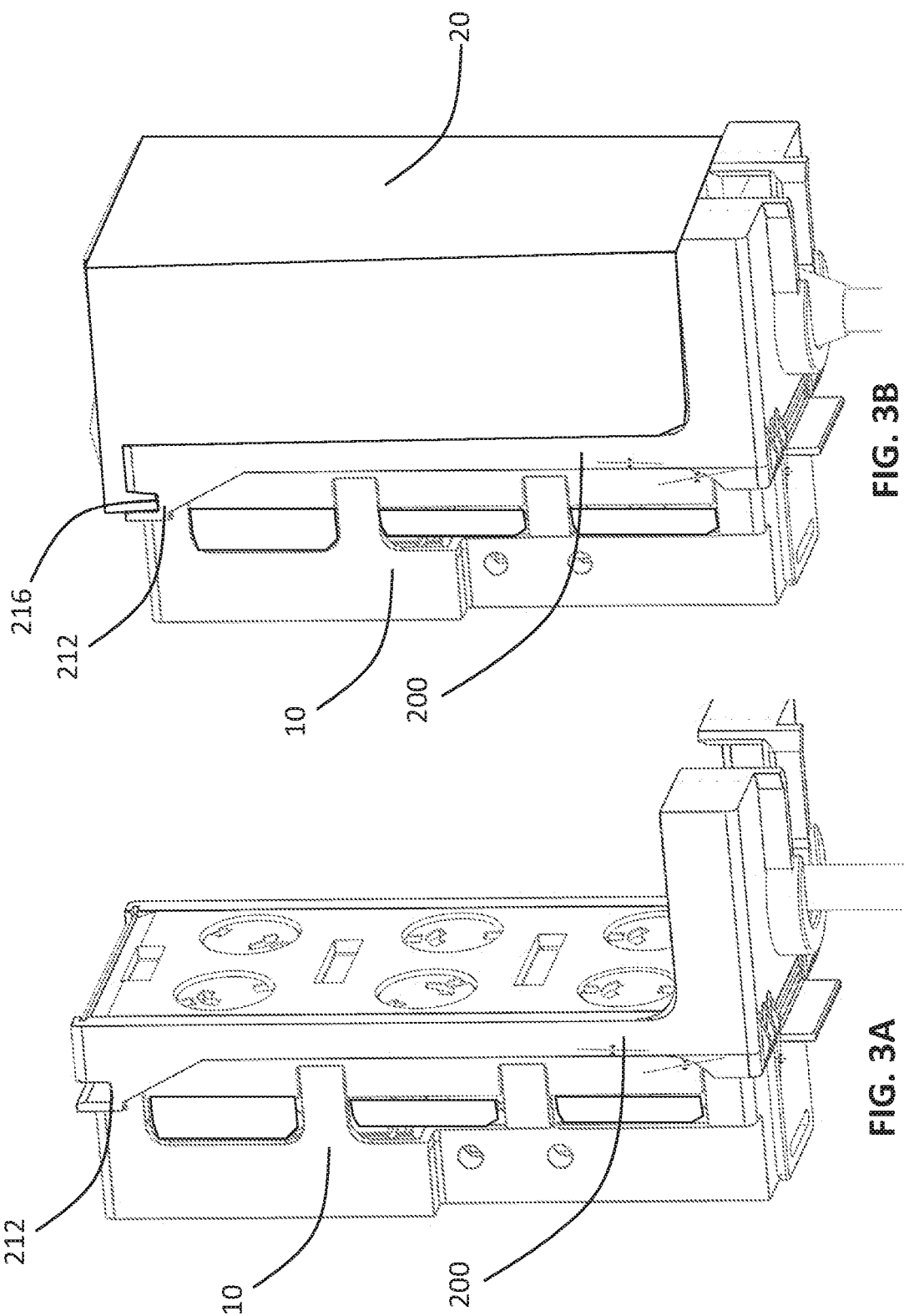

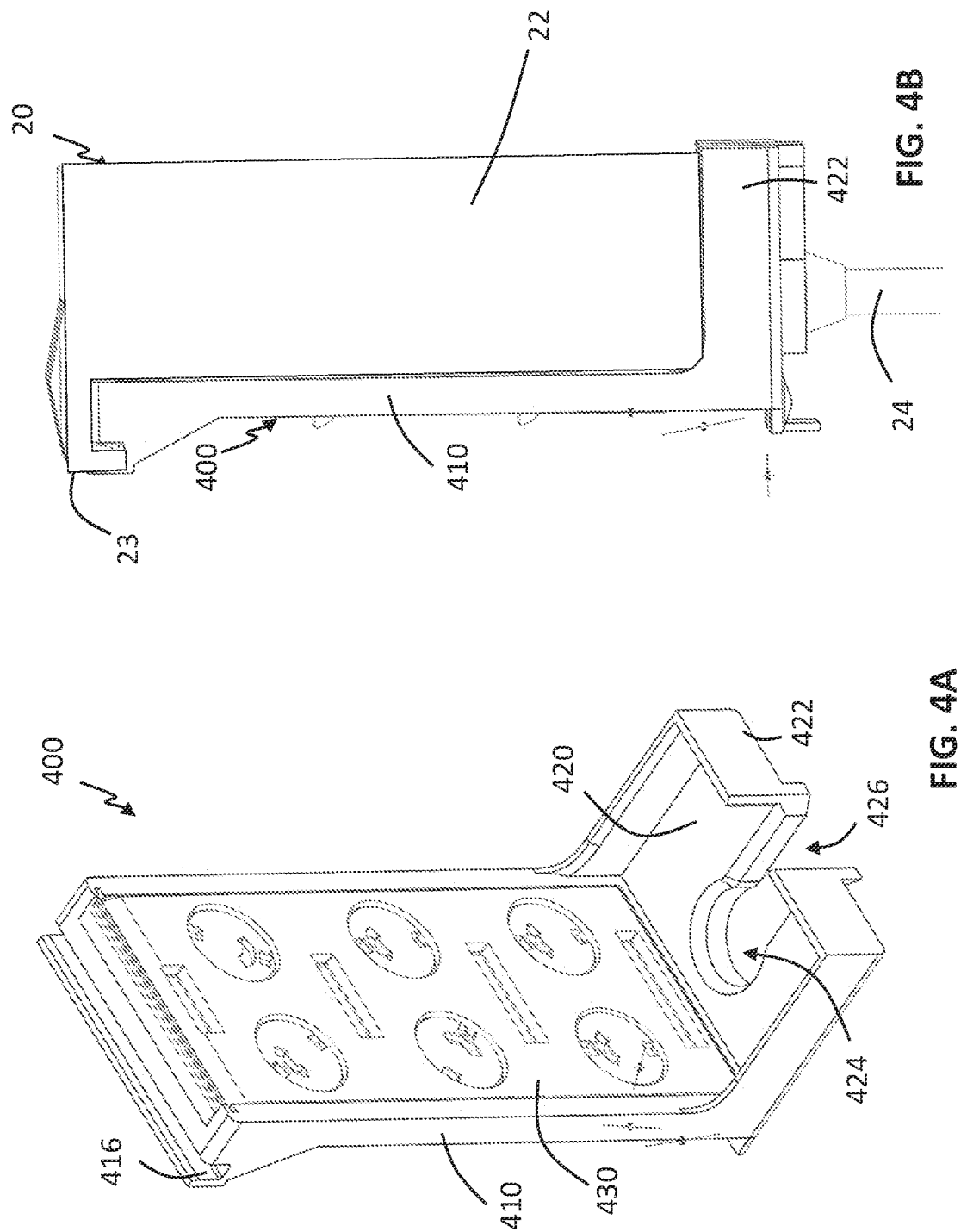

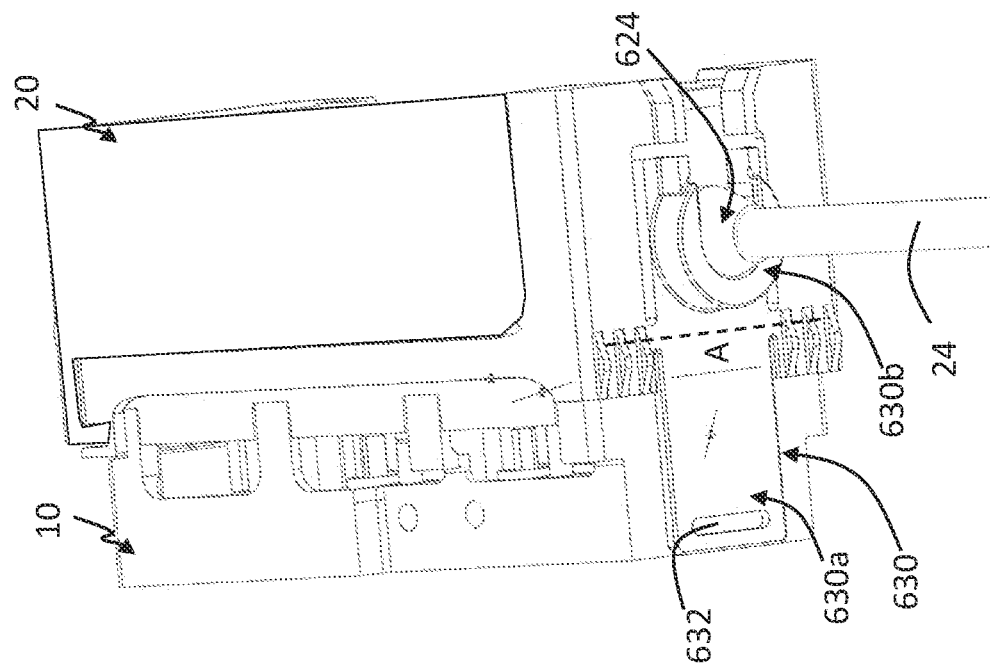
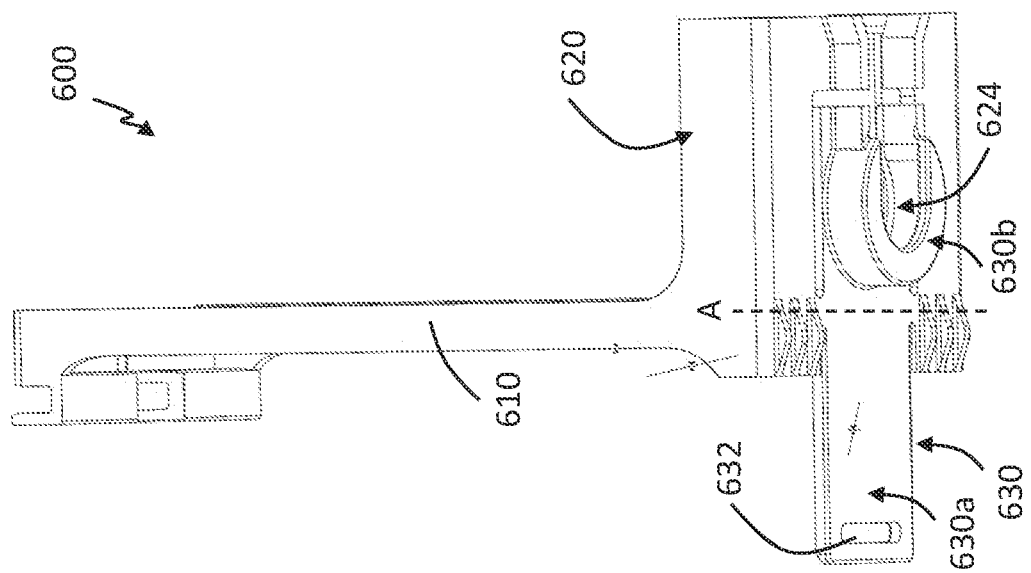

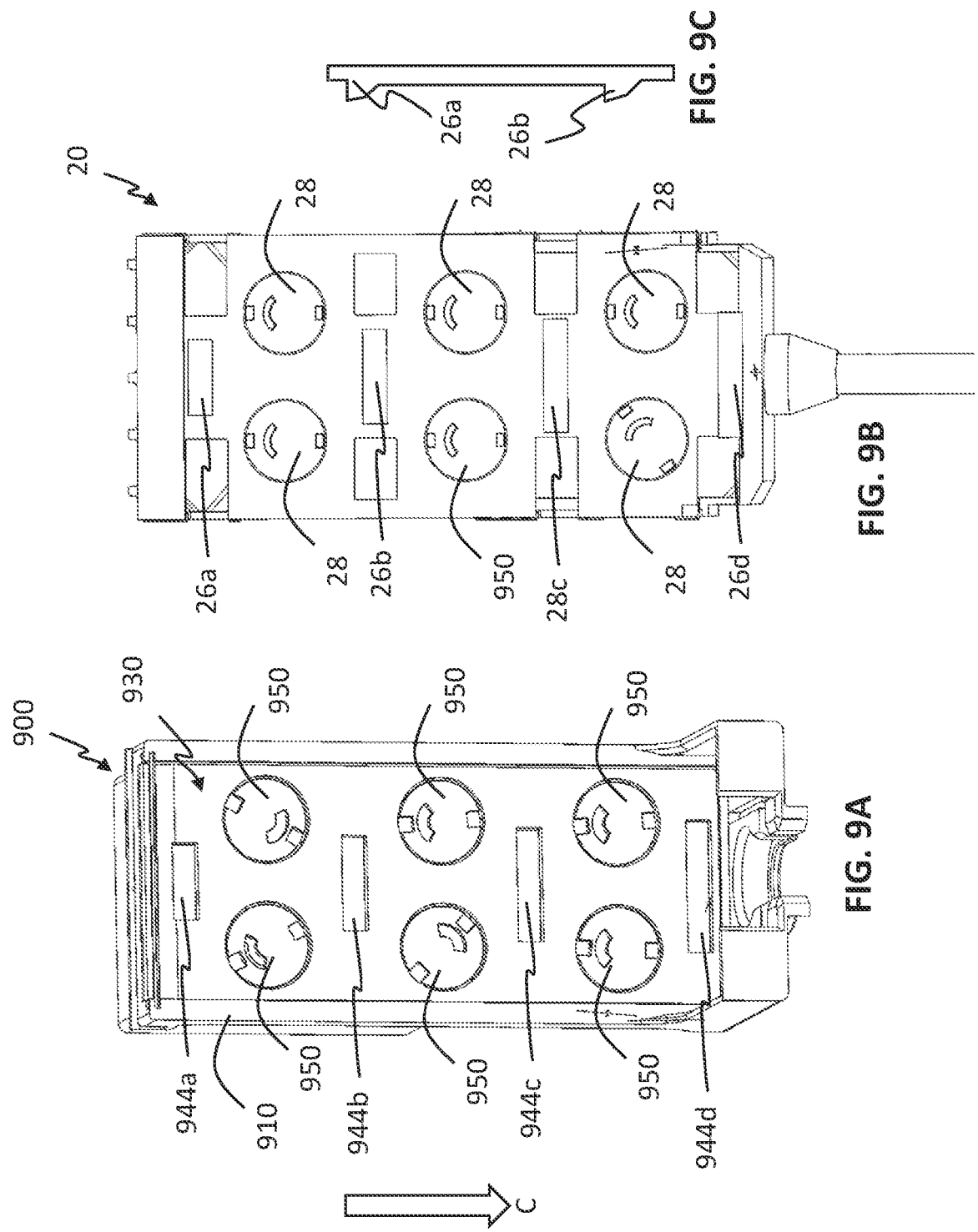

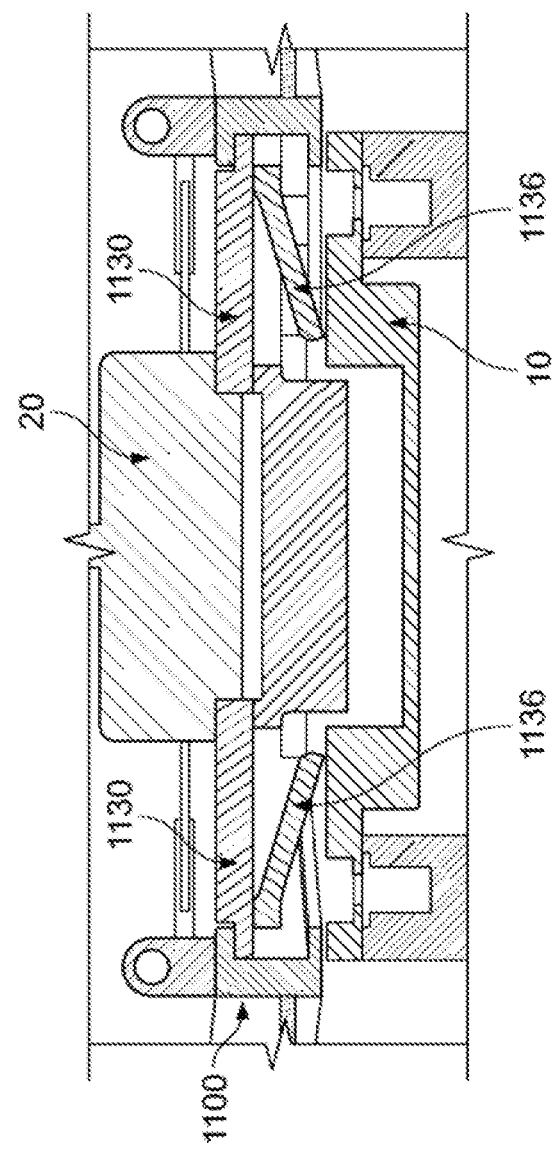

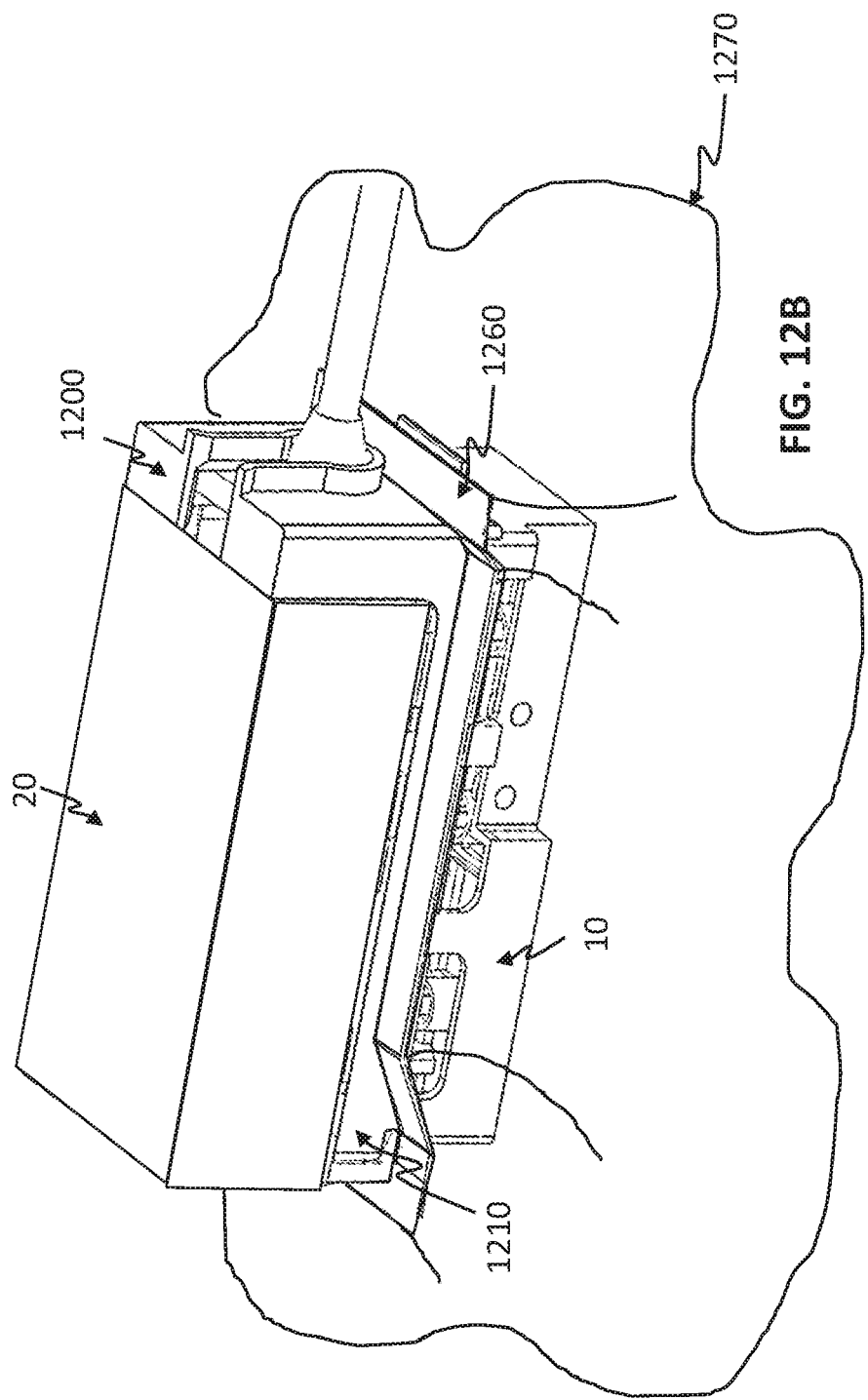

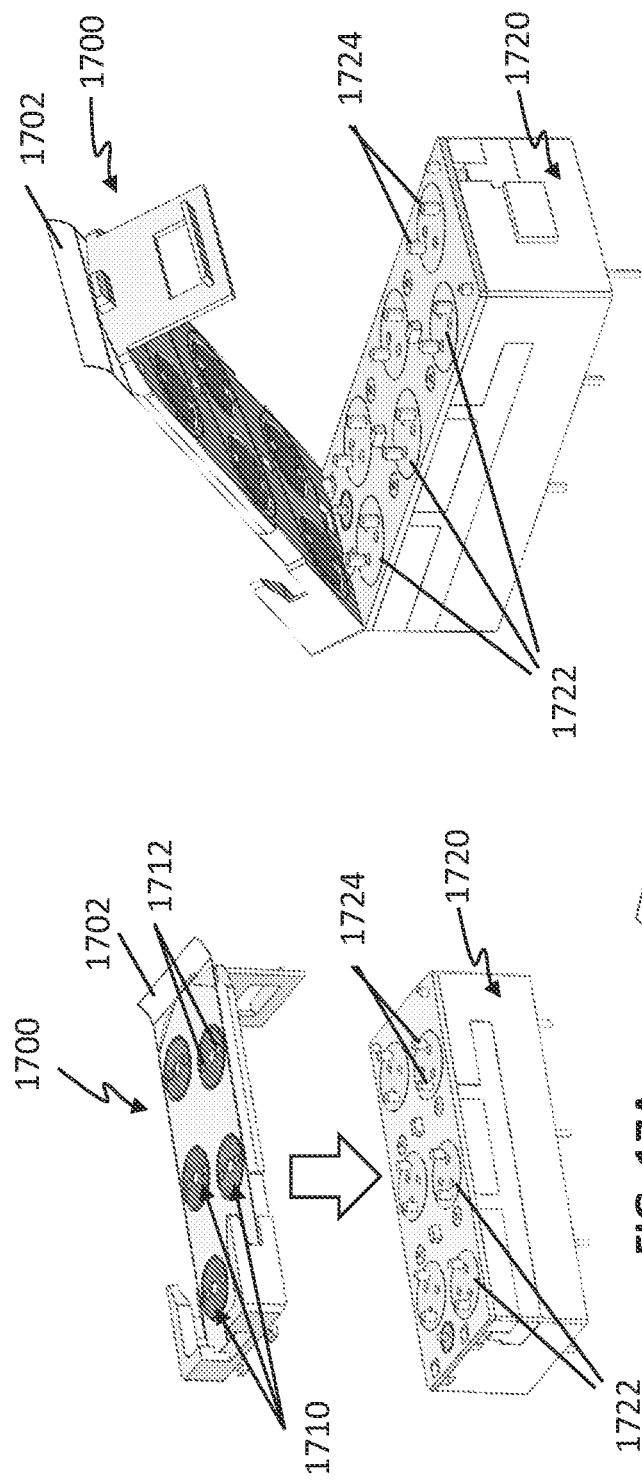
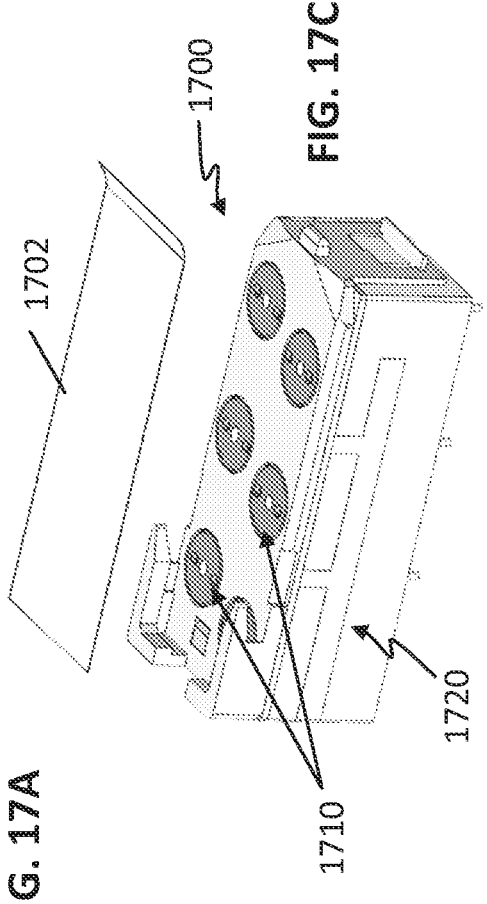
FIG. 17A
FIG. 17B
FIG. 17C

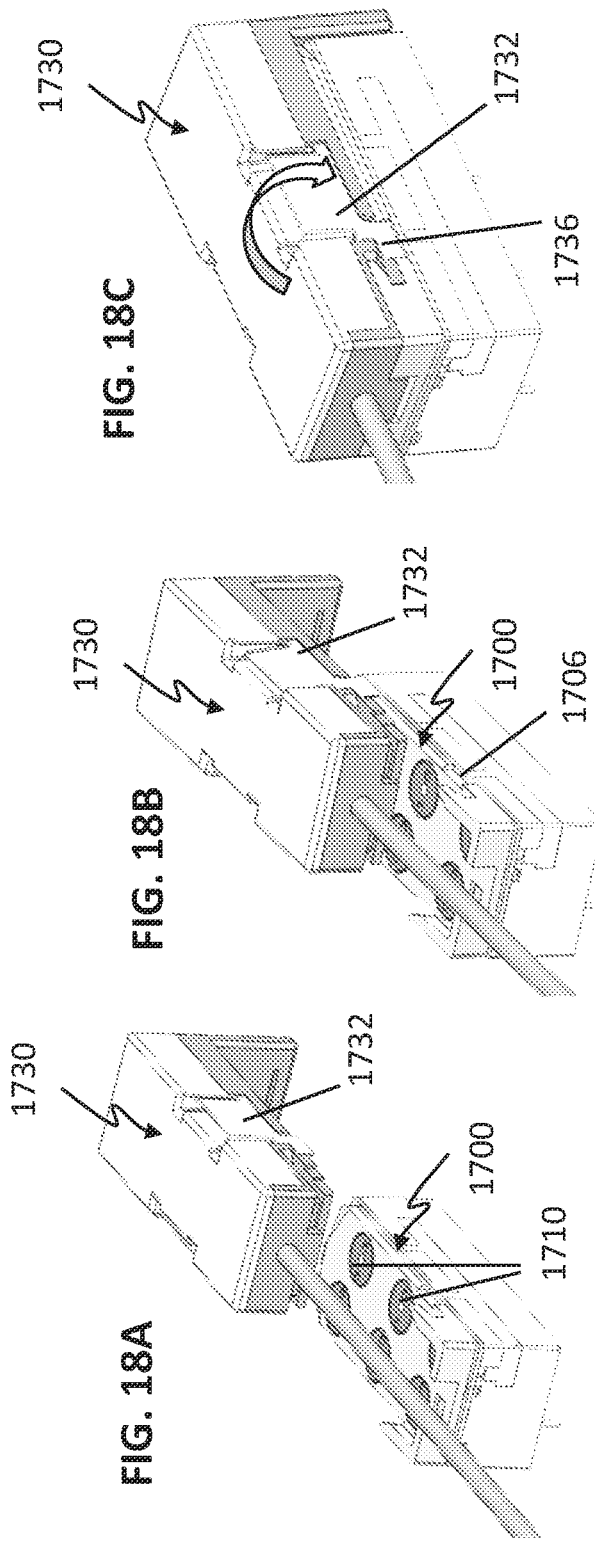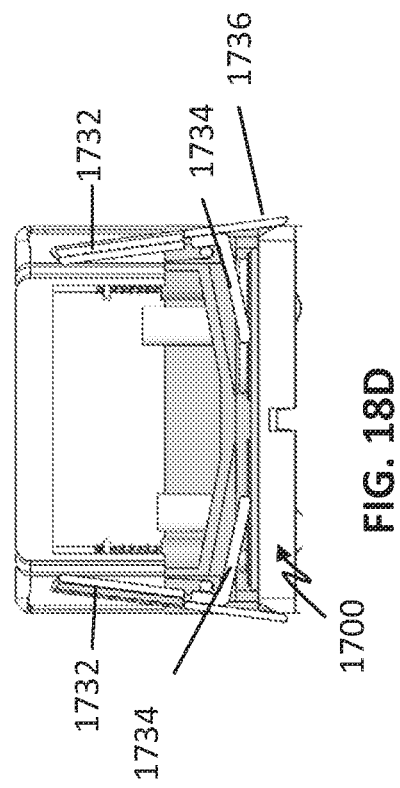

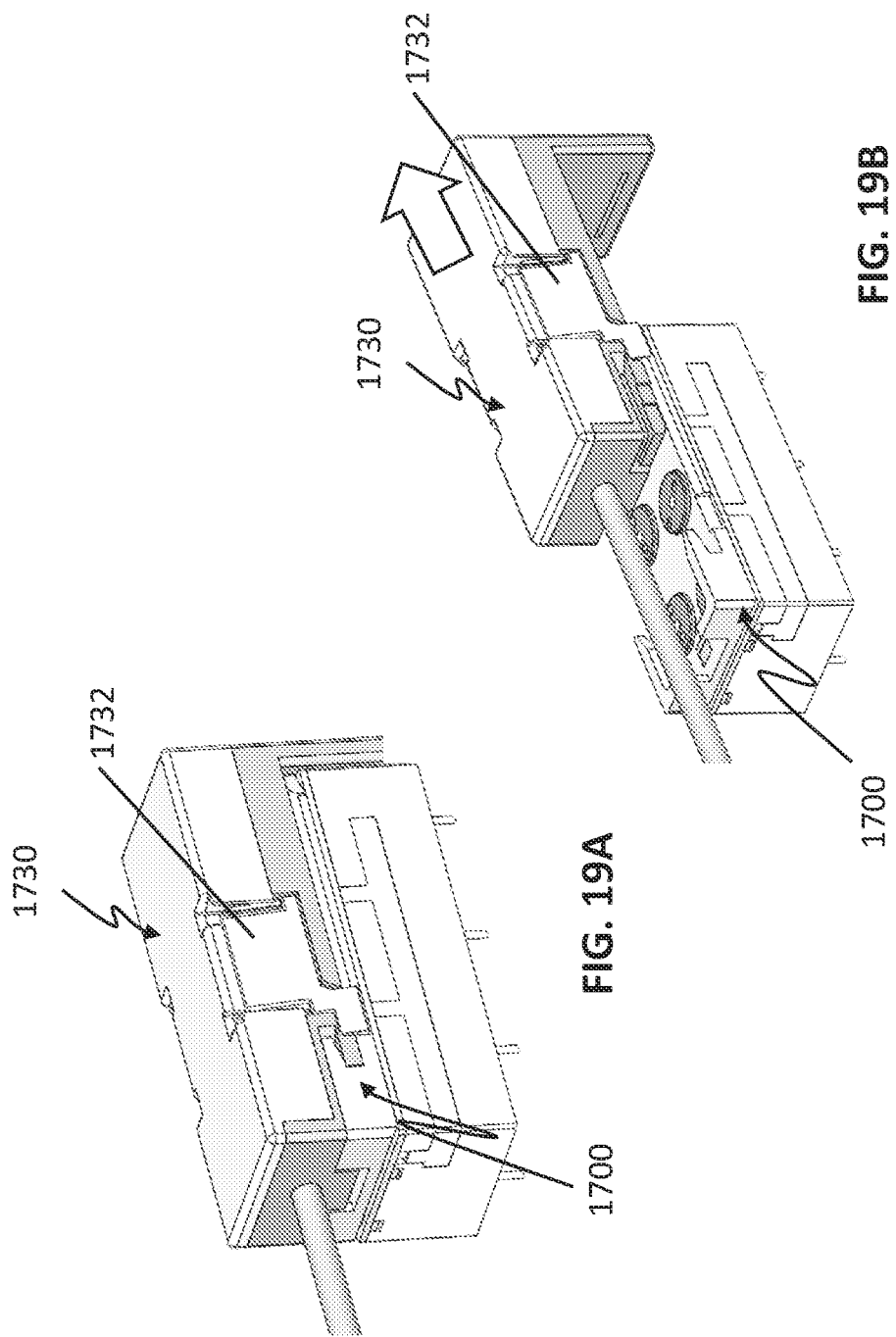

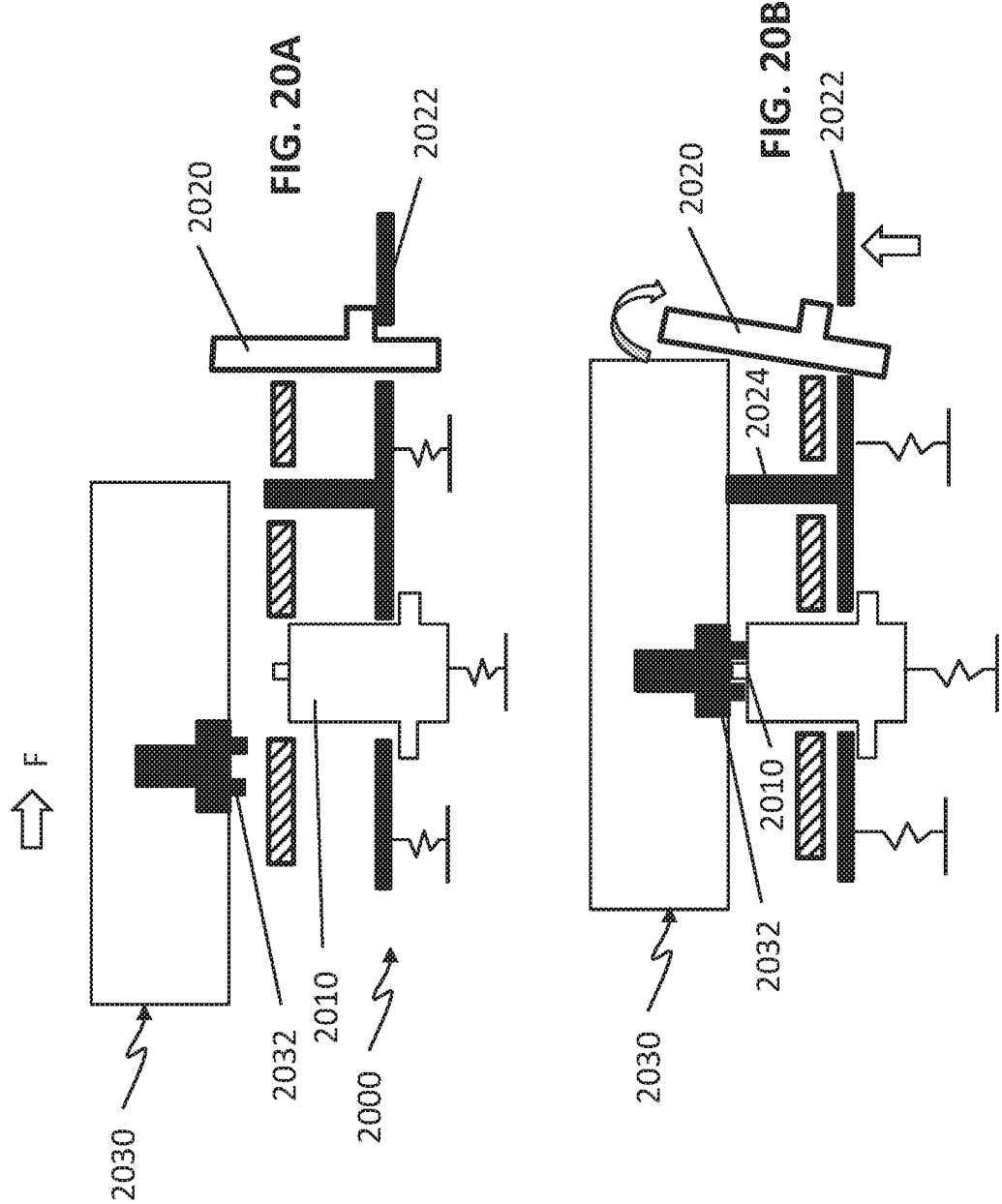

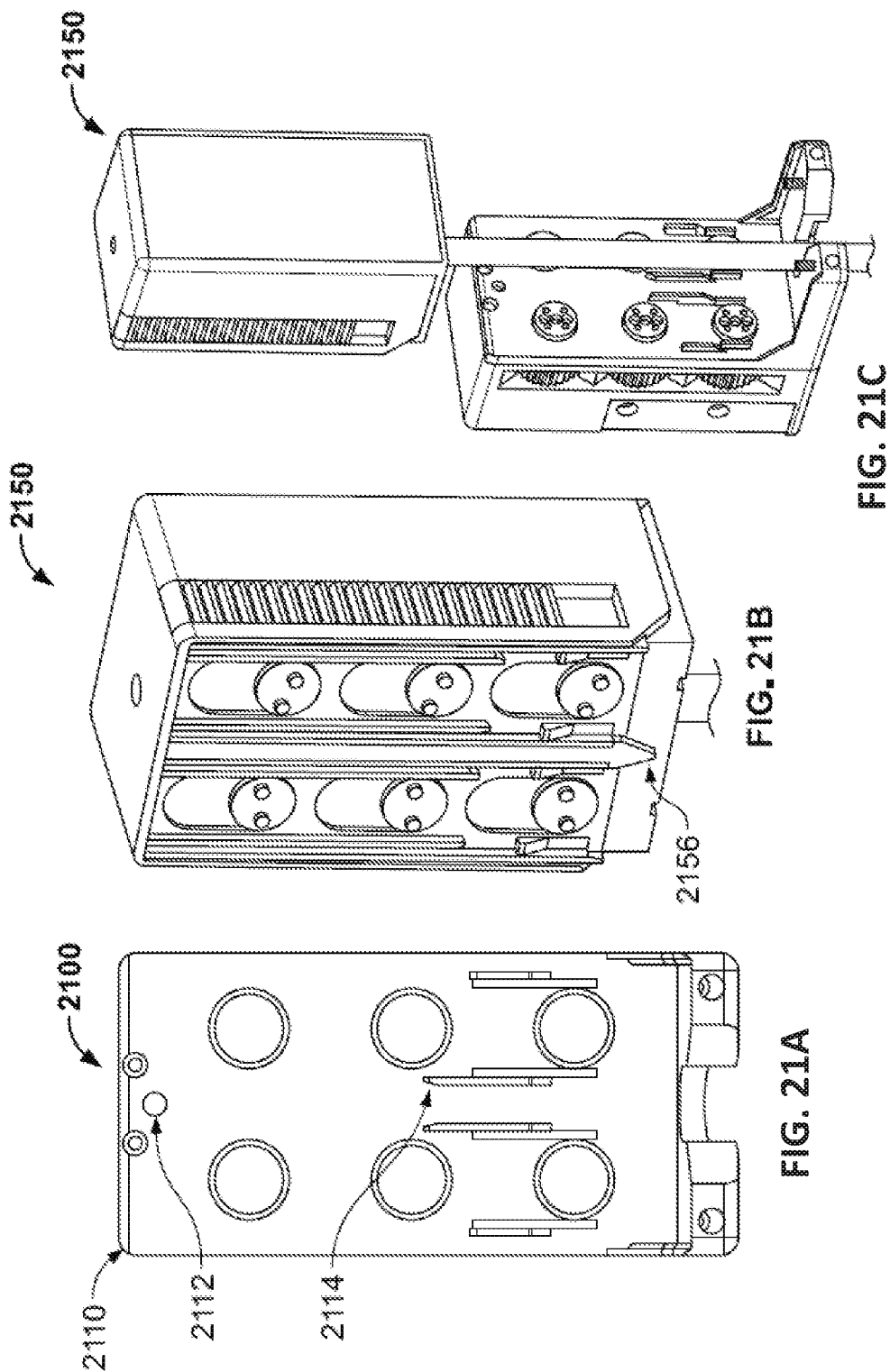

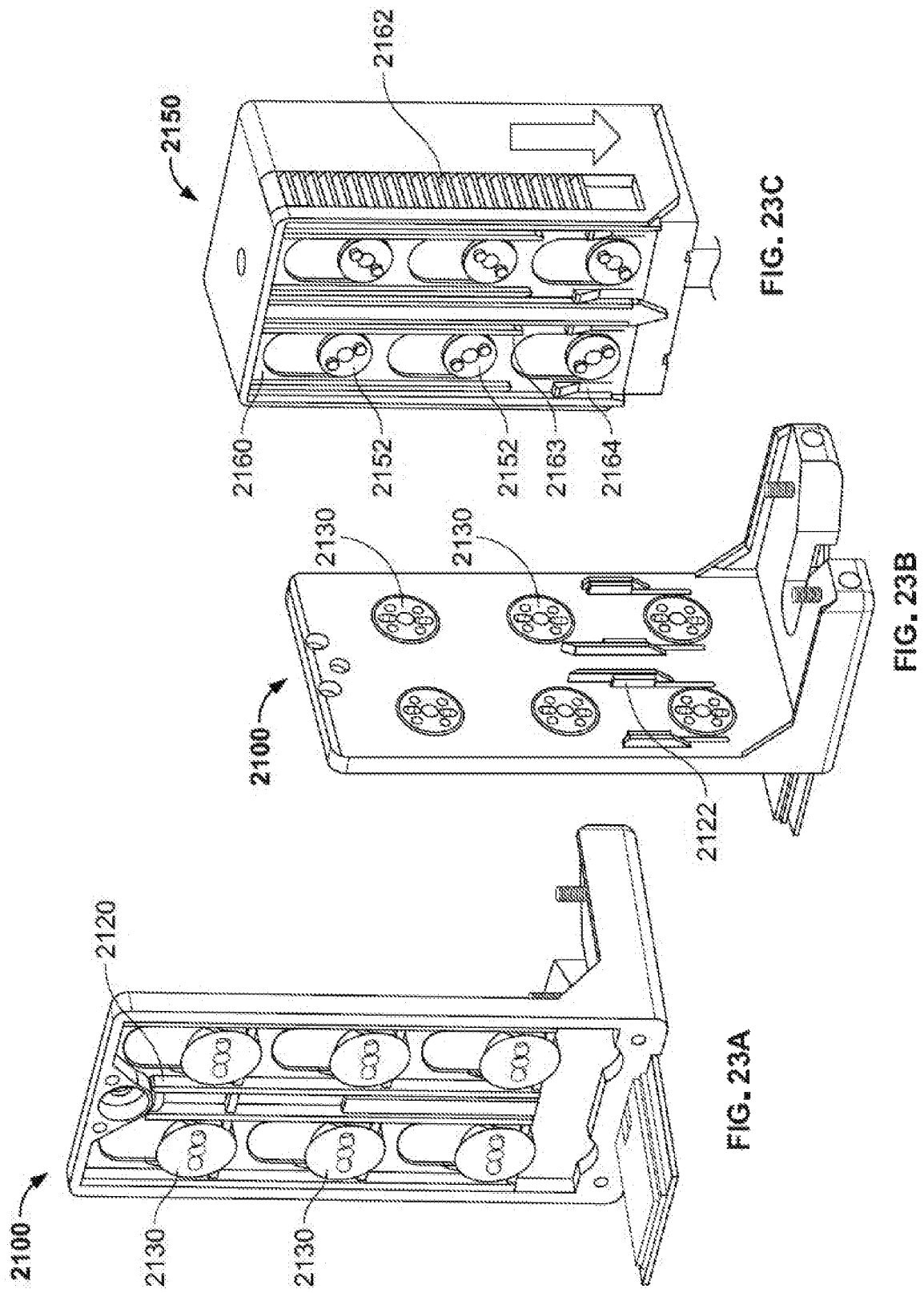

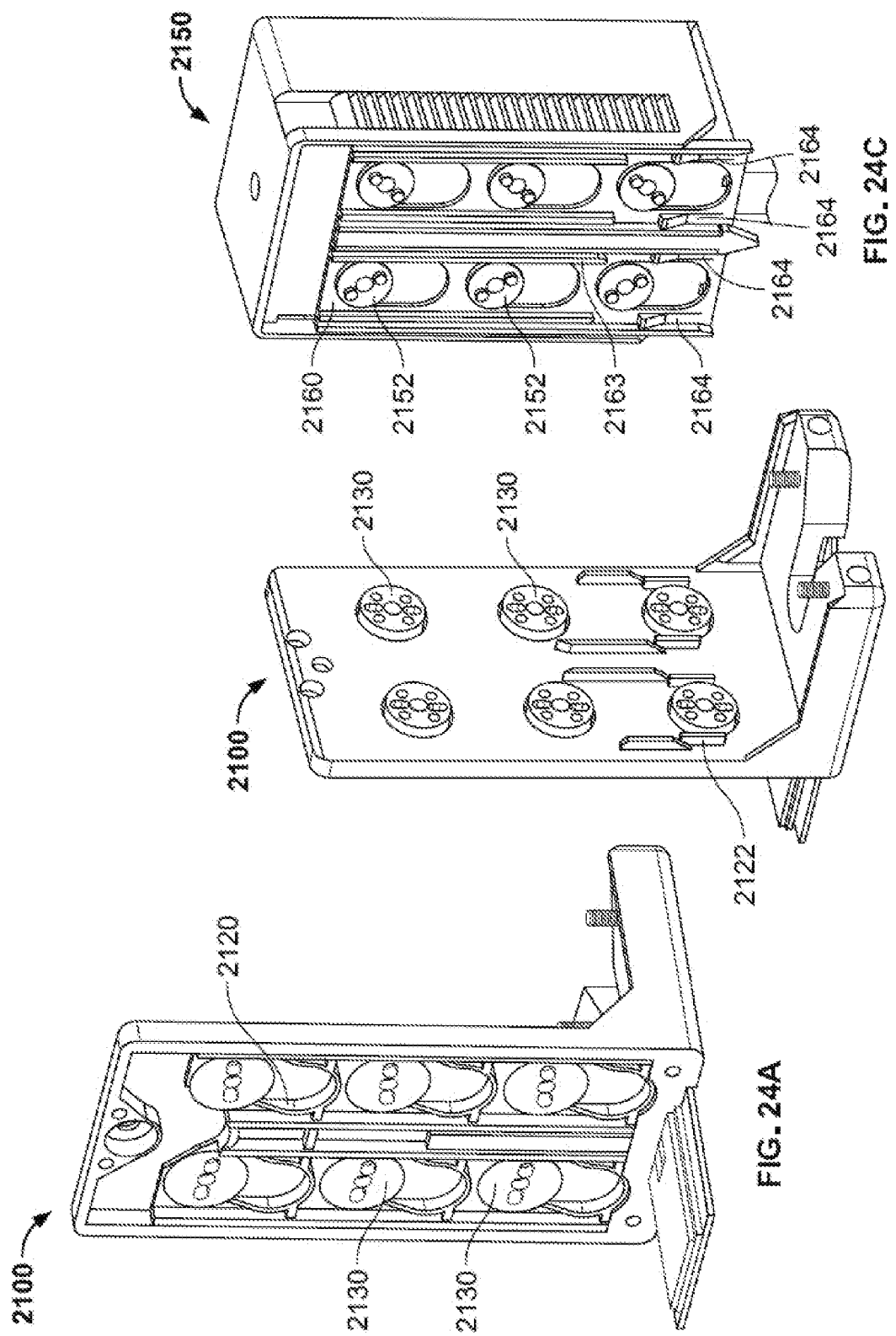

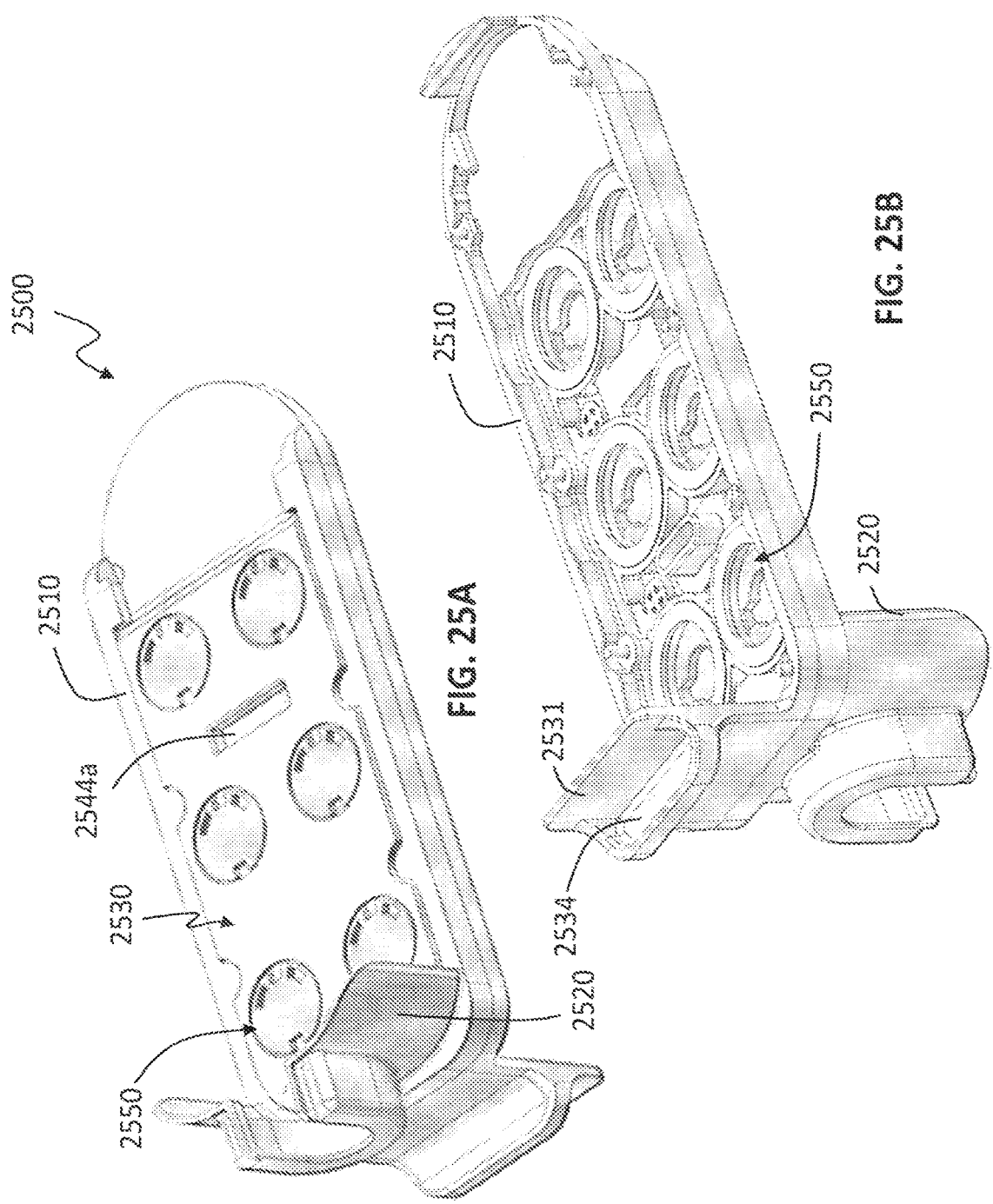

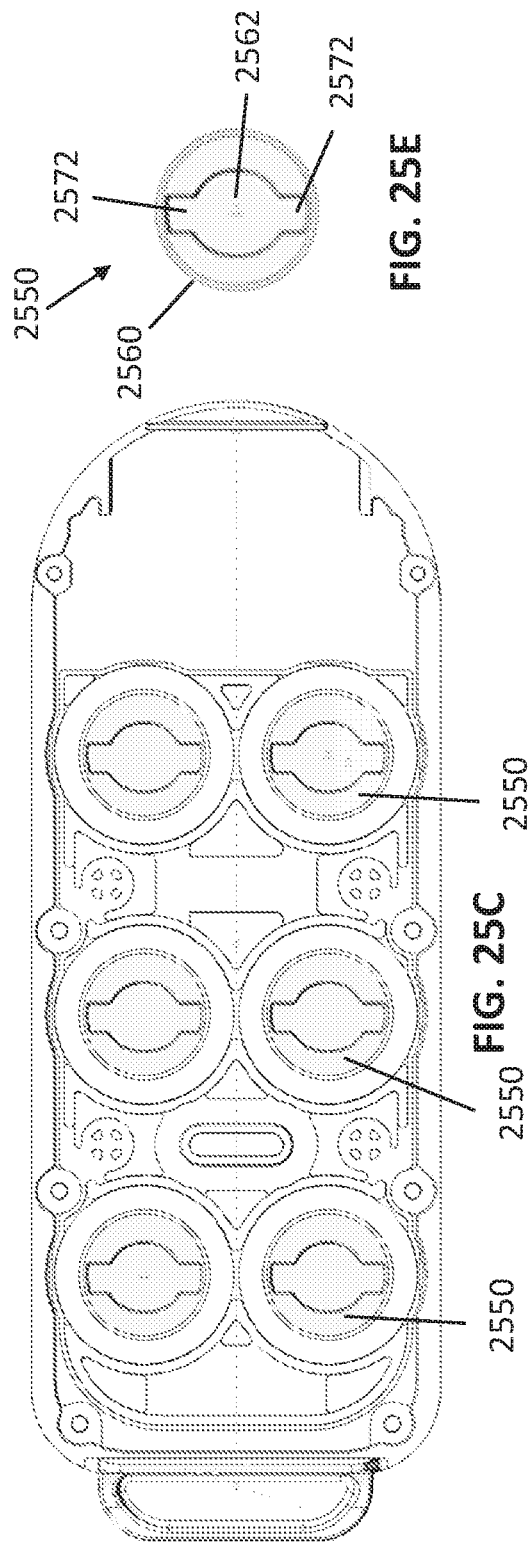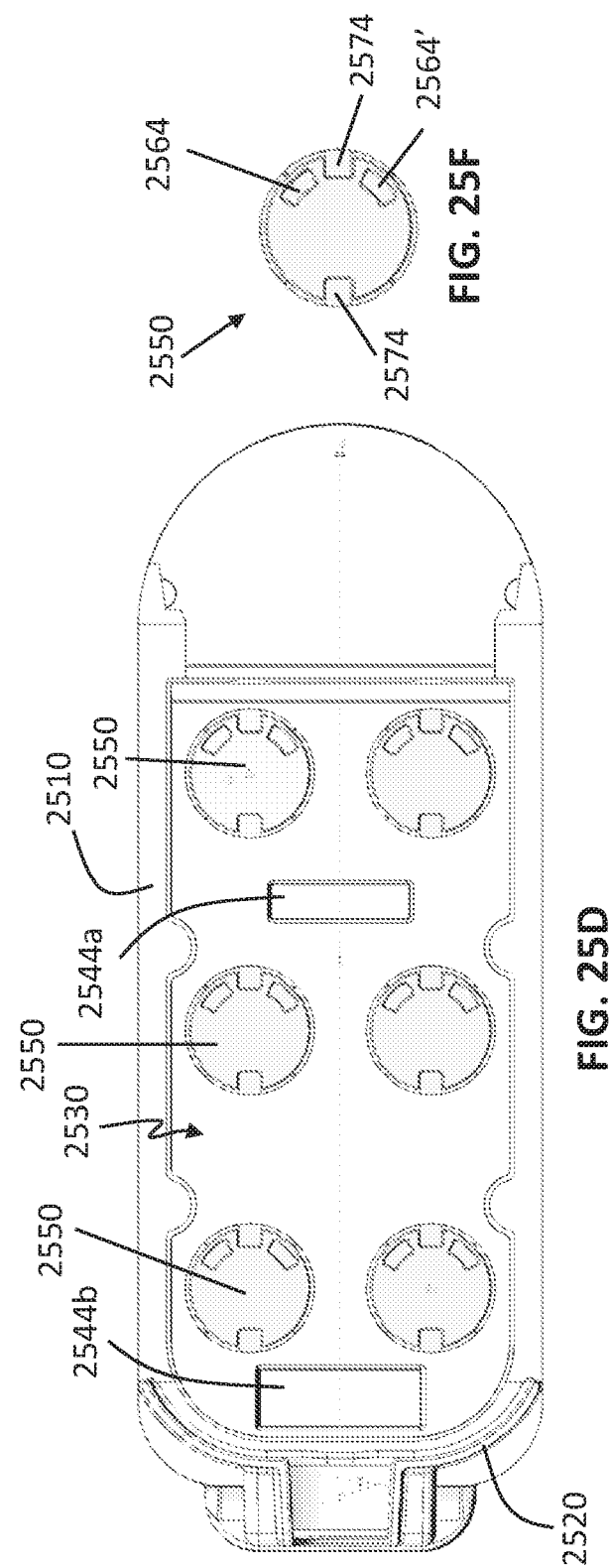

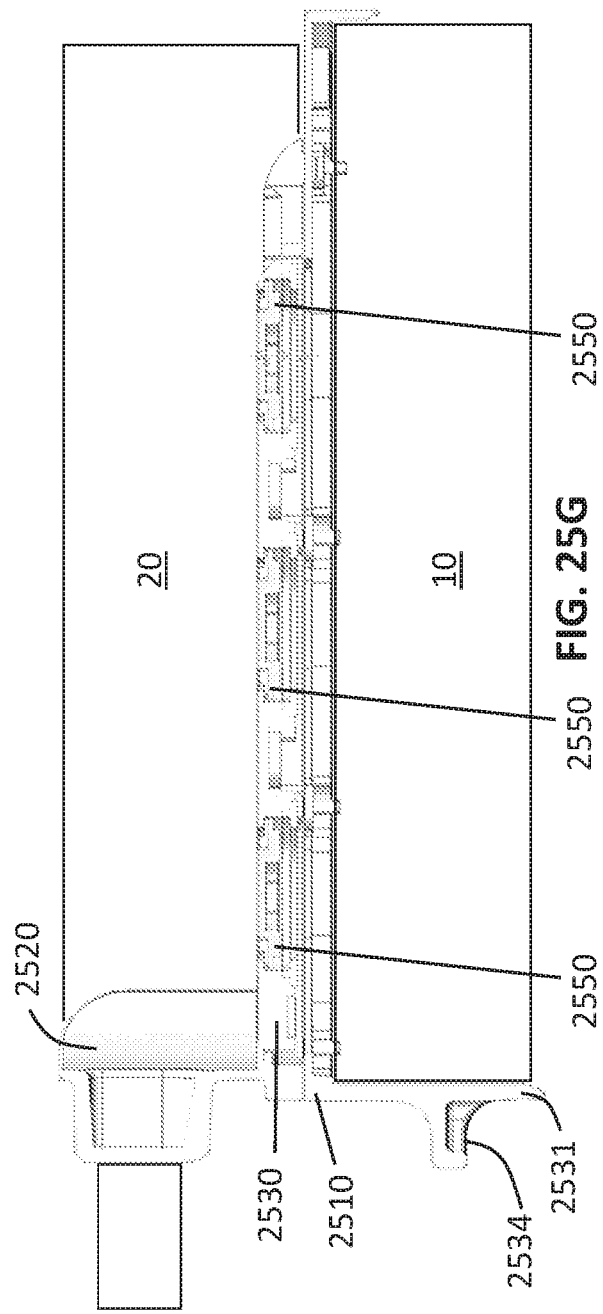

STERILE ADAPTER DRIVE DISKS FOR USE IN A ROBOTIC SURGICAL SYSTEM

CROSS-REFERENCE TO RELATED APPLICATIONS

This application claims priority to U.S. Patent Application Ser. No. 62/436,957, filed on Dec. 20, 2016, and to U.S. Patent Application Ser. No. 62/436,965, filed on Dec. 20, 2016, and to U.S. Patent Application Ser. No. 62/436,974, filed on Dec. 20, 2016, and to U.S. Patent Application Ser. No. 62/436,981, filed on Dec. 20, 2016, each of which is hereby incorporated by reference in its entirety.

TECHNICAL FIELD

This invention relates generally to robotic surgical systems, and more specifically to new and useful sterile adapters for creating a sterile barrier around portions of a robotic surgical system.

BACKGROUND

Minimally-invasive surgery (MIS), such as laparoscopic surgery, involves techniques intended to reduce tissue damage during a surgical procedure. For instance, laparoscopic procedures typically involve creating a number of small incisions in the patient (e.g., in the abdomen), and introducing one or more tools and at least one camera through the incisions into the patient. The surgical procedures are then performed by using the introduced tools, with the visualization aid provided by the camera. Generally, MIS provides multiple benefits, such as reduced patient scarring, less patient pain, shorter patient recovery periods, and lower medical treatment costs associated with patient recovery.

MIS may be performed with non-robotic or robotic systems. Conventional robotic systems, which may include robotic arms for manipulating tools based on commands from an operator, may provide many benefits of MIS while reducing demands on the surgeon. Control of such robotic systems may require control inputs from a user (e.g., surgeon or other operator) via one or more user interface devices that translate manipulations or commands from the user into control of the robotic system. For example, in response to user commands, a tool driver having one or more motors may actuate one or more degrees of freedom of a surgical tool when the surgical tool is positioned at the surgical site in the patient.

Similar to traditional surgical procedures, it is important to maintain a sterile environment in the surgical field during robotic MIS. However, various components (e.g., motors, encoders, sensors, etc.) of the tool driver and other aspects of the robotic surgical system cannot practically be sterilized using conventional sterilisation methods such as heat. One solution to maintain sterility is to provide a sterile barrier between the tool driver (and other system components that may appear in the surgical field such as robotic arms, etc.) and the surgical tool, thereby providing a "non-sterile" side for the tool driver and a "sterile" side for the surgical tool. However, the sterile barrier must not interfere with how the tool driver actuates the surgical tool. Furthermore, as a tool driver may need to actuate different surgical tools throughout a surgical procedure, the sterile barrier may facilitate simple and efficient exchange or swapping of surgical tools on a tool driver, without compromising the sterile barrier.

Thus, it is desirable to have new and improved sterile adapters in a sterile barrier for use in robotic surgery.

SUMMARY

Generally, a sterile adapter for use in a robotic surgical system may include a frame configured to be interposed between a tool driver and a surgical tool, a plate assembly coupled to the frame, and at least one rotatable coupler supported by the plate assembly and configured to communicate torque from an output drive of the tool driver to an input drive of the surgical tool. In one variation, the plate assembly may include a plurality of tool engagement features, where each tool engagement feature is mateable with a corresponding adapter engagement feature on the surgical tool. The frame may be configured to couple to the surgical tool when each tool engagement feature is mated with its corresponding adapter engagement feature on the surgical tool. The tool engagement features on the sterile adapter may, for example, include a plurality of recesses and/or protrusions that are arranged in a linear series of progressively increasing length along a tool insertion direction.

In another aspect, the plate assembly in the sterile adapter may include at least one abutment. The surgical tool may be configured, for example, to deliver a force directed along a longitudinal axis of the surgical tool, and the abutment of the sterile adapter may be configured to transmit the force to the tool driver. For example, the abutment may include a rib or other projection on a tool driver-facing surface of the sterile adapter, where the rib is configured to extend into a surface of the tool driver in order to transfer a force received by the plate assembly and rib to the tool driver.

In another aspect, the plate assembly may include a first face and a second face opposite the first face, where the first face may include at least one spring that is configured to urge the second face toward the surgical tool. The spring may include, for example, a beam spring, a coil or leaf spring, or other compliant material suitable for urging the second face of the plate assembly toward the surgical tool.

Generally, in other variations, a sterile adapter for use in a robotic surgical system may include a frame, a plate assembly coupled to the frame, and at least one rotatable coupler supported by the plate assembly and configured to communicate torque from an output drive of a tool driver to an input drive of a surgical tool. The coupler may, for example, include a first face having a first engagement feature configured to engage the output drive of the tool driver, and a second face having a second engagement feature configured to engage the input drive of the surgical tool. The first and second engagement features may have different shapes. For example, one or both of the engagement features may include a recess for engaging a projection on the output drive or input drive (and/or a projection for engaging a channel on the output drive or input drive). In another example, the first engagement feature may include an arcuate feature (e.g., recess or projection) and the second engagement feature may include a central feature (e.g. recess or projection) substantially centered on an axis of rotation of the rotatable coupler. The first and second engagement features may extend in opposite axial directions in the coupler (e.g., both may be recesses extending into the body of the coupler, or both may be projections extending outwards from the body of the coupler). Furthermore, the first face of the rotatable coupler may include a first set of pin holes for engaging with the output drive of the tool driver, and the second face may include a second set of pin holes for engaging with the input drive of the surgical tool.

The frame of the sterile adapter may, in other variations, include a body configured to be interposed between a tool driver and a portion of a surgical tool, and a mount projecting from the body for receiving the portion of the surgical tool. The body of the frame may include a first end and a second end opposite the first end, where in some variations an engagement feature may be disposed on the first end of the body for coupling to a first portion of the surgical tool overhanging the body and/or a platform mount may project (e.g., perpendicularly) from the second end of the body for receiving a second portion of the surgical tool. A movable locking member may be included in the sterile adapter and be selectively operable between an engaged position in which the locking member secures a coupling of the frame to the tool driver and a disengaged position in which the locking member facilitates a decoupling of the frame from the tool driver. For example, in some variations, the disengaged position may be blocked when the portion of the surgical tool is received in the mount, thereby substantially preventing the sterile adapter from de coupling from the tool driver when the surgical tool is received in the mount.

A sterile adapter may be part of a sterile barrier system that further includes a sterile drape. For example, a sterile barrier for use in a robotic surgical system may include a sterile adapter including a frame configured to be interposed between a tool driver and a surgical tool, where the frame has a frame perimeter, and at least one peripheral projection may extend laterally around at least a portion of the frame perimeter (e.g., as a flange or partial flange). A sterile drape may then be coupled to the projection, such as by thermal bonding or another suitable coupling process, to form at least part of the sterile barrier system. In some variations, the peripheral projection may include a flexible elastomeric material, and the frame and the at least one peripheral projection may be co-injection molded.

BRIEF DESCRIPTION OF THE DRAWINGS

FIG. 3A is a perspective view of an exemplary subassembly of a tool driver and a sterile adapter coupled to the tool driver. FIG. 3B is a perspective view of an exemplary subassembly of a tool driver, surgical tool, and sterile adapter interposed between the tool driver and the surgical tool.

FIG. 4A is a perspective view of one variation of a sterile adapter with a mount. FIG. 4B is a side view of an exemplary arrangement of a surgical tool coupled to the sterile adapter shown in FIG. 4A.

FIG. 6A is a perspective view of a variation of a sterile adapter with a locking member.

FIG. 6B is a perspective view of an exemplary arrangement of a tool driver and a surgical tool coupled to the sterile adapter shown in FIG. 6A.

FIG. 9A is a perspective view of one variation of a sterile adapter including a series of tool engagement features. FIG. 9B is a front side view of one variation of a surgical tool including a series of adapter engagement features for engaging with the series of tool engagement features depicted in FIG. 9A. FIG. 9C is an exemplary angled profile of adapter engagement features.

FIG. 11B is a cross-sectional schematic of a tool driver, a sterile adapter with springs, and a surgical tool.

FIG. 12B is a perspective view of a sterile barrier including the sterile adapter depicted in FIG. 12A.

FIGS. 17A-17C illustrate an exemplary process of coupling a tool driver to one variation of a sterile adapter with a removable film.

FIGS. 18A-18D illustrate an exemplary variation of coupling a tool to another variation of a sterile adapter.

FIGS. 19A and 19B illustrate an exemplary variation of decoupling a tool from the variation of a sterile adapter shown in FIGS. 18A-18D.

FIGS. 20A and 20B illustrate an exemplary variation of coupling a tool to another variation of a sterile adapter.

FIG. 21A is a front view of one variation of a sterile adapter. FIG. 21B is a perspective view of one variation of a tool configured to engage the sterile adapter depicted in FIG. 21A. FIG. 21C is an illustrative schematic of the tool depicted in FIG. 21B in the process of being attached to the sterile adapter depicted in FIG. 21A.

FIGS. 23A and 23B are rear and front perspective views, respectively, of one variation of a sterile adapter with an axially shifting plate in which the couplers of the sterile adapter are retracted. FIG. 23C is a perspective view of an exemplary surgical tool configured to engage with the sterile adapter depicted in FIGS. 23A and 23B.

FIGS. 24A and 24B are rear and front perspective views, respectively, of the sterile adapter depicted in FIGS. 23A and 23B in which the couplers of the sterile adapter are extended.

FIG. 24C is a perspective view of an exemplary surgical tool configured to engage with the sterile adapter depicted in FIGS. 24A and 24B.

FIGS. 25A and 25B are tool-side and tool driver-side perspective views, respectively, of another exemplary variation of a sterile adapter. FIG. 25C is a tool-side view of the sterile adapter depicted in FIGS. 25A and 25B. FIG. 25D is a tool driver-side view of the sterile adapter depicted in FIGS. 25A and 25B. FIGS. 25E and 25F are first and second sides of a rotatable coupler. FIG. 25G is a cross-sectional view of the sterile adapter depicted in FIGS. 25A and 25B.

DETAILED DESCRIPTION

Examples of various aspects and variations of the invention are described herein and illustrated in the accompanying drawings. The following description is not intended to limit the invention to these embodiments, but rather to enable a person skilled in the art to make and use this invention.

Figure 1:
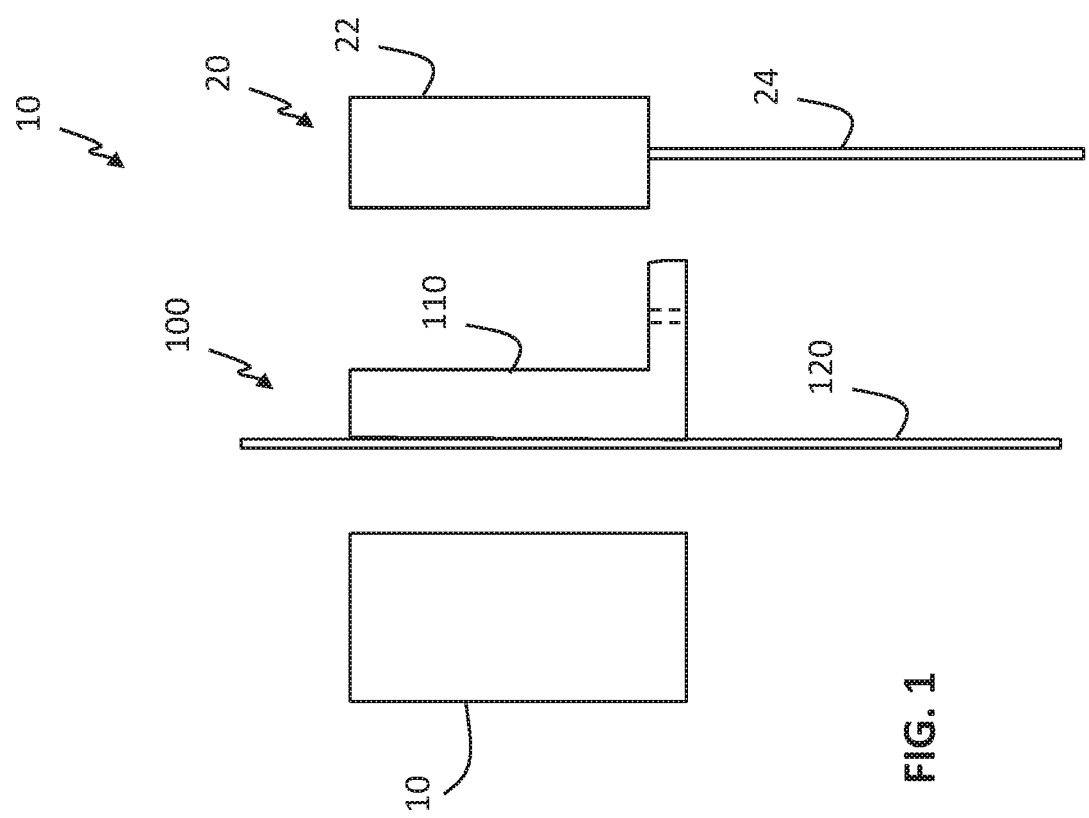
FIG. 1 is an illustrative schematic of a portion of a robotic surgical system with a tool driver, surgical tool, and a sterile barrier.

As shown generally in the schematic of FIG. 1, a portion of a robotic surgical system includes a tool driver 10 configured to actuate a surgical tool 20. One or more drive outputs on the tool driver 10 may, for example, actuate one or more drive inputs on a proximal portion 22 of the surgical tool 20, thereby causing movement (e.g., grasping, cutting, etc.) of an end effector located at a distal end of tool shaft 24. Additionally, a sterile barrier 100 may be placed between the tool driver 10 and the surgical tool 20, forming a barrier between an interior, non-sterile side including the tool driver 10 and an exterior, sterile side including the surgical tool 20 which may, for example, be located at a sterile surgical site. The sterile barrier 100 may, for example, include a sterile drape 120 configured to cover at least the tool driver 10, and a sterile adapter 110 coupled to the sterile drape 120 and located between the tool driver 10 and the surgical tool 20. The sterile adapter 110 may be configured to communicate or otherwise transmit actuation forces (e.g., rotary torque, linear movement, etc.) from at least one drive output of the tool to at least one drive input of the surgical tool 20. Examples of sterile barriers 100, such as variations of sterile adapters 110, are described in further detail herein.

Sterile Adapter

Figure 2C:
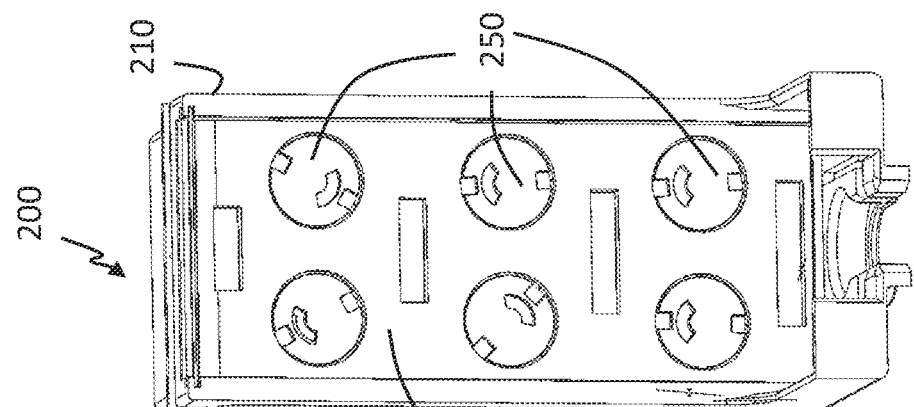
FIGS. 2A-2C are various perspective views of one variation of a sterile adapter.
Figure 2B:
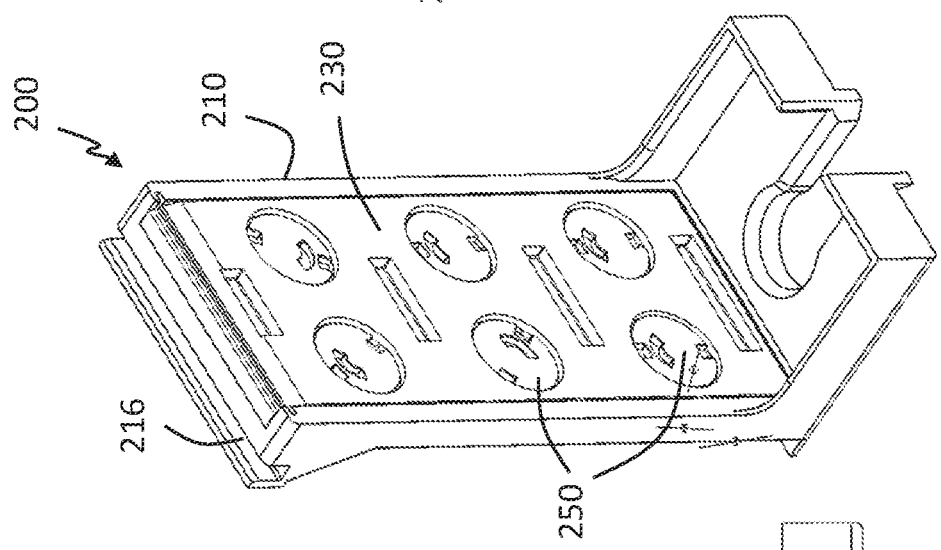
Figure 2A:
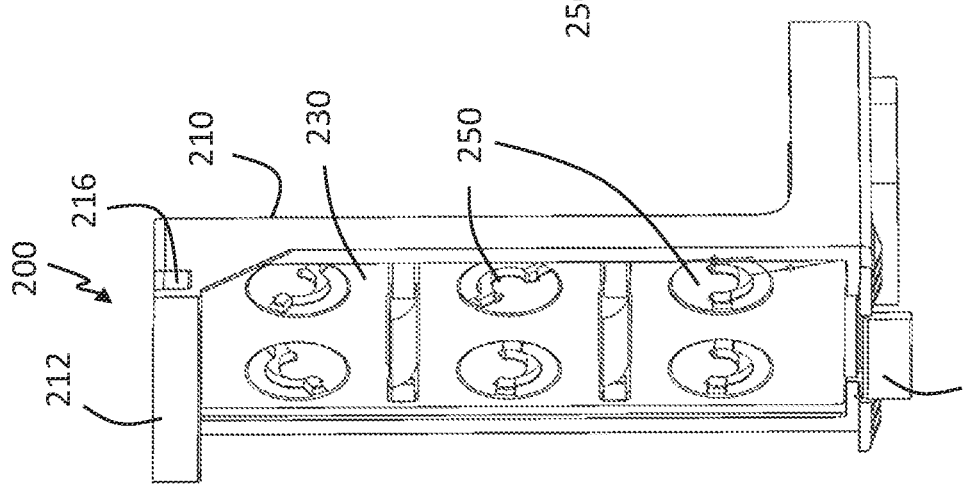

In one variation, as shown in FIGS. 2A-2C, a sterile adapter 200 may include a frame 210 configured to be interposed between a tool driver and a surgical tool, a plate assembly 230 coupled to the frame 210, and at least one rotatable coupler 250 supported by the plate assembly and configured to communicate torque from an output drive of the tool driver to an input drive of the surgical tool.

In some variations, the sterile adapter may be configured to communicate electrical signals, such as for communication and/or power (e.g., for sensors, etc.), between the tool driver and the surgical tool. For example, at least a portion of the sterile adapter, such as the frame, plate assembly, and/or at least one rotatable coupler may include metal contacts for transferring electrical signals between the tool driver and the surgical tool. Such metal contacts may, in some variations, may additionally or alternatively be used to signal to a controller and/or processor that the sterile adapter is coupled to the tool driver and/or to a surgical tool (in other variations, the tool driver and/or sterile adapter may include any suitable one or more sensors to detect the coupling of the sterile adapter to the tool driver and/or surgical tool, such as a proximity sensor or a capacitive sensor). Additionally or alternatively, signals and/or power may be wirelessly communicated (e.g., Bluetooth or other wireless communication protocol) in any suitable manner. For example, metal contacts may be omitted from the sterile adapter.

Frame

Generally, the frame 210 of the sterile adapter 200 may provide structural support for the sterile adapter 200, such as for detachably coupling the sterile adapter 200 to a tool driver and/or a surgical tool. For example, as shown in FIG. 2A, in one variation, the frame 210 may include a first engagement feature 212 and/or a second engagement feature 214. As shown in FIGS. 3A and 3B, the first engagement feature 212 may be configured to couple the frame 200 to first end of a tool driver 10, such as by including a lip that fits into a corresponding groove in the tool driver via a snap fit or other suitable physical interference. Additionally or alternatively, the first engagement feature 212 may include one or more magnets (not shown) such that the first engagement feature 212 may be guided and/or coupled to a suitable corresponding feature on the tool driver 10 based on magnetic attraction between the magnets on the first engagement feature 212 and magnets on the tool driver. Similarly, the second engagement feature 214 may be configured to couple the frame 210 to a second end of a tool driver 10, such as with a snap fit or other physical interference, and/or due to attractive magnetic forces. Although FIG. 2A depicts the first engagement feature 212 and the second engagement feature 214 as being on opposite ends (e.g., a proximal end and a distal end) of the frame and corresponding to opposite ends of the tool driver, it should be understood that the first engagement feature 212 and/or the second engagement feature 214 may be on lateral sides and/or any suitable part of the frame 210. Furthermore, fewer (e.g., one) or more (e.g., three, four, five, etc.) engagement features may be included and distributed among any suitable portions of the frame 210, with any suitable geometries (e.g., grooves, hooks, tabs, latches, other snap fits, etc.).

Although the first and second engagement features 212 and 214 are depicted generally as designed to couple to the tool driver via snap fit tabs extending from an edge of the frame 210, other variations of latching features or engagement features may be included. For example, a surface of the frame 210 may include a recess (e.g., channel, groove, hole, etc.) configured to receive and mate with a corresponding projection (e.g., ridge, pin, etc.) on the outward (drive output) face of the tool driver. The recess on the frame 210 may be sized relative to the projection so as to enable coupling of the tool driver and the frame 210 through an interference fit. Other features, such as angled barbs on the projection of the tool driver, or compliant and/or frictional elastomeric material on the projection or in the recess, may further facilitate detachably coupling the sterile adapter to the tool driver. Similarly, as another example, a surface of the frame 210 may include a projection configured to receive and mate with a corresponding recess on the tool driver.

Furthermore, as shown in FIGS. 2A and 2B, the frame may further include at least one tool engagement feature 216 configured to couple to a portion of a surgical tool. For example, as best shown in FIG. 3B, the tool engagement feature 216 may include a groove or other recess configured to receive a hook, lip or other overhanging projection or other feature of the surgical tool 20. In some variations, at least one tool engagement feature may be disposed on a proximal end (upper end as depicted in FIG. 2B) of the frame 210. Furthermore, at least one tool engagement feature may additionally or alternatively be disposed on a distal end (lower end as depicted in FIG. 2B) of the frame 210. Like the first and second engagement features 212 and 214 described above, the tool engagement feature 216 may include other variations of features and may be located at any suitable point on the frame 210.

As shown in FIGS. 2A-2C, generally, the frame 210 may further provide structural support for the plate assembly 230. For example, the frame 210 may include one or more slots around the perimeter of the opening within which the plate assembly 230 sits, such that the edges of the plate assembly 230 may engage the one or more slots of the frame 210. The slots may be sized with a suitable amount of clearance for the plate assembly, such that the plate assembly may shift at least in a direction transverse to the plane of the plate assembly, as described in further detail below. In one variation, the slots may be wider than the plate assembly thickness such that the plate assembly 230 may freely move within the slots. In another variation, one or more springs may be present in at least one slot such that the plate assembly 230 moves with some compliance.

As shown in FIGS. 2A-2C, the frame 210 may generally be rectangular, but may have any suitable shape (e.g., rectangular with rounded corners, elliptical, circular, etc.). For example, the shape of the frame 210 may correspond with the shape of the tool driver and/or the shape of the surgical tool to which the sterile adapter 200 is intended to couple. In some variations, the frame may be made at least partially of a rigid plastic (e.g., polycarbonate, acrylonitrile butadiene styrene (ABS), nylon, a polycarbonate-ABS blend, etc.) which may or may not include reinforcement material (e.g., glass or carbon fiber reinforcement) and/or additives such as a lubricious additive (e.g., polytetrafluoroethylene), talcum, etc. The frame may be injection molded, machined, 3D printed, or manufactured in any suitable process.

Mount

In some variations, the frame of the sterile adapter may include or be coupled to a projecting mount for receiving and coupling to the surgical tool. For example, as shown in FIGS. 4A and 4B, a sterile adapter 400 may include a body 410 configured to be interposed between a tool driver and a portion of a surgical tool, and a mount 420 projecting from the body and configured to receive the portion of the surgical tool. The mount 420 may generally assist in coupling the surgical tool to the sterile adapter 400, in that it may serve as a seat or surface to receive the surgical tool 20, such that when being coupled to the sterile adapter 400, the surgical tool 20 may contact the mount 420 for easy, efficient positioning of the surgical tool 20 against the sterile adapter 400 into the arrangement shown in FIG. 4B.

The mount 420 may include a shaft hole 424 configured to receive a tool shaft 24 of the surgical tool 20 during and after coupling of the surgical tool 20 to the sterile adapter 400. For example, the shaft hole 424 may guide and receive a tool shaft 24 passing longitudinally through the shaft hole 424 and through the mount 420. In some variations, the mount 420 may further include a shaft slot 426 configured to guide and receive a tool shaft 24 passed laterally into or across the mount 420 and into shaft hole 424. Furthermore, in some variations, the mount 420 may include a raised rim 422 or lip that helps constrain the seated portion of the surgical tool 22 (e.g., by preventing lateral sliding of the surgical tool). The raised rim 422 may extend around the entire perimeter of the mount 420 as shown in FIG. 4A. Alternatively, the mount 420 may include multiple raised tabs similar to raised rim 422, except that the multiple raised tabs may be distributed at a variety of points around the entire perimeter of the mount 420 (e.g., only at the corners and/or at some point along each edge of the mount 420). At least a portion of the shaft hole 424 and/or the shaft slot 426 may include an elastomeric or padded material where it contacts the tool shaft 24, which may frictionally reduce relative movement between the tool shaft 24 and the sterile adapter and/or reduce potential damage to the tool shaft 24.

Figure 7D:
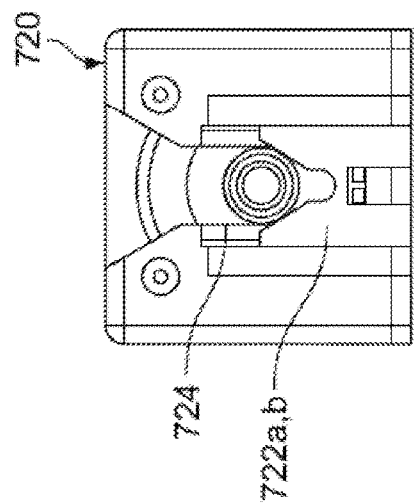
FIGS. 7B-7D are illustrative schematics of various sizes of adjustable shaft holes.
Figure 7A:
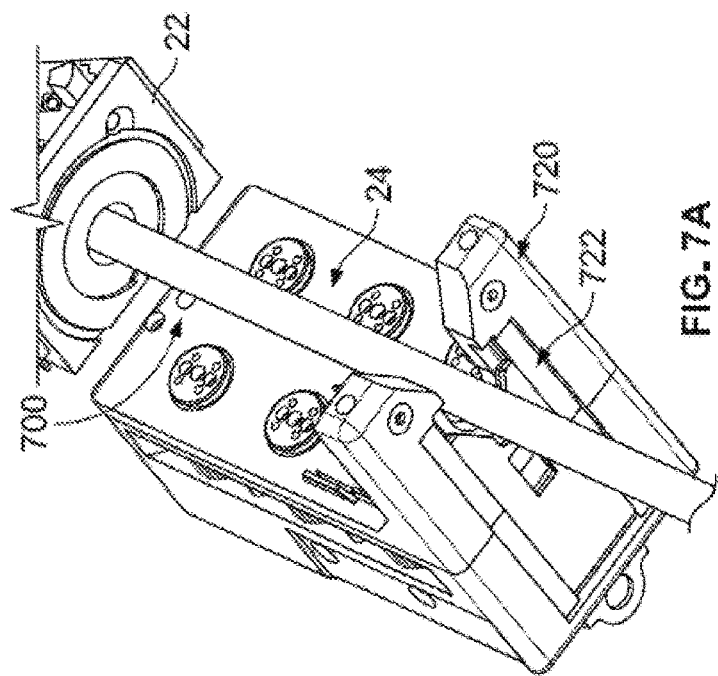
FIG. 7A is a perspective view of an exemplary arrangement of a tool driver and a surgical tool coupled to a sterile adapter with adjustable shaft holes.
Figure 7C:
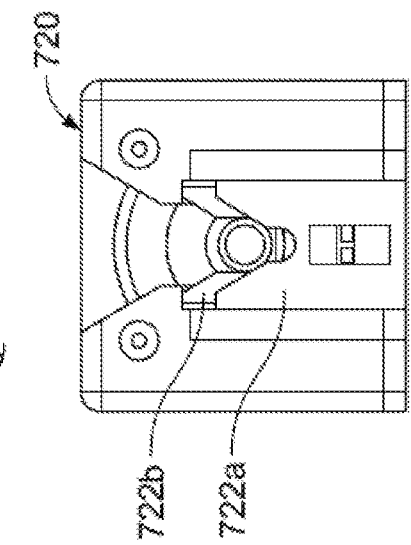

The shaft hole and/or the shaft slot may be adjustable to create a passageway for guiding different sizes of tool shafts 24 through the mount. In one variation of a sterile adapter 700, as shown in FIG. 7A, the mount 720 may include one or more shutters 722 that adjust the opening size (e.g., diameter) of the shaft hole to center (and reduce the amount of misalignment, play, or "wiggling" of) different-sized tool shafts 24 passing through the mount. For example, as shown in FIG. 7C, the mount 720 may include a first shutter 722a defining a passageway corresponding to a first tool shaft diameter, and a second shutter 722b defining a passageway corresponding to a second tool shaft diameter that is larger than the first tool shaft diameter. As shown in FIG. 7D, the mount 720 may include a shaft hole 724 defining a passageway corresponding to a third tool shaft diameter that is larger than the first and second tool shaft diameters. Fewer or more shutters 722 may be included to guide or correspond to fewer or more sizes of tool shaft diameters. Each shutter may be operable between an inactive position (in which the shutter's passageway does not intersect with the path of the tool shaft 24) and an active position (in which the shutter's passageway does intersect with the path of the tool shaft 24). One or more of the shutters may, for example, be configured to linearly slide in and out of the path of the tool shaft 24, or pivotably swing in and out of the path of the tool shaft 24. One or more of the shutters may be spring-loaded to bias the shutter toward the tool shaft 24.

Figure 7B:
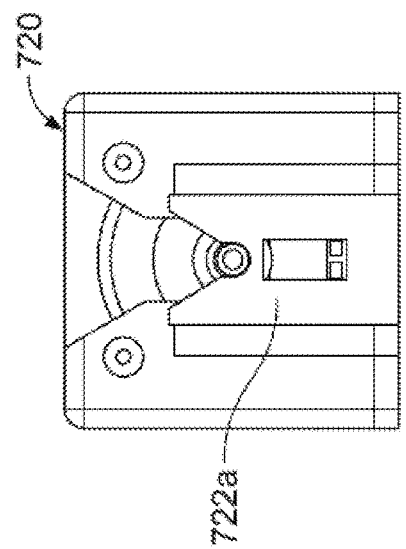

As shown in FIG. 7B, at least the first shutter 722a may be urged into its active position so as to permit a tool shaft 24 having the first tool shaft diameter (or smaller) to pass through the mount. The second shutter 722b may (or may not) additionally be urged into its active position in order provide a tapered passageway to gradually guide the tool shaft 24 from the larger shaft hole 724 into the smaller passageway provided by the first shutter 722a. The first shutter 722a reduces the amount of possible misalignment and lateral movement experienced by a tool shaft 24 having the first tool shaft diameter and passing through the first shutter 722a. As shown in FIG. 7C, the first shutter 722a may be retracted into its inactive position and the second shutter 722b may be urged into its active position, so as to permit a tool shaft 24 having the second tool shaft diameter (or smaller) to pass through the mount. The second shutter 722b reduces the amount of possible misalignment and lateral movement experienced by a tool shaft 24 having the second tool shaft diameter and passing through the second shutter 722a. As shown in FIG. 7D, the first shutter 722a and the second shutter 722b may be urged into their inactive positions so as to permit a tool shaft 24 having the third tool shaft diameter (or smaller) to pass through the shaft hole 724 of the mount. The shaft hole 724 may be sized to reduce the amount of possible misalignment and lateral movement experienced by a tool shaft 24 having the third tool shaft diameter.

In another variation of a sterile adapter having an adjustable shaft hole size for the different tool shaft sizes, the mount may include a radially-adjustable shutter adjacent the shaft hole that accommodates and adjusts to different tool shaft diameters. For example, the radially-adjustable shutter may include a leaf shutter with overlapping blades that progressively slide to constrict or expand the passageway for tool shaft 24. As another example, the radially-adjustable shutter may include members that extend or are angled generally radially inwards into the shaft hole (or generally lean centrally toward the path of the tool shaft 24) to center the tool shaft 24 in the shaft hole. The members may, for example, be flexible (e.g., bristles, bendable fingers, etc.) such that they may bend less to accommodate smaller tool shaft sizes and bend more to accommodate larger tool shaft sizes. As yet another example, the members may be radially-adjustable in length and/or angle (e.g., telescopic members, spring-loaded pinchers) such that they may extend, retract, and/or pivot radially to accommodate different tool shaft sizes.

Figure 5B:
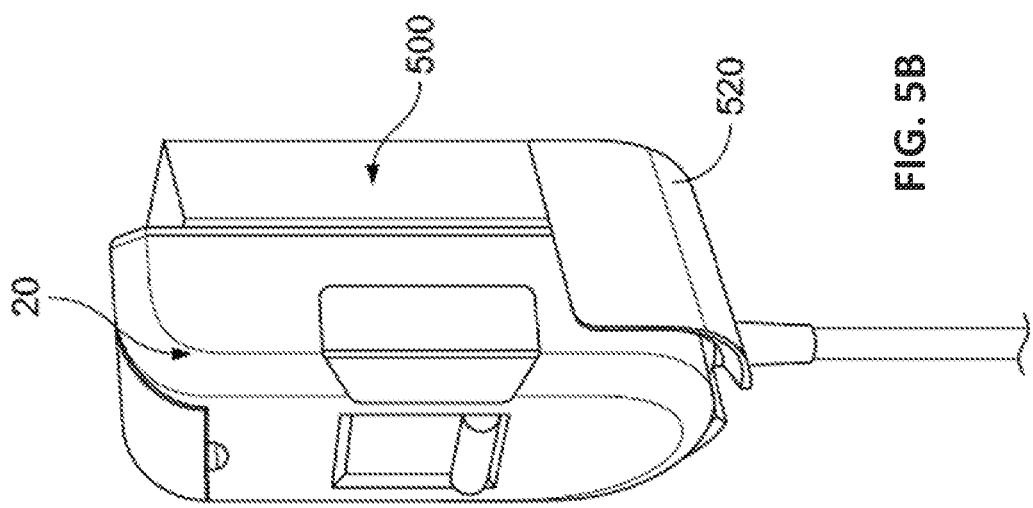
FIG. 5B is an illustrative schematic of the surgical tool coupled to the sterile adapter shown in FIG. 5A.
Figure 5A:
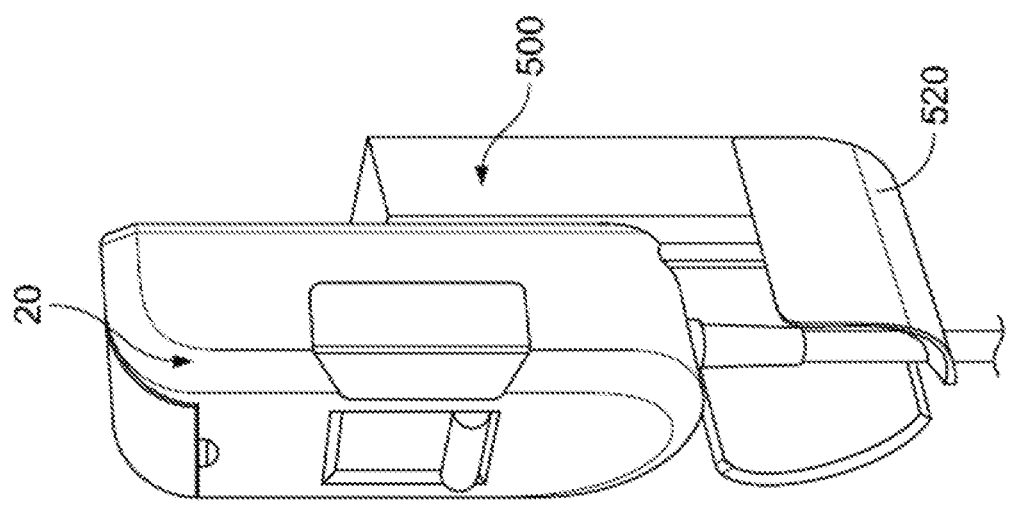
FIG. 5A is an illustrative schematic of a surgical tool in the process of coupling to another variation of a sterile adapter with a curved mount.

As shown in FIGS. 4A and 4B, in one variation, the mount 420 may include a substantially planar platform in order to accommodate a planar surface of the proximal portion 22 of the surgical tool 20. However, the mount may have any suitable shape, which may correspond with, for example, the shape of the surgical tool 20 that it receives. For example, as shown in FIGS. 5A and 5B, a sterile adapter 500 may include a mount 520 that is curved (e.g., semi-circular) to engage with a correspondingly curved surface of surgical tool 20, similar to a ball-and-socket joint. Another example of a curved mount is shown in FIGS. 25A-25D and FIG. 25G. Mount 2520 includes a medial section that is substantially planar, and includes lateral curved sections extending beyond either side of the medial section. As shown FIG. 25G, the mount 2520 may be configured to receive and/or engage with a tool 20, similar to the mounts described above. Furthermore, the mount may include multiple components, such as a plurality of extending arms or a latticework of multiple members, which work collectively to cradle or otherwise receive the proximal portion of the surgical tool.

As shown in FIGS. 4A and 4B, in one variation, the mount 420 may project generally perpendicularly (about 90 degrees) from the body 410 of the sterile adapter frame. However, the mount 420 may project from the body 410 at any suitable angle, which may depend on the shape of the surgical tool 20 that is receives. For example, the profile of the portion of the surgical tool to be received in the mount may include an angle or curvature along its leading edge, and the mount 420 may be correspondingly angled or curved to receive the surgical tool.

The mount 420 may enable multiple techniques for coupling the surgical tool to the sterile adapter. Multiple techniques may be useful, for example, to accommodate different user preferences and/or facilitate easy tool swapping or exchange when the tool driver is in different positions or orientations (e.g., generally vertical, generally horizontal, or at other angles) and present different user access options to the tool driver. For example, in one technique, a user may guide the surgical tool generally longitudinally along the frame 410 (and face of the plate assembly 430), allowing the tool shaft 24 to pass longitudinally through the shaft hole 424 and/or shaft slot 426 of the sterile adapter. The user may continue to guide the surgical tool longitudinally, until the proximal portion 22 of the surgical tool is seated in the mount 420 and/or the lip 23 of the surgical tool engages the engagement feature 416 of the tool driver, thereby coupling the tool 20 to the sterile adapter 400 in the arrangement shown in FIG. 4B. In another exemplary technique, a user may guide the surgical tool generally laterally toward the tool-side face of the plate 430, allowing the tool shaft 24 to pass through shaft slot 426 of the sterile adapter into the shaft hole 424. The user may continue to guide the surgical tool laterally, until at least a portion of the surgical tool contacts the frame 410 and/or plate assembly 430, then subsequently guide the surgical tool longitudinally until the surgical tool is seated in the mount 420. In another exemplary technique, a user may angle the surgical tool in its approach toward the sterile adapter (e.g., at 45 degrees relative to the plate assembly) and guide the leading end of the surgical tool toward the mount 420. Once the proximal portion 22 of the surgical tool is in contact with the mount 420, the user may lean the proximal portion 22 back against the body 410 of the sterile adapter until the surgical tool is seated in the mount 420. Furthermore, other techniques for coupling the tool and the sterile adapter may include combinations of aspects of these techniques. Advantageously, coupling the tool and the sterile adapter with the aid of a mount 420 is not limited to one technique (e.g., solely the technique of longitudinally sliding the tool onto the sterile adapter), such that a user may select a technique best suited for him or her, and/or best suited in a particular circumstance where access to the tool driver may be limited in a certain manner.

As shown in FIG. 4A, the body 410 and the mount 420 may be integrally formed as one piece (e.g., injection molded, milled, etc.). Alternatively, the body 410 and the mount 420 may be formed as separate pieces, and the mount 420 may be coupled to the body with fasteners (e.g., screws), interlocking features such as interlocking tabs, epoxy or other suitable adhesive, and/or any suitable coupling method.

In some variations, the sterile adapter may further include a movable locking member for securing the sterile adapter to the tool driver. The locking member may be selectively operable between an engaged position and a disengaged position. In the engaged position, the locking member may secure a coupling of the frame to the tool driver. In the disengaged position, the locking member may facilitate a decoupling of the frame from the tool driver.

For example, in one variation as shown in FIGS. 6A and 6B, a sterile adapter 600 may include a locking member 630. The locking member may be coupled to a body 610 and/or mount 620 of the sterile adapter 600. The locking member 630 may include at least one end 630a configured to couple to the tool driver 10, such as with an engagement feature 632 (e.g., an opening or recess configured to engage with a projection on the tool driver 10). The locking member 630 may include, for example, a lever that pivots around Axis A to toggle between an engaged position and a disengaged position. In one variation as shown best in FIG. 6B, the locking member 630 may further include a second end 630b configured to engage or otherwise contact the tool (e.g., the second end 630b may include the shaft hole 624 through which tool shaft 24 passes when the surgical tool 20 is seated in the mount 620), such that the disengaged position is blocked when the portion of the surgical tool is received in the mount. Accordingly, the locking member 630 may prevent decoupling of the sterile adapter 600 from the tool driver when the surgical tool is received in the mount. This kind of "lockout" feature may be advantageous, for example, during tool exchange in order to help ensure that the sterile adapter 600 remains in place (e.g., significantly reduce the likelihood that the sterile adapter is inadvertently decoupled from the tool driver) when surgical tools are swapped in and out of the sterile adapter frame and mount.

Although the locking member 630 is generally depicted as a lever in FIGS. 6A and 6B, it should be understood that in other variations, other members or mechanisms included or coupled to the sterile adapter may require movement into the space occupied by the surgical tool 20 in order to decouple the sterile adapter from the tool driver.

Figure 6C:
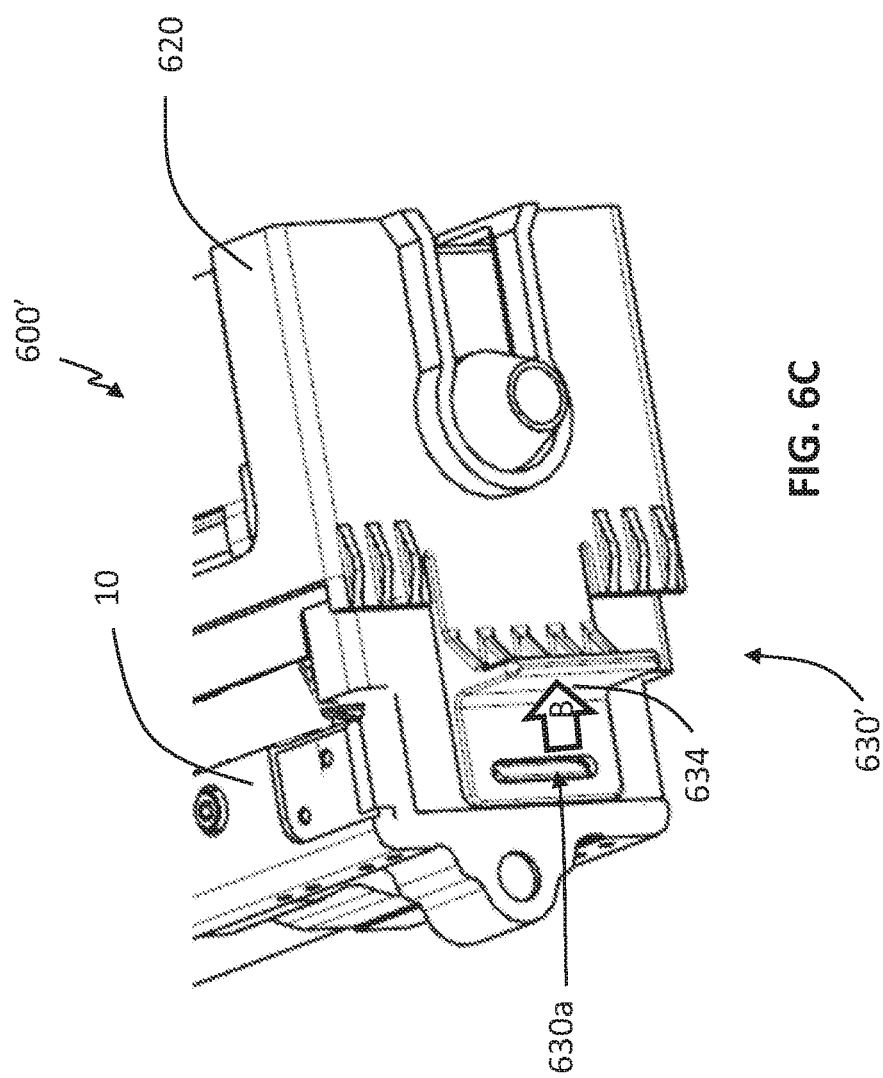
FIG. 6C is a perspective view of another variation of a sterile adapter with a locking member.

Alternatively, in another variation as shown in FIG. 6C, the locking member 630' may be configured to freely toggle between an engaged position and disengaged position regardless of the presence of the surgical tool. For example, a user may push a projection 634 in the direction indicated by the arrow B in order to decouple the first end 630a of the locking member from the tool driver 10. Similarly, as shown in FIG. 25G, a locking member 2531 may be configured to receive and/or engage with at least a portion of the tool driver 10. The locking member 2531 may include a projection 2534 that a user may push in order to decouple the locking member from the tool driver 10.

Drape Attachment

Figure 12A:
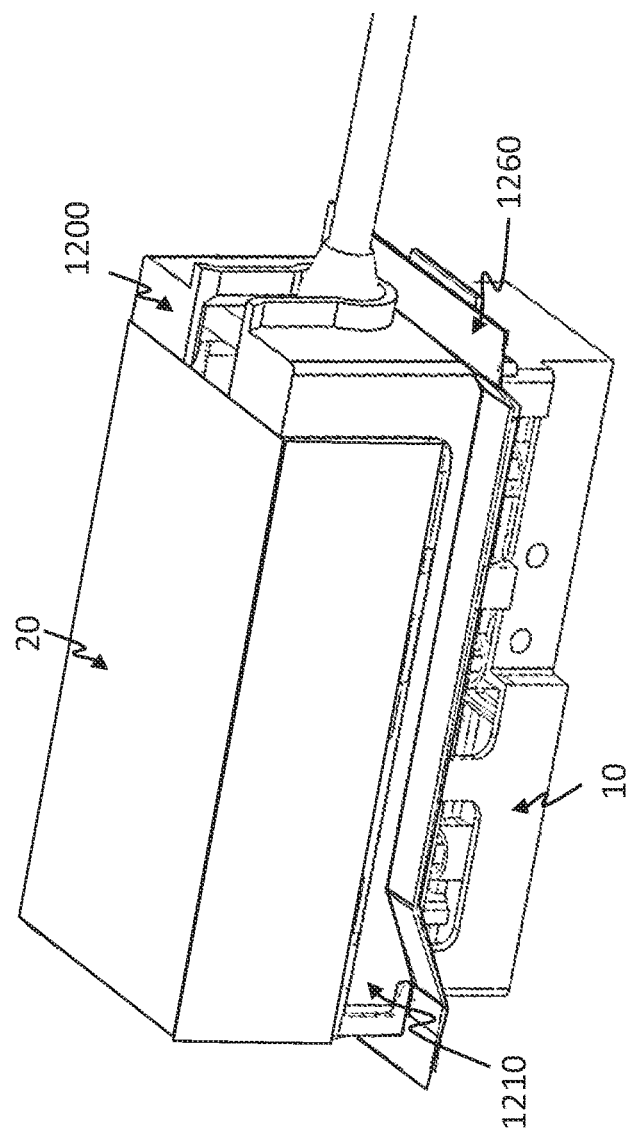
FIG. 12A is a perspective view of one variation of a sterile adapter including a peripheral projection.

In some variations, a sterile adapter may include a frame configured to be interposed between a tool driver and a surgical tool, wherein the frame has a frame perimeter, and at least one peripheral projection extending laterally around at least a portion of the frame perimeter. The peripheral projection may provide a surface to which a sterile drape may be coupled or attached, such that in combination the sterile adapter and the sterile drape form a sterile barrier. For example, as shown in FIG. 12A, a sterile adapter 1200 may include a frame 1210 configured to be interposed between a tool driver 10 and a surgical tool 20, and a peripheral projection 1260 extending laterally and around substantially the entirety of the perimeter or boundary of the frame 1210. As shown in FIG. 12B, a sterile drape 1270 may be coupled to the peripheral projection 1260, such as through thermal bonding, thereby forming a sterile barrier that may be used to cover the tool driver while enabling the tool driver 10 to actuate the surgical tool 20 via the rotatable couplings in the sterile adapter 1200.

The peripheral projection 1260 may extend a suitable distance for providing sufficient surface area for coupling the sterile drape 1270 to the peripheral projection 1260. For example, the peripheral projection 1260 may extend between about 0.2 cm and about 1.5 cm, between about 0.5 cm and about 1.0 cm, or between about 0.5 cm and 0.7 cm (e.g., about 0.6 cm), etc. in order to provide enough surface area for thermal bonding or another suitable coupling method to bond the sterile drape to the sterile adapter via the peripheral projection.

In some variations, the peripheral projection 1260 may include a different material than the frame 1210. For example, as described above, the frame 1210 may be made of a material that is relatively rigid, such as polycarbonate or ABS, while the peripheral projection 1260 may include a relatively more flexible material, such as a compliant elastomer such as a suitable thermoplastic elastomer (e.g., MEDIPRENE, SANTOPRENE, etc.). The flexible material of the peripheral projection 1260 may, for example, provide a rigid enough platform to allow for sterile drape attachment during assembly of the sterile barrier (or sufficiently rigid when back-supported during drape attachment with a fixture, etc.), while also being deformable (e.g., similar to a living hinge) to enable the sterile adapter to be more compact if needed (e.g., to enable adjacent or side-to-side placement of multiple tool drivers and/or surgical tools during a surgical procedure, thereby advantageously increasing available positioning and mobility of the robotic system). The sterile drape may be made of urethane or other suitable material.

One exemplary method of making a sterile adapter with a peripheral projection includes co-injection molding a frame and at least one peripheral projection that extends laterally around at least a portion of the perimeter of the frame, and coupling a sterile drape to the peripheral projection. The co-injection molding may include introducing a first material into a first portion of a mold corresponding to the frame, and introducing a second material that is less rigid than the first material into a second portion of the mold corresponding to the peripheral projection. Coupling the sterile drape to the peripheral projection may include thermal bonding, epoxy or other adhesive, fasteners, or any suitable attachment method.

In some variations, the frame may include multiple layers of peripheral projections. For example, the frame may include a first peripheral projection and a second peripheral projection overlying the first peripheral projection. The two layers of peripheral projections (each substantially similar to peripheral projection 1260, for example) may sandwich or clamp upon the sterile drape. The peripheral projections may be coupled together to secure the sterile drape between the peripheral projections, such as with thermal bonding, epoxy, etc.

Plate Assembly

The plate assembly functions to provide structural support for one or more rotatable couplers (e.g., discs as described in further detail below). For example, as shown in FIGS. 2A-2C for example, the plate assembly 230 may generally be disposed within an opening of the frame 210 and provide structural support for a plurality of rotatable couplers 250. Additionally or alternatively, the plate assembly may interact with the tool driver and/or surgical tool, such as to facilitate alignment, distribute load forces, etc.

Figure 8:
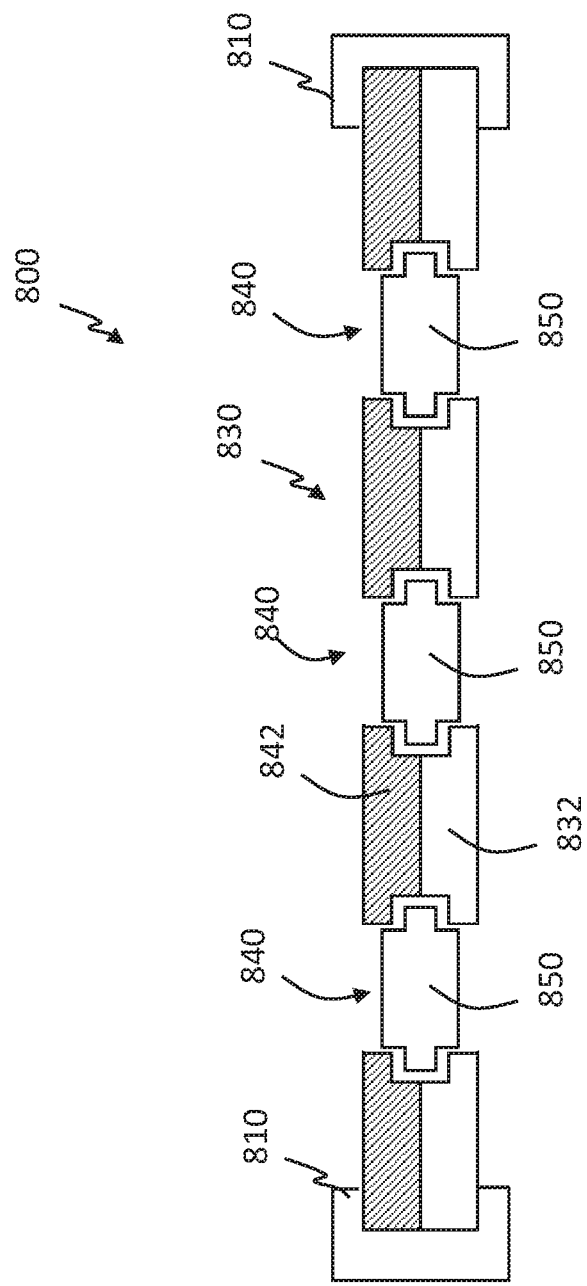
FIG. 8 is an illustrative cross-sectional schematic of a plate assembly with rotatable couplers in one variation of a sterile adapter.

As shown in an illustrative cross-sectional schematic of FIG. 8, in one variation, a sterile adapter 800 may include a frame 810 and a plate assembly 830 disposed within the frame 810. The plate assembly 830 may include at least one opening 840 for receiving a rotatable coupler 850. For example, the plate assembly 830 may include six openings 840 for receiving six rotatable couplers 850, though fewer (e.g., two, three, four, or five) or more (e.g., seven, eight, nine, or ten or more) openings 840 may be included in the plate assembly 830. The plate assembly may include multiple plates layered and coupled together. For example, as shown in FIG. 8, the plate assembly 830 may include a tool driver-side plate 832 and a tool-side plate 842. The multiple plates may be assembled around the rotatable couplers 850 so as to contain the couplers 850 within the openings 840, such as by coupling the tool driver-side plate 832 and the tool-side plate 842 with fasteners (e.g., screws, etc.), brackets, epoxy or other adhesive, and/or any suitable coupling mechanism. Alternatively the plate assembly may be one integrally formed piece to include openings 840. The openings 840 may be sized and shaped to permit the rotatable couplers 850 to move transverse to the plane of the plate assembly (i.e., up and down in the orientation shown in FIG. 8), and/or laterally generally within the plane of the plate assembly with low friction, while still being constrained in the opening 840. The plate assembly may include, for example, a rigid plastic or other suitable rigid material (e.g., polycarbonate, ABS, or other materials and compositions described above for the frame, aluminum, stainless steel or other suitable sheet metal, etc.), Like the frame, the plate assembly may be injection molded, machined, extruded, stamped, 3D printed, or manufactured in any suitable manner Tool Engagement Features In some variations, the plate assembly may include one or more alignment features that help ensure that the surgical tool is properly aligned with the sterile adapter before the surgical tool and sterile adapter couple to one another. In one variation, the plate assembly may include a series or pattern of one or more tool engagement features (e.g., on a tool-side plate of the plate assembly), where each tool engagement feature is mateable with a corresponding adapter engagement feature on the surgical tool. For example, at least one tool engagement feature may be mateable to a corresponding adapter engagement feature in a unique 1:1 pairing, and successful mating of the paired features may be required to enable the sterile adapter to couple to the surgical tool. Furthermore, in variations in which all of the tool engagement features have a respective unique 1:1 pairing with a corresponding adapter engagement feature, the sterile adapter (e.g., the frame) may be configured to couple to the surgical tool only when each and every tool engagement feature is mated with its corresponding adapter engagement feature on the surgical tool. Each of the tool engagement features may include a channel or recess of differing size (e.g., length, width, etc.) and/or shape (e.g., straight, curved, wavy, chamfered or not chamfered, etc.), and similarly, each of the adapter engagement features may include an outward projection of differing size and/or shape to engage with a respective tool engagement feature on the sterile adapter. In some variations, each (or at least one) of the tool engagement features may include a projection of differing size and/or shape, while each (or at least one) of the adapter engagement features may include a channel of differing size and/or shape to engage with a respective tool engagement feature on the sterile adapter.

In one example, the plate assembly 930 may include recessed tool engagement features 944a, 944b, 944c, and 944d as shown in FIG. 9A, and the surgical tool 20 may include outwardly projecting adapter engagement features 26a, 26b, 26c, and 26d. Tool engagement features 944a, 944b, 944c, and 944d may be configured to uniquely mate with adapter engagement features 26a, 26b, 26c, and 26d, respectively. Furthermore, the tool engagement features 944a-944d may be arranged in a series (e.g., sequential pattern or in another pattern), such as arranged by increasing width or length along a direction of tool insertion (e.g., longitudinally along the plate assembly 930 indicated by arrow C in FIG. 9A), though other patterns may possible in other variations. Only upon mating of each of these pairings is the sterile adapter permitted to fully couple to the surgical tool 20. Until this holistic mating occurs, the outwardly projecting adapter engagement features 26a-26d may physically interfere with the tool-side plate of the plate assembly 930, thereby urging the plate assembly 930 and the sterile adapter couplers 950 away from the surgical tool and its input couplers 28 and thus preventing coupling between the sterile adapter and the surgical tool. A similar coupling prevention effect may be achieved in a variation in which the tool engagement features 944a-944d are outwardly projecting and the adapter engagement features 26a-26d are recessed.

In one exemplary technique for coupling the tool 20 to the sterile adapter 900, the tool 20 may be moved longitudinally along the plate assembly 930, with the adapter engagement feature 26d encountering the tool engagement features 944a, 944b, and 944c, in that order, without mating due to physical interference (e.g., size and/or shape mismatch). Similarly, adapter engagement feature 26c encounters the tool engagement features 944a and 844b, and adapter engagement feature 26b encounters the tool engagement feature 944a, without mating due to physical interference. During this stage, the physical interference also pushes against and displaces the plate assembly 930 and its couplers 950 away from the surgical tool 20, thereby further preventing coupling between the sterile adapter 900 and the tool 20. After the tool 20 is further moved in the tool insertion direction, the adapter engagement feature 26d encounters the tool engagement feature 944d, as do the adapter engagement features 26a-26c with their respective tool engagement features 944a-944c. When all of the tool engagement features align and mate with their corresponding adapter engagement features, the sterile adapter 900 may couple to the surgical tool 20.

Furthermore, a projection on the plate assembly 930 or tool 20 (whether as a tool engagement feature or an adapter engagement feature) may have an angled profile (e.g., an angled fin) relative to the direction of tool insertion so as to help reduce physical interference during when the surgical tool 20 is sliding along the sterile adapter. For example, as shown in FIG. 9C, the adapter engagement features 26a and 26b on the surgical tool may be outward projections angled away from the direction of tool insertion indicated by arrow C in FIG. 9A, thereby making it easier for the tool to slide down onto the mount of the sterile adapter. Alternatively, the tool engagement features 944a-944d on the sterile adapter may be outward projections that are angled toward the direction of tool insertion, thereby making it easier for the sterile adapter to receive a tool sliding down onto the mount of the sterile adapter.

Although FIG. 9A depicts a plate assembly 930 having four tool engagement features, in other variations, there may be any suitable number of tool engagement features and adapter engagement features (e.g., one, two, three, five, six, seven, eight, or more of each). Furthermore, the tool engagement features may vary in width and/or shape. For example, as shown in FIG. 25C, plate assembly 2530 includes two tool engagement features 2544a and 2544b along the length of the plate assembly 2530, wherein a first tool engagement feature 2544a is shorter and narrower than a second tool engagement feature 2544b. Furthermore, while the tool engagement features on the sterile adapter are arranged in a linear series of progressively increasing width in the variation depicted in FIG. 9A, in other variations the tool engagement features may be in other suitable patterns (e.g., zig-zag, random, radial or concentric, etc.).

Force Transfer Features

In some variations, the plate assembly may include one or more abutments configured to transfer force received by the sterile adapter from the tool. For example, a surgical tool may be configured to deliver a force directed along a longitudinal axis of the surgical tool (e.g., the direction along the tool shaft 24), and the axial force may be transferred to the sterile adapter via the coupling between the sterile adapter and the surgical tool (e.g., via the mating of adapter engagement features on the tool to the tool engagement features on the sterile adapter, as described above). To prevent the sterile adapter from having to absorb this axial force (which may, for example, cause damage to the frame of the sterile adapter), the sterile adapter may include force transfer features abutting the tool driver, so as to cause the axial force to be transferred to the tool driver, which may be generally more robust than the sterile adapter and able to withstand such forces without damage.

Figure 10A:
FIG. 10A is a front side view of an exemplary tool driver.
Figure 10B:
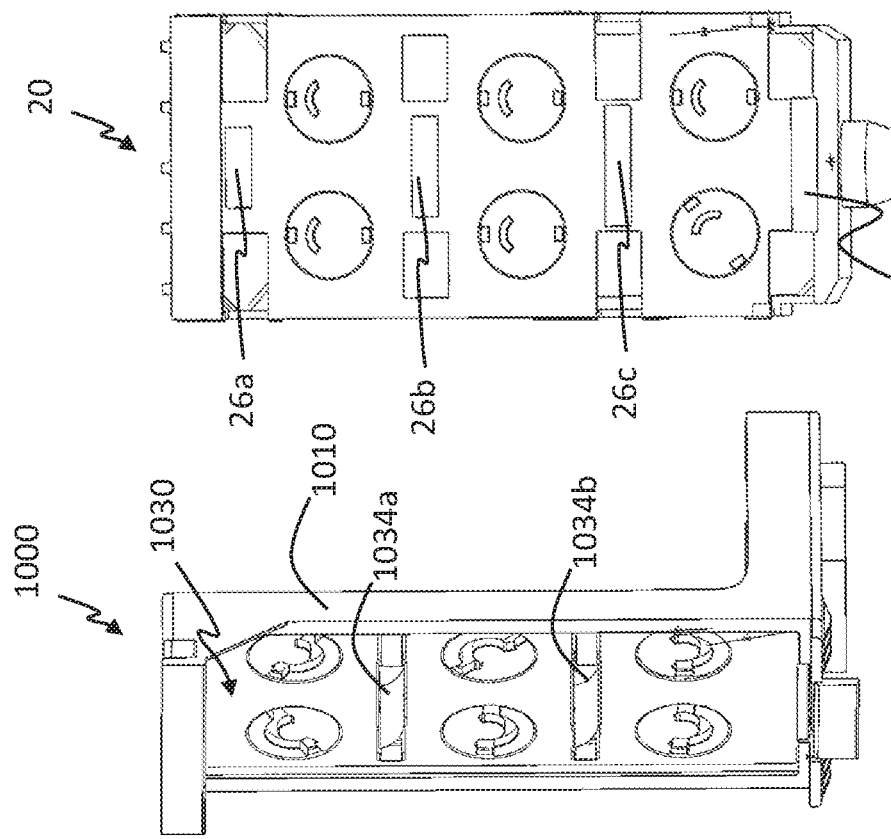
FIG. 10B is a perspective view of one variation of a sterile adapter including force-transferring abutment features.
Figure 10C:
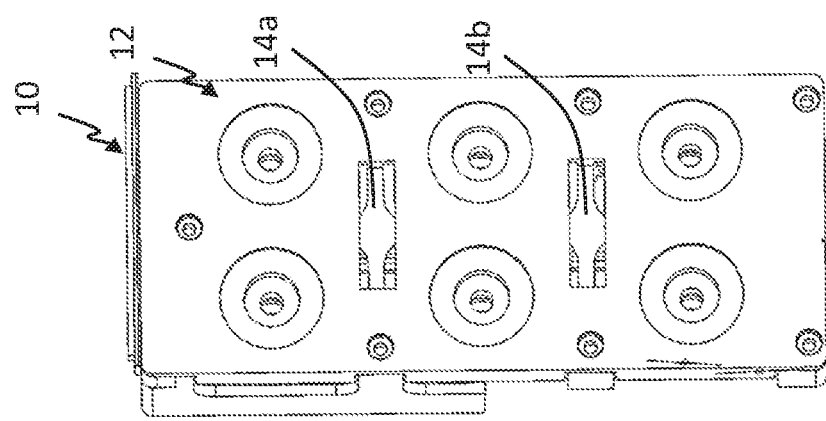
FIG. 10C is a front side view of an exemplary surgical tool.

One or more of the abutments may be an outward projection on a tool driver-side plate of the plate assembly that engages a recess in the tool driver 10. Additionally or alternatively, one or more of the abutments may be a wall of a recess in the tool driver-side plate of the plate assembly configured to receive an outward projection on the tool driver 10. For example, as shown in FIG. 10B, a sterile adapter 1000 may include a plate assembly 1030 with one or more outwardly projecting ribs, such as ribs 1034a and 1034b. The ribs 1034a and 1034b may engage and abut receptacles 14a and 14b, respectively, which are shown in FIG. 10A. Accordingly, when the tool driver 10, the sterile adapter 1000, and the tool driver 20 are engaged in combination, axial forces experienced by the tool 20 may be delivered to the sterile adapter 1000 (e.g., via adapter engagement features 26a-26c) and thereafter transferred to the tool driver 10 (e.g., via ribs 1034a and 1034b). Similar to the tool engagement features 944a-944d and/or adapter engagement features 26a-26d described above with reference to FIG. 9B, the outwardly projecting ribs 1034a and/or 1034b may be elongated and angled in profile, though they may have any suitable shape having sufficient surface area for abutting the tool driver.

Figure 10D:
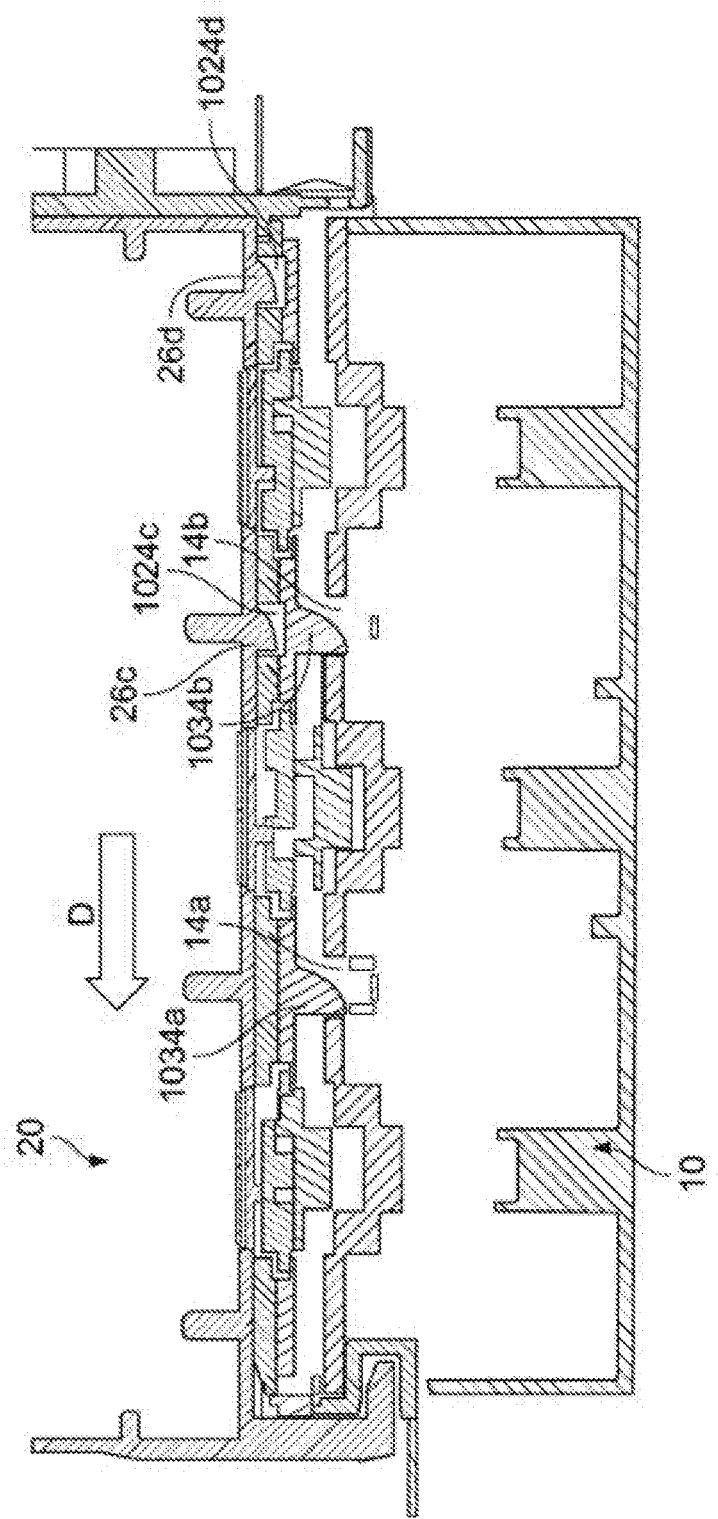
FIG. 10D is an illustrative side cross-sectional view of a tool driver, a sterile adapter with force-transferring abutment features, and a surgical tool.

FIG. 10D illustrates one variation in which the abutments (e.g., ribs) of the plate assembly may resolve or redirect axial forces from the tool to the tool driver. The adapter engagement features 26c and 26d on the surgical tool 20 may engage the tool engagement features 1024c and 1024d (which may be similar to the tool engagement features 944a-944d described above) on the sterile adapter such that the plate assembly receives the axial force delivered by the tool (e.g., forces in the direction of arrow D) via tool engagement features 1024c and 1024d. Movement of the plate assembly is prevented at least in part by the abutment of ribs 1034a and 1034b against receptacles 14a and 14b, which also results transfer of the axial force from the sterile adapter to the tool driver 10. In some variations, at least some of the tool engagement features on the sterile adapter, such as tool engagement features 1024c and 1024d may be aligned with the ribs 1034a and/or 1034b, so as to provide a more direct path for transferring forces from the tool to the tool driver. For example, as shown in FIG. 10D, the tool engagement feature 1024c is aligned with the rib 1034b. In other variations, the tool engagement features need not be aligned with the force-transferring abutments.

Such a transfer of the axial force may, for example, prevent potentially damaging loads from being transferred to the frame 1010 of the sterile adapter 1000. Accordingly, the frame 1010 may advantageously be made smaller and lighter since it does not have to be robust enough to withstand the axial force. Furthermore, in some variations, the force-transferring features in the sterile adapter may result in less compliance or play in the overall tool driver, sterile barrier, and surgical tool assembly, as well as more accurate actuation of the surgical tool by the tool driver (especially when the tool is experiencing force loads).

Springs

Figure 11A:
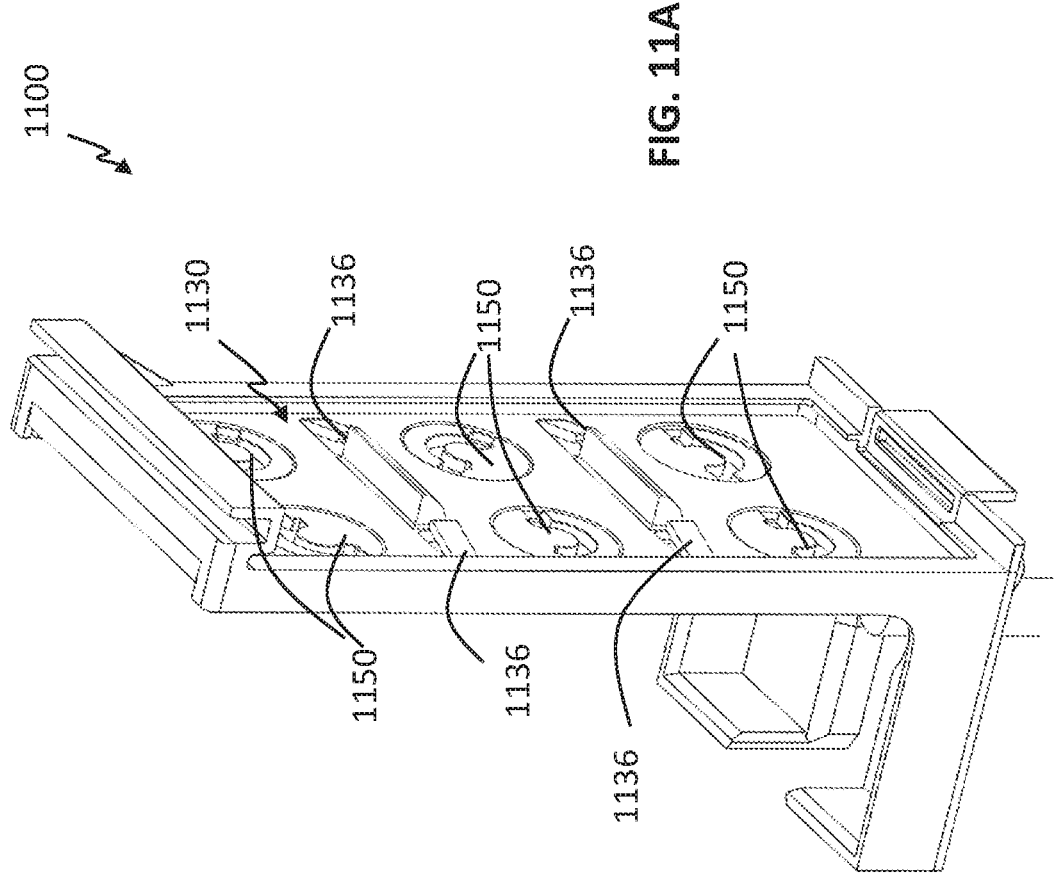
FIG. 11A is a perspective view of one variation of a sterile adapter including a plate assembly with springs.

The plate assembly may, in some variations, include one or more springs configured to urge or bias the plate assembly toward the surgical tool 20 and away from the tool driver 10. For example, as shown in FIG. 11A, a sterile adapter 1100 may include a plate assembly 1130 including a plurality of springs 1136 located on a tool driver-side plate of the plate assembly 1130. The springs 1136 may include, for example, a beam spring, a coil spring, a leaf spring, a compliant material (e.g., an elastomeric material), and/or any suitable mechanism or material that provides a spring force resistant to deformation. In some variations, one or more of the springs 1136 may be integrally formed with the plate assembly 1130 (e.g., through injection molding). As shown in FIG. 11B, when the tool driver 10, the sterile adapter 1100, and the surgical tool 20 are assembled in combination, the springs 1136 may be configured to push off the sterile adapter-facing surface of the tool driver 10 and push the plate assembly 1130 away from the tool driver 10, thereby bringing the plate assembly 1130 closer to the surgical tool 20.

The one or more springs 1136 may, for example, help encourage coupling between the sterile adapter and the surgical tool before the sterile adapter's rotatable couplers 1150 fully engage with the input drive of the surgical tool (not shown), such as to help prevent the surgical tool from separating fully (e.g., falling off) of the sterile adapter. As another example, the spring may help keep the rotatable couplers 1150 positioned within the plate assembly with a clearance gap, so as to avoid frictional ribbing of the couplers 1150 against surfaces of the plate assembly during tool driving. The operation of the one or more springs on the plate assembly is further described below with respect to the sequence of engagement and disengagement of the sterile adapter's rotatable couplers with the tool drive and surgical tool.

Rotatable Couplers

The rotatable couplers (e.g., coupler discs) are supported by the plate assembly as described above. The rotatable couplers are configured to communicate torque from a tool driver to a surgical tool. Each coupler may include, for example, a body (e.g., disc) configured to be interposed between an output drive of the tool driver and an input drive of the surgical tool. The body may include a first face having a first engagement feature configured to engage the output of drive of the tool driver, and may further include a second face having a second engagement feature configured to engage the input drive of the surgical tool. The first and second engagement features may be different in shape. For example, in some variations, the body may include a first face defining a first recess and a second face defining a second recess, where the first recess and the second recess are different in shape. As another example, in some variations, the body may include a first face having a first projection and a second face having a second projection, where the first and second projections are different in shape. In some variations, the body may include a first face having a first arcuate feature (e.g., channel or projection) configured to engage the output drive of the tool driver, and may further include a second face having a second arcuate feature (e.g., channel or projection) configured to engage the input drive of the surgical tool. The first and second arcuate features may have different arc lengths.

Figure 13B:
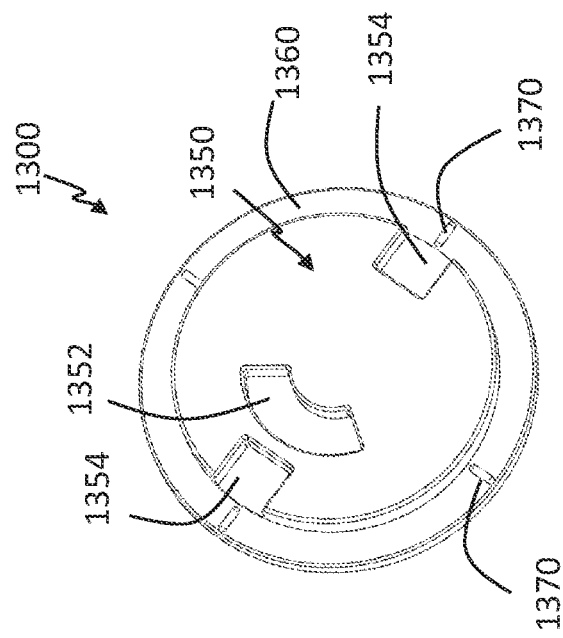
FIGS. 13A and 13B are perspective views of one variation of a rotatable coupler in a sterile adapter.
Figure 13A:
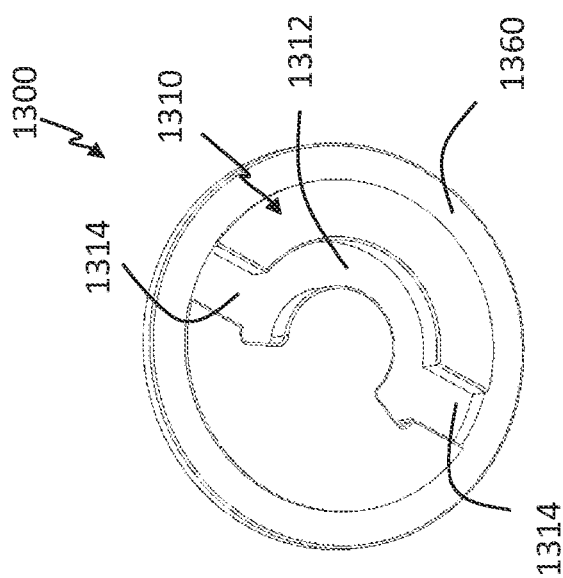

In one exemplary variation, the body may include a tool driver-side face 1310 as shown in FIG. 13A and a tool-side face 1350 as shown in FIG. 13B. The tool driver-side face 1310, as shown in FIG. 13A, may include a first arcuate feature 1312 and one or more first drive features 1314. The tool-side face 1350, as shown in FIG. 13B, may include a second arcuate feature 1352 and one or more second drive features 1354. Each of the first and second arcuate features 1312 and 1352 may, for example, be a circular segment. Furthermore, the first and second arcuate features 1312 and 1352 may be circular segments (e.g., a "C"-shape) that are centered about an axis of rotation of the body. In one variation, the first and second arcuate features 1312 and 1354 are arcuate channels for engaging outward projections on the output drive of the tool driver and the input drive of the surgical tool. However, it should be understood that additionally or alternatively, the tool driver-side face 1310 and/or the tool-side face 1350 may include an outward projection that engages a corresponding arcuate channel on the tool driver output drive or the surgical tool input drive.

Figure 14A:
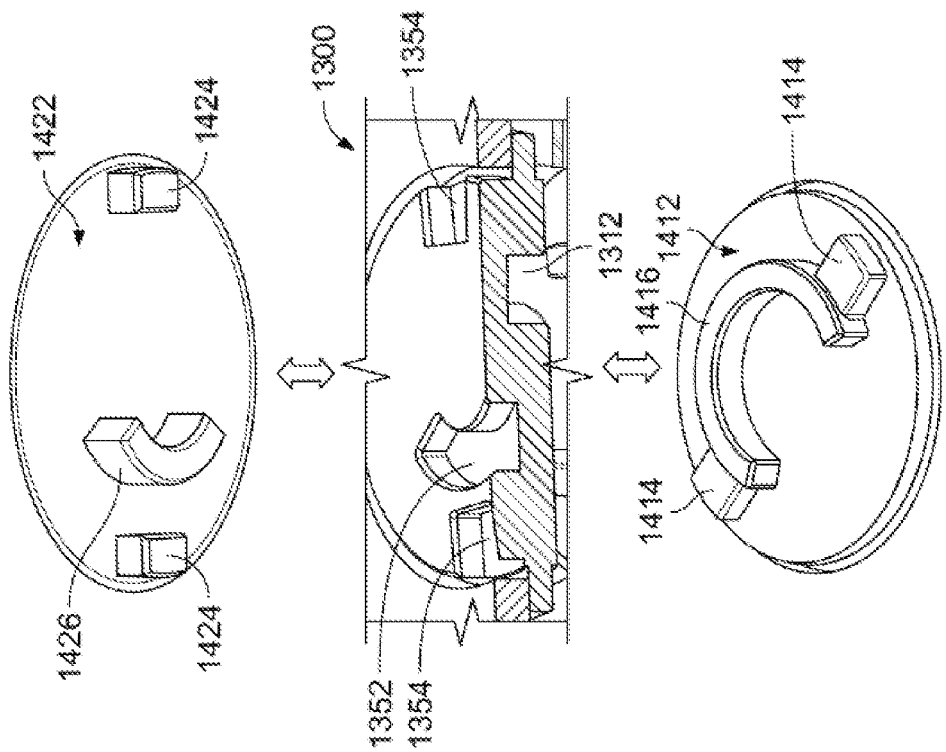
FIG. 14A is an exploded schematic depicting engagement between an output drive of a tool drive, a coupler disc in a sterile adapter, and an input drive of a surgical tool.
Figure 14B:
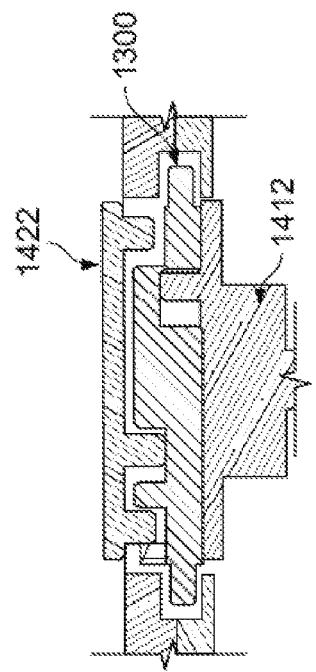
FIG. 14B is a cross-sectional schematic of the engaged combination of the components depicted in FIG. 14A.

The arcuate features 1312 and 1354 rotationally position the rotatable couplers for engagement with the tool driver and the surgical tool. For example, the arcuate features may at least partially function to ensure that there is a single rotational orientation of the rotatable coupler 1300 relative to an output drive of a tool driver and an input drive of a surgical tool. As shown best in FIG. 14A, the first arcuate feature 1312 on the tool driver-side face of the coupler body may be configured to mate with a corresponding arcuate feature 1416 on an output drive 1412 of a tool driver. For example, the coupler arcuate feature 1312 and the output drive arcuate feature 1416 may sweep approximately equal angles such that there is only one relative rotational position in which the coupler arcuate feature 1312 and the output drive arcuate feature 1416 may mate and engage. Similarly, as shown in FIG. 14A, the second arcuate feature 1352 on the tool-side face of the coupler body may be configured to mate with a corresponding arcuate feature 1424 on an input drive 1422 of a surgical tool. For example, the coupler arcuate feature 1252 and the input drive arcuate feature 1426 may sweep approximately equal angles such that there is only one relative rotational position in which the coupler arcuate feature 1352 and the input drive arcuate feature 1426 may mate and engage. When the output drive 1412 is coupled to the input drive 1422 via the rotatable coupler 1300 as described above and shown in the cross-sectional view in FIG. 14B, the rotatable coupler 1300 may communicate torque from the output drive of the tool driver to the input drive of the surgical tool, such that the tool driver actuates or drives the surgical tool.

The first and second arcuate features may have different arc lengths. Furthermore, the sum of the central angle swept by the first arcuate feature 1312 and the central angle swept by the second arcuate feature 1352 may be equal to about 360 degrees, or a full circle. For example, one of the arcuate features on the body (e.g., the first arcuate feature 1312) may sweep a major arc, (i.e., is a major arc more than 180 degrees, such as an angle that is between about 181 degrees and about 270 degrees), while the other arcuate feature (e.g., the second arcuate feature 1354) on the body may sweep a minor arc (i.e., is a minor arc less than 180 degrees, such as an angle that is between about 90 degrees and about 179 degrees). In variations in which one of the first arcuate feature 1312 or the second arcuate feature 1352 sweeps a major arc that is more than 180 degrees and the other sweeps a minor arc that is less than 180 degrees, the first and second arcuate features may help maintain in-plane rotation of the coupler 1300 during driving. For example, with reference to FIG. 14A, when the output drive arcuate feature 1416 is received in the first coupler arcuate feature 1312 and the input drive arcuate feature 1426 is received in the second coupler arcuate feature 1352, the output drive disc 1412 and input drive disc 1422 may be substantially prevented from tilting or leaning toward each other, due at least in part to physical interference between output drive arcuate feature 1416 and the input drive arcuate feature 1426 through the intervening surfaces of the coupler disc 1300 arcuate features. Thus, the coupler 1300 may maintain substantial co-planar motion (e.g., without precession), which also helps keep the output drive disc 1412 and the input drive disc 1422 substantially parallel, thereby improving accuracy of actuation of the surgical tool.

The tool driver-side face 1310 may further include one or more first drive features 1314 as shown in FIG. 13A, and the tool-side face 1350 may further include one or more second drive features 1354 as shown in FIG. 13B. The drive features 1314 and 1354 may include, for example, pin holes or recesses (square, round, etc.) configured to engage with outward projecting drive pins on the output drive of the tool driver and on the input drive of the surgical tool. However, it should be understood that additionally or alternatively, the tool driver-side face 1310 and/or the tool-side face 1350 may include an outward projecting drive pin that engages a corresponding hole or recess on the tool driver output drive or the surgical tool input drive. Furthermore, the drive features 1314 and 1354 may include chamfers to help guide engagement with corresponding drive features on the tool driver and/or surgical tool. In one variation, the body includes two drive features 1314 on its tool driver-side face arranged about 180 degrees from one another, and two drive features 1354 on its tool-side face arranged about 180 degrees from another. The set of the two drive features 1314 and the set of the two drive features 1354 may be rotationally offset by about 90 degrees (e.g., a first drive feature 1314 located at about 0 degrees, a second drive feature 1354 located at about 90 degrees, another first drive feature 1314 located at about 180 degrees, and another second drive feature 1354 located at about 270 degrees). A rotational offset of about 90 degrees may, in some variations, permit and help compensate for axial misalignment between the output drive of the tool driver and the input drive of the surgical tool (e.g., operating similarly to a floating disc in an Oldham coupler). Furthermore, the first drive features 1314 may, in some variations, be equidistant from the axis of rotation of the coupler 1300, and similarly the second drive features 1354 may be equidistant from the axis of rotation of the coupler.

The first and second drive features 1314 and 1354 may be disposed near the edge or perimeter of the coupler body, so as to maximize torque transferred from the tool driver to the surgical tool through the coupler 1300. For example, with reference to FIG. 14A, the first drive features 1314 (not shown in FIG. 14A) on the coupler 1300 may be configured to receive the output drive pins 1414 on the output drive 1412. The second drive features 1354 on the coupler 1300 may be configured to receive the input drive pins 1424 on the input drive 1422. Accordingly, when the output drive 1412 is coupled to the input drive 1422 via the rotatable coupler 1300 as shown in the cross-sectional view in FIG. 14B, the rotatable coupler 1300 may communicate torque from the output drive of the tool driver to the input drive of the surgical tool, such that the tool driver actuates or drives the surgical tool. Although the drive features 1314 and 1354 on the coupler 1300 may be the primary features for communicating torque, the arcuate features 1312 and 1352 on the coupler 1300 may also communicate some amount of torque by virtue of also engaging with the output drive of the tool driver and the input drive of the surgical tool.

As shown in FIGS. 13A and 13B, the coupler body may further include an outer flange 1360 that helps retain and/or position the coupler 1300 within the plate assembly. The outer flange 1360 may be substantially continuous around the perimeter of the coupler body, though alternatively may include discrete segments (e.g., tabs) distributed around the perimeter of the coupler body. Furthermore, the outer flange 1360 may include one or more frictional features, such as on the tool-side face 1350 of the outer flange 1360, that may help reduce the amount of free spin of the coupler 1300 within the plate assembly when desired (e.g., during selected parts of the coupling process in which the coupler 1300 engages the surgical tool, as described in further detail below). In some variations, the tool driver-side face 1310 of the outer flange 1360 may additionally or alternatively include one or more frictional features. Examples of frictional features include raised bumps 1370 as shown in FIG. 13B, a wavy or undulating outer flange profile, an elastomeric or other high friction material (e.g., pads, co-injected, overmolded, etc.) on the outer flange 1360, etc.

Figure 16D:
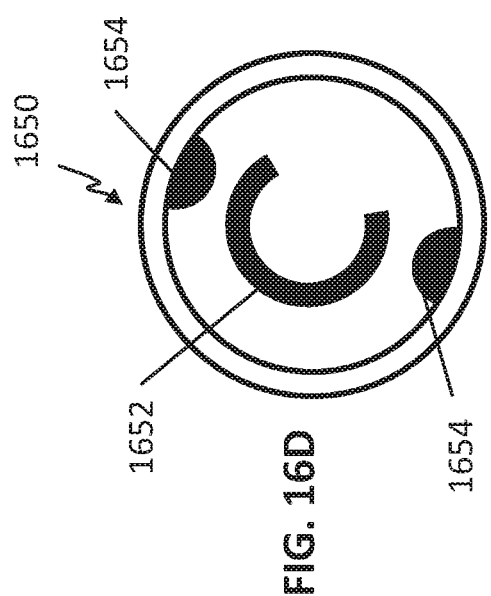
FIGS. 16B, 16C and 16D are side, bottom and top views, respectively, of the rotatable coupler variation depicted in FIG. 16A.
Figure 16C:
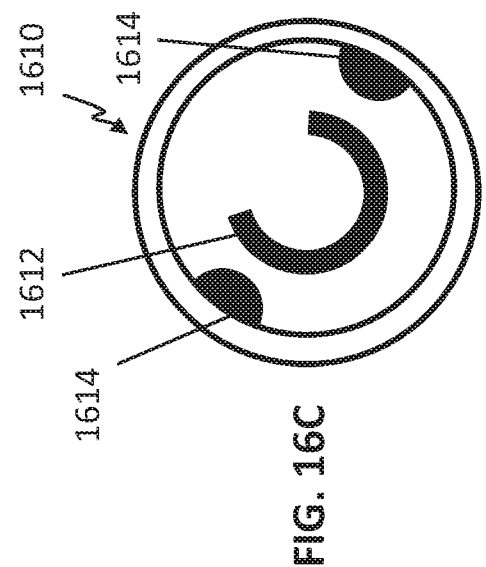
Figure 16A:
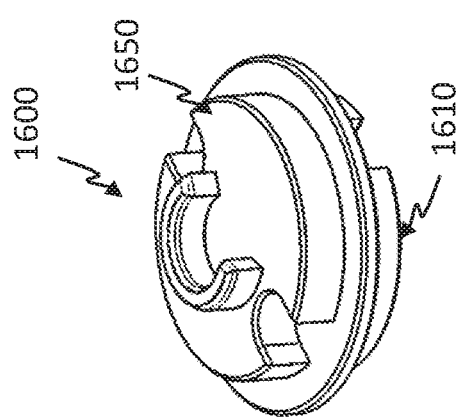
FIG. 16A is a perspective view and a side view, respectively, of another variation of a rotatable coupler in a sterile adapter.
Figure 16B:
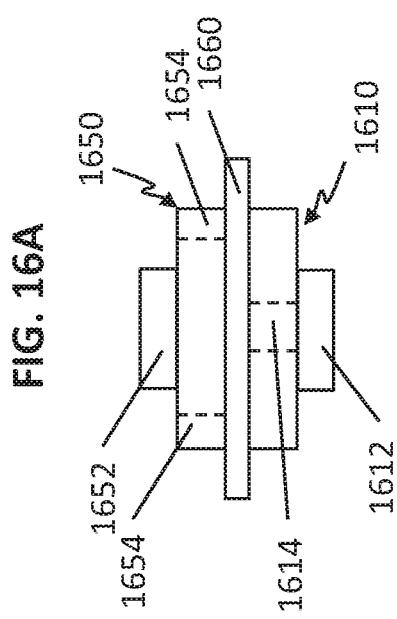

As shown in FIGS. 16A and 16B, another exemplary variation of a rotatable coupler 1600 in a sterile adapter (e.g., for placement in a shifting plate assembly) may include a first coupler portion 1610 configured to engage an output drive of a tool driver and a second coupler portion 1650 configured to engage an input drive of a surgical tool. First and second coupler portions 1610 and 1650 may be separate pieces that are coupled or affixed together (e.g., with epoxy or other suitable adhesive, thermal molding, press-fit of pins or other joining features, etc.). Alternatively, first and second coupler portions 1610 and 1650 may be integrally formed, such as through injection molding or being machined as one piece.

Similar to the rotatable coupler 1300 described above with reference to FIGS. 13A and 13B, the rotatable coupler 1600 may incorporate one or more arcuate features (e.g., at least one recess and/or outward projection sweeping a major arc, or appearing in a "C"-shape) to provide a single rotational alignment relative to an output drive disc on a tool drive and relative to an input drive disc on a surgical tool. The arcuate features may also help keep the coupler 1600 rotating in substantially a single plane. Additionally, similar to the rotatable coupler 1300, the rotatable coupler 1600 may incorporate drive features (e.g., pins located as far as possible from a central axis of rotation of the coupler body) to communicate driving torque from an output drive on a tool drive to an input drive on a surgical tool. Furthermore, like the rotatable coupler 1300, the rotatable coupler 1600 may include an outer flange 1660 configured to help retain and position the rotatable coupler 1600 within a plate assembly.

For example, FIG. 16C depicts a tool driver-side face (i.e., configured to face and engage the tool driver) of the first coupler portion 1610. The tool driver-side face of the first coupler portion 1610 may include an arcuate feature 1612 configured to engage with a corresponding arcuate feature on a tool driver (not shown) and drive features 1614 (e.g., holes) configured to engage with corresponding drive features (e.g., pins) on the tool driver. Furthermore, FIG. 16D depicts a tool-side face (i.e., configured to face and engage the surgical tool) of the second coupler portion 1650. The tool-side face of the second coupler portion 1650 may include an arcuate feature 1652 configured to engage with a corresponding arcuate feature on a surgical tool (not shown) and drive features 1654 (e.g., holes) configured to engage with corresponding drive features (e.g., pins) on the surgical tool.

In some variations, the first coupler portion's drive features 1614 may be offset about 90 degrees from the second coupler portion's drive features 1654. For example, the first and second coupler portions 1610 and 1650 may be different instances of the same design (e.g., same size and shape) but rotated and affixed to one another with an approximately 90-degree rotational offset. This rotational offset may permit and help compensate for axial misalignment between the output drive of the tool driver and the input drive of the surgical tool (e.g., operating similarly to a floating disc in an Oldham coupler). At least some of the drive features on the coupler 1600 may be elongated or slot-like, which may provide some tolerance accommodation and compensation for axial misalignment between the output drive of the tool driver and the input drive of the surgical tool. For example, the drive features 1614 on the first coupler portion 1610 may be somewhat elliptical to enable the coupler 1600 to translate around a circular drive pin on the tool driver as the coupler 1600 rotates, while additionally the drive features 1654 on the second coupler portion 1650 may be somewhat elliptical to enable the coupler 1600 to translate around a circular drive pin on the surgical tool. Thus, the drive features 1614 and 1654 may be able to compensate for axial misalignment.

Another exemplary variation of a rotatable coupler 2550 in a sterile adapter (e.g., for placement in a shifting plate assembly) is shown in the sterile adapter 2500 depicted in FIGS. 25E and 25F. A first face (e.g., tool driver-side face) of the rotatable coupler 2550 is shown in FIG. 25E, while a second face (e.g., tool-side face) of the rotatable coupler 2550 is shown in FIG. 25F. Furthermore, the rotatable coupler 2550 may include an outer flange 2560 similar to the outer flange 1360 described above with respect to FIGS. 13A and 13B. As shown in FIG. 25G, one or more rotatable couplers 2550 may be supported by a plate assembly 2530 in a frame 2510, similar to that described elsewhere herein.

As shown in FIG. 25E, the first face of the rotatable coupler may include at least one engagement feature 2562 for engaging with an output drive of a tool driver. The engagement feature 2562 may include a central feature (e.g., recess or projection) that is substantially centered on an axis of rotation of the rotatable coupler. As shown in FIG. 25F, the second face of the rotatable coupler 2500 may include at least one engagement feature 2564. The engagement feature 2564 may include an arcuate feature (e.g., recess or projection, such as an arcuate channel or arcuate projection) similar to those described above with respect to couplers 1300 and 1600. As shown in FIG. 25F, the second face of the rotatable coupler 2500 may include two engagement features 2564 and 2564' (e.g., one engagement feature disposed on each side of a drive feature 2574, described below). In other variations, the rotatable coupler 2500 may include any suitable number of engagement features on the first side and/or second side of the coupler 2500.

In some variations, the engagement features 2562 and 2564 may extend in opposite axial directions. For example, as shown best in the perspective views of FIGS. 25A and 25B, both of the engagement features 2562 and 2564 may be recesses (e.g., channels) that extend inwards in opposite directions in the rotatable coupler. Alternatively, the engagements features 2562 and 2564 may be projections (e.g., ridges) that extend outwards in opposite directions in the rotatable coupler.

In some variations, the coupler 2550 may include one or more drive features (e.g., similar to drive features described above for coupler 1300 and coupler 1600). For example, similar to coupler 1300, the tool driver-side face of coupler 2550 shown in FIG. 25E may include one or more first drive features 2572 (e.g., cutouts), and the tool-side face of coupler 2550 shown in FIG. 25F may include one or more second drive features 2574 (e.g., cutouts). The set of the drive features 2572 and the set of the drive features 2574 may be rotationally offset by about 90 degrees, similar to that described above with respect to coupler 1300. However, the drive features may be sized, shaped, and arranged in any suitable manner.

The rotatable couplers (e.g., coupler 1300, coupler 1600, coupler 2550) may include polycarbonate, ABS, other materials described above for the frame and/or plate assembly, or other suitable rigid material which may be injection molded, machined, extruded, stamped, 3D printed, or manufactured in any suitable manner.

Sterile Adapter Coupling and Decoupling

Figure 15A:
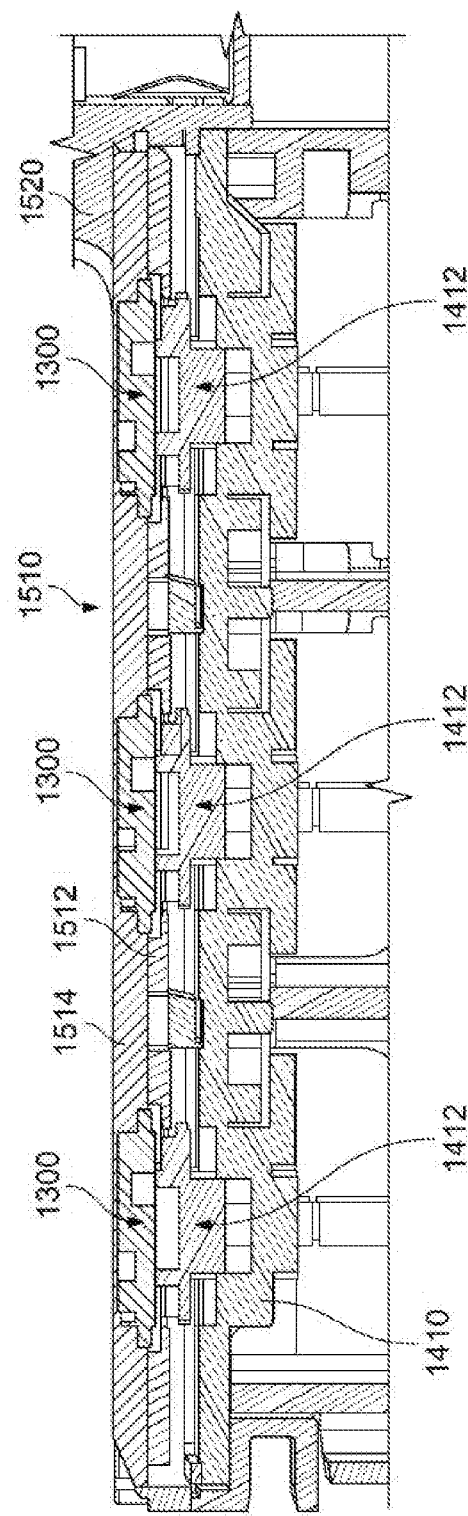
FIGS. 15A-15G are illustrative schematics of an exemplary process of coupling a tool driver to one variation of a sterile barrier, and coupling the sterile barrier to a surgical tool.

An exemplary method for coupling and engaging the sterile adapter described above to a tool driver and/or tool drive is generally depicted in FIGS. 15A-15G. As shown in FIG. 15A, a sterile adapter may include a frame 1520 that houses a plate assembly 1510. The plate assembly 1510 may include a tool driver-side plate 1512 and a tool-side plate 1514, and the plate assembly may support one or more rotatable couplers or coupler discs 1300 disposed between the plates 1512 and 1514 with suitable axial and rotational clearance. Furthermore, a tool driver 1410 may include one or more output drive discs 1412 configured to mate and engage with one or more corresponding coupler discs 1300.

Figure 15B:
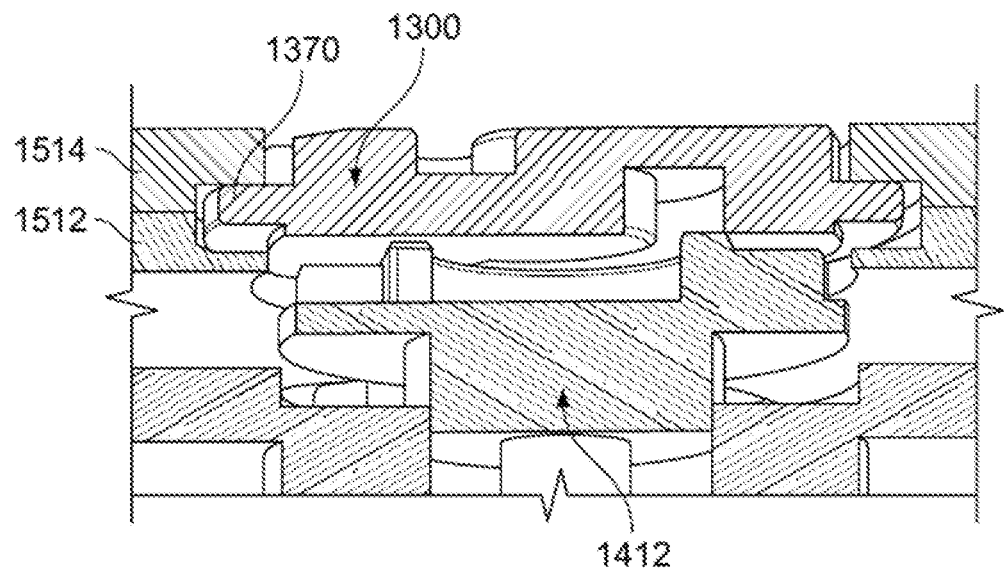
Figure 15C:
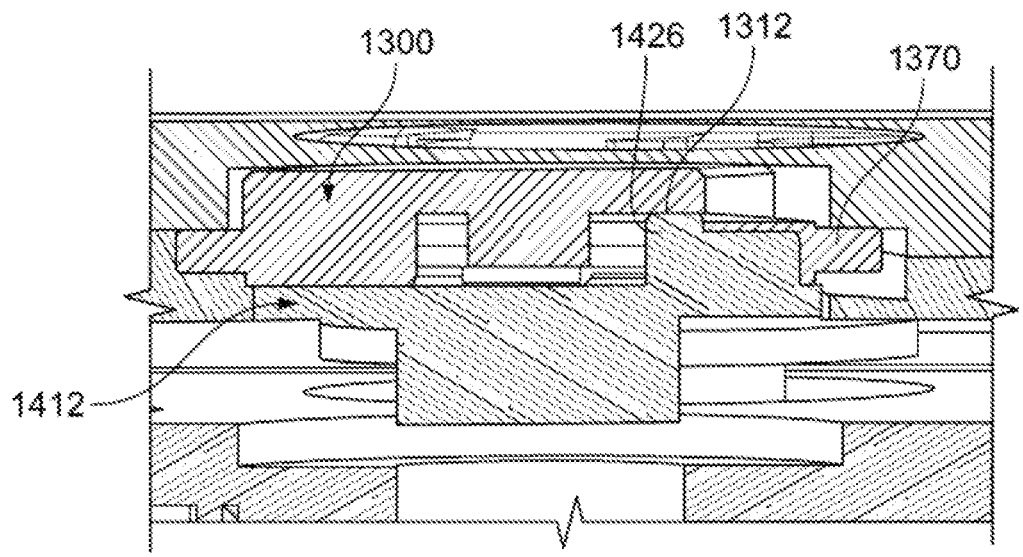

In FIG. 15A, the frame 1520 is attached to the tool driver 1410, but as shown in more detail in FIG. 15B, the output drive discs 1412 are not yet engaged with the coupler discs 1300. As shown in FIG. 15B, the output drive disc 1412 is biased upward against the coupler disc 1300 due to a biasing force (e.g., provided by a spring in the tool driver that spring-loads the output drive disc 1412, and/or at least one magnet that causes an attraction between the output drive disc 1412 and the coupler disc 1300). The coupler disc 1300 is also urged upward, with its movement limited by the outer flange 1370 of the coupler disc 1300 being constrained by the tool-side plate 1514.

Following attachment of the frame 1520 to the tool driver 1410, the output drive disc 1412 rotates (e.g., by actuating a motor coupled to the output drive disc 1412) until its arcuate feature 1426 is rotationally aligned with the coupler disc arcuate feature 1312. Despite some amount of frictional contact between the output drive disc 1412 and the coupler disc 1300 that may tend to cause the discs 1412 and 1300 to move together, the frictional features on the outer flange 1360 may substantially prevent the coupler disc 1300 from rotating along with (e.g., in tandem with) the output drive disc 1412 as the output drive disc rotates. For example, frictional features (e.g., raised bumps 1360 as described above with reference to FIG. 13B) that rub against the tool-side plate 1514 may substantially prevent the coupler disc 1300 from rotating while the output drive disc 1412 rotates in an effort to achieve rotational alignment with the coupler disc 1300. For example, a processor may be coupled to the tool driver and configured to control one or more output drive discs 1412 (simultaneously, individually in sequence, pairwise, etc.) to rotate until they are rotationally aligned and engaged with their corresponding rotatable coupler discs 1300. In some variations, rotational alignment may be achieved by driving the output drive discs 1412 until each has rotated at least a predetermined angle or number of rotations (e.g., 1, 1.5, 2, 2.5, 3, etc.) or a predetermined period of time. At some point during a threshold angle or number of rotations, each moving output drive disc 1412 will be rotationally aligned with the substantially static rotatable coupler disc 1300. Additionally or alternatively, rotational alignment may be determined, for example, with sensors (capacitive, etc.) located on one or both of the interfacing sides of the output drive discs and the rotatable coupler discs 1300 such that intimate, adjacent contact between the output drive discs and the rotatable coupler discs is detected. As yet another example, rotational alignment may be detected based on reaction torque measured by one or more sensors in the tool driver when a output drive disc 1412 becomes engaged with its corresponding coupler disc 1300. Once this rotational alignment is achieved, the arcuate feature 1416 engages the coupler disc arcuate feature 1312 (and drive pins of the output drive disc 1412 also engage the drive features of the coupler disc 1300), at least in part because the output drive disc 1412 is biased against the coupler disc 1300.

Figure 15D:
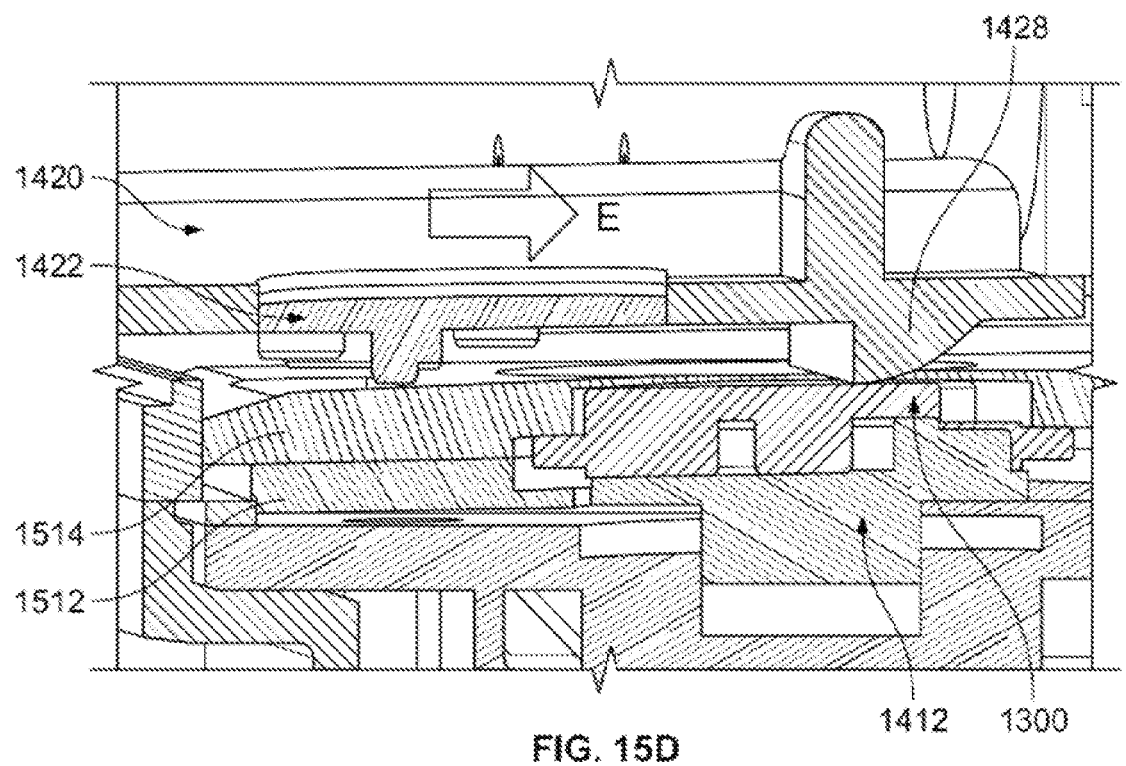

In FIG. 15D, a surgical tool 1420 is being attached to the sterile adapter (e.g., the frame and/or the plate assembly) by moving along the sterile adapter in the direction shown by arrow E. The surgical tool 1420 couples to the sterile adapter when all adapter engagement features 1428 on the tool (e.g., a rib similar to ribs 26a-26d described above with reference to FIG. 9B) engage with all corresponding tool engagement features 1515 on the plate assembly, as partially shown in FIG. 15E.

Figure 15E:
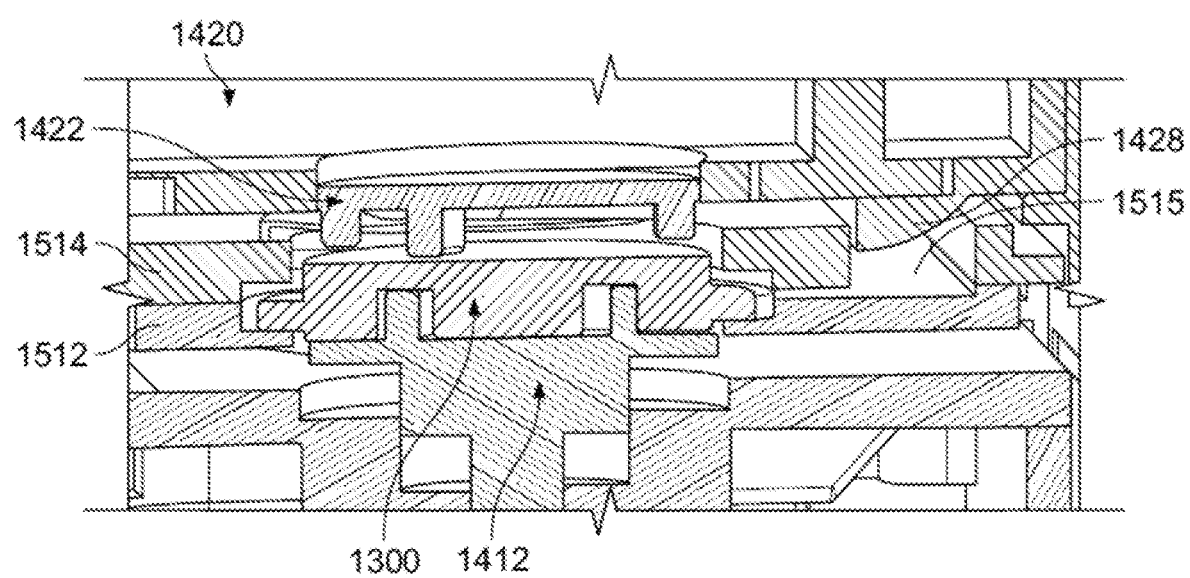

As shown in FIG. 15E, the output drive disc 1412 and coupler disc 1300 are still engaged. Input drive discs 1422 on the surgical tool are not yet engaged with the coupler discs 1300 and thus tend to push coupler discs 1300 and the plate assembly downward due to non-engagement. To provide a counter force, the shifting plate assembly (including plates 1512 and 1514) is biased upwards against the surgical tool 1420 by one or more springs on the shifting plate assembly (e.g., spring 1136 as described above with reference to FIGS. 11A and 11B), thereby causing the coupler disc 1300 to be pressed against the tool drive-side plate 1512 and creating upper clearance between the coupler disc 1300 and the input drive disc 1422 of the tool. Furthermore, the springs on the shifting plate assembly encourage engagement of the plate assembly to one or more adapter engagement features 1428 on the tool, thereby helping to prevent the surgical tool 1420 from falling off of the sterile adapter.

Figure 15F:
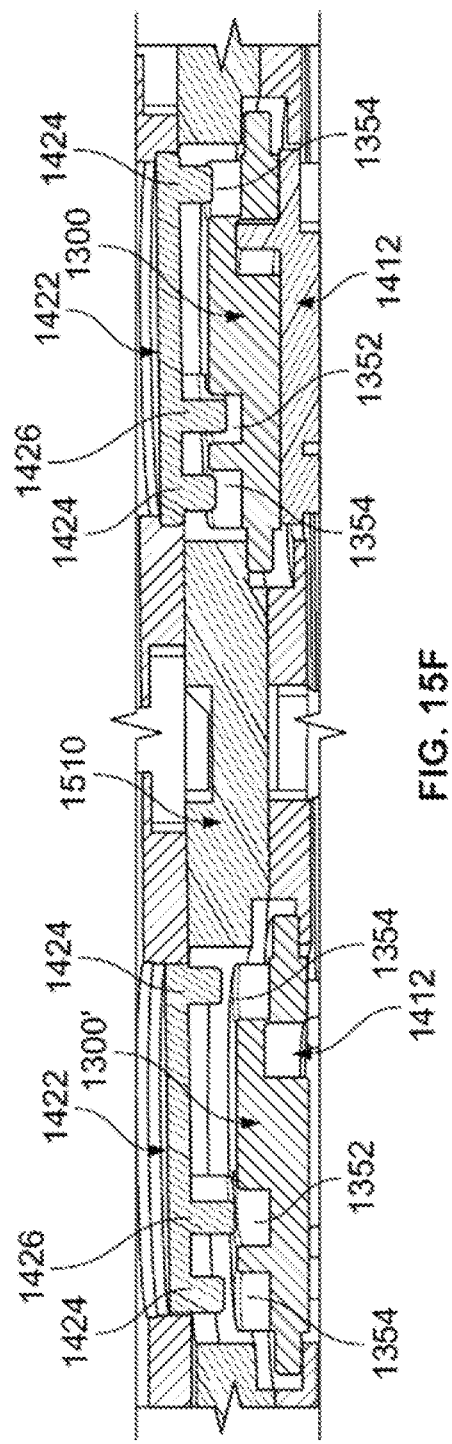

Following attachment of the surgical tool 1420 to the sterile adapter, the coupler discs 1300 may rotate (simultaneously or individually in sequence, etc.) via rotation of the output drive discs 1412 in an effort to achieve rotational alignment with corresponding input drive discs 1422 on the surgical tool. Rotational alignment between the coupler discs 1300 and the corresponding input drive discs 1422 may be brought about and/or detected, for example, in the same or similar manner as rotational alignment between the output drive discs 1412 and the coupler discs 1300 described above. Such rotational alignment is achieved when all arcuate features 1426 on the tool input drive discs 1422 are aligned with corresponding arcuate features 1352 on the coupler disc 1300 (and drive pins 1424 on the input drive disc 1422 are aligned with drive features 1354 on the coupler discs 1300). Before this stage, any rotational misalignment between a coupler disc 1300 and a corresponding input drive disc 1422 will tend to push coupler discs 1300 and the plate assembly downward. For example, as shown in FIG. 15F, the coupler disc 1300' depicted on the left is not yet rotationally aligned with its corresponding input drive disc 1422, while the coupler disc 1300 depicted on the right is rotationally aligned with its corresponding input drive disc 1422.

Figure 15G:
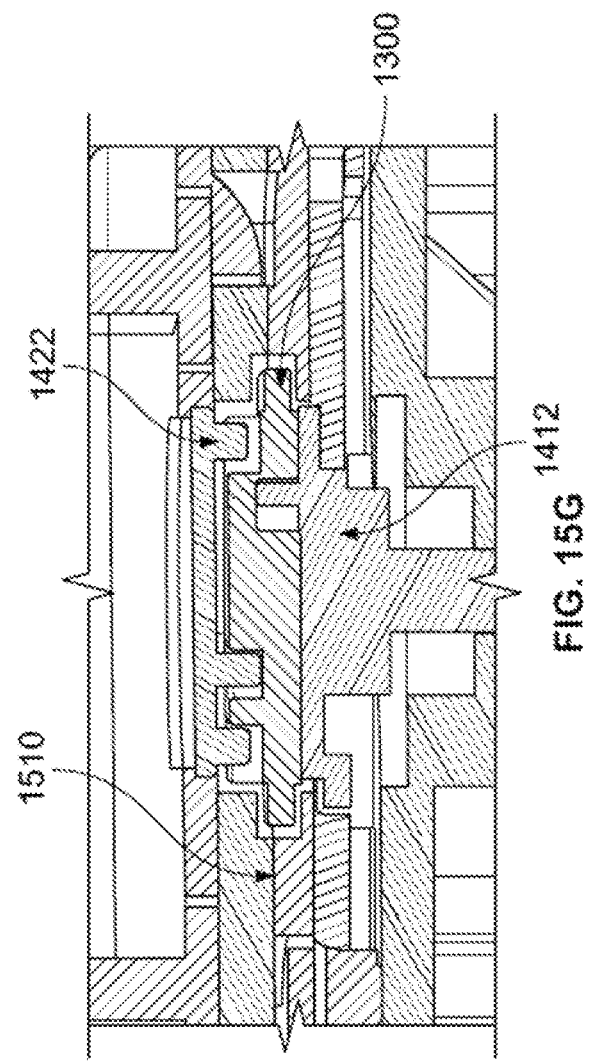

When all coupling discs 1300 are rotationally aligned with corresponding input drive discs 1422, then coupling discs 1300 become engaged with the output drive discs 1412 on the tool driver and engaged with the input drive discs 1422 on the surgical tool, as shown in the arrangement shown in FIG. 15G. Furthermore, the biasing springs on the plate assembly 1510 push the plate assembly 1510 upwards against the tool. As a result, the coupler disc 1300 is generally centered within the plate assembly 1510, where it has upper and lower clearance to rotate within the plate assembly freely (e.g., such that the friction bumps on the outer flange of the coupler disc do not contact any surface).

Accordingly, the coupling discs 1300 are ready to communicate torque from the output drive discs 1412 to the input drive discs 1422, across the sterile barrier which the sterile adapter is part of.

To decouple the surgical tool from the sterile adapter, a latch (e.g., a lever mechanism or button) on the surgical tool may function to depress or push down the shifting plate assembly away from the surgical tool. When the shifting plate assembly is sufficiently depressed, the coupling discs 1300 become separated and disengage from the input drive discs 1422 of the surgical tool, thereby allowing the surgical tool to be removed from the sterile adapter. Furthermore, the sterile adapter frame may be delatched (e.g., disengaging a locking mechanism such as the locking mechanism 630 described above with reference to FIG. 6A or locking mechanism 630' described above with reference to FIG. 6C) from the tool drive, then lifted to separate and disengage the coupling discs 1300 from the output drive discs 1412 of the tool drive, thereby allowing the sterile adapter to be removed from the surgical tool.

Coupling and Decoupling Variations

In some variations, the sterile adapter may additionally or alternatively include a removable film to help orient the rotatable couplers in the sterile adapter, such as when engaging the output drive discs in the tool driver with the rotatable couplers in the sterile adapter. For example, the coupler discs on the sterile adapter may be pre-aligned with a removable film before and during attachment of the frame to the tool driver. For example, as shown in FIG. 17A, a sterile adapter 1700 may include a removable film 1702 on a tool-side of the sterile adapter that adheres to the coupler discs 1710 and keeps the coupler disc drive features 1712 in a predetermined orientation. Before attaching the sterile adapter 1700 to the tool driver 1720, the output drive discs 1722 may be rotated (e.g., by actuating the motors coupled to the output drive discs 1722) to a predetermined orientation. For example, the output drive discs 1722 may be rotated to be in-line with a longitudinal or axial direction along the tool as shown in FIG. 17B, and/or rotated to correspond to the predetermined orientation of the coupler discs 1710. Upon attaching the sterile barrier 1700 to the tool driver 1720, the removable film 1702 may keep the coupler discs 1712 substantially stationary such that the output drive discs 1722 may be rotated to seek rotational alignment with the coupler discs 1712. Once rotational alignment is achieved, the removable film 1702 may be removed (e.g., peeled off, rubbed off, scratched off, etc.) as shown in FIG. 17C. The removable film 1702 may include, for example, polyurethane, polyethylene terephthalate (PET), and/or any suitable material attachable with a pressure-sensitive adhesive or other suitable adhesive. In some variations, the removable film 1702 may also function as protection for the sterile adapter, such as during transport or storage.

In some variations, the coupling of a surgical tool to a sterile adapter may involve selectively exposing the sterile adapter's rotatable couplers for coupling and selectively covering them for decoupling from the surgical tool) due to a latch on or actuatable by the surgical tool. For example, in one variation as shown in FIG. 18A, a surgical tool 1730 may include at least one lever 1732 that is actuatable (e.g., by pinching levers on both sides of the surgical tool 1730). As shown in FIG. 18D, when the levers 1732 are depressed inwards, lever arms 1734 are configured to push down and displace at least the sterile adapter's rotatable couplers 1710. Accordingly, when the surgical tool 1730 is sliding over the sterile adapter as shown in FIG. 18B, the levers 1732 may be depressed inwards to substantially prevent engagement between the rotatable couplers 1710 and the input drives of the tool driver (not shown). As shown in FIG. 18C, when the surgical tool 1730 is sufficiently seated in the sterile adapter, the levers 1732 may be released, thereby moving the lever arms 1734 away from the sterile adapter 1700 and allowing the sterile adapter's rotatable couplers 1710 (biased upwards as described above, such as with springs or magnets) to move upwards and engage with the input drives of the surgical tool. Furthermore, each levers 1732 may include at least one lever foot 1736 configured to rest in a lateral cutout 1706 (shown in FIG. 18B) in the sterile adapter 1700 in order to continue permitting the rotatable couplers 1710 to be biased upwards, thereby maintaining tool input drive engagement with the sterile adapter's rotatable couplers 1710.

The surgical tool 1730 may be decoupled from the sterile adapter 1700 by reversing the coupling process described above. For example, as shown in FIG. 19A, the levers 1732 may be depressed inwards, thereby moving the lever arms 1734 (not pictured) to push down and displace the sterile adapter's rotatable couplers 1710 (not pictured). The displacement of the rotatable couplers 1710 causes the input drives of the tool 1730 to disengage from the sterile adapter, which permits the surgical tool 1730 to be withdrawn as shown in FIG. 19B.

FIGS. 20A and 20B illustrate another variation for selectively exposing and hiding the sterile adapter's rotatable couplers due to a latch on or actuatable by the surgical tool. As shown in FIG. 20A, a sterile adapter 2000 may include a shifting plate 2022 that is spring-loaded to be biased upward toward the surgical tool 2030. The shifting plate 2022 may be restrained against the spring load by a locking lever 2020 in an engaged position such that the shifting plate 2022 restrains the rotatable coupler 2010 in a retracted position, which is also spring-loaded and biased upward toward the surgical tool 2030. While the lever is in the position shown in FIG. 20A and the rotatable coupler 2010 is retracted or hidden, the rotatable coupler 2010 is not able to engage with the input drive disc 2032 of the surgical tool 2030. The surgical tool may approach being seated in the sterile adapter 200 (e.g., moved in the direction of the arrow F) until it encounters locking lever 2020. Locking lever 2020 pivots to a disengaged position as shown in FIG. 20B, thereby releasing the biased shifting plate 2022. The shifting plate 2022 is biased to move upward toward the surgical tool, thereby allowing the rotatable coupler 2010 to also extend upward toward the surgical tool 2030 and engage the input drive disc 2032. Upon engagement of the rotatable coupler 2010 and the input drive disc 2032, the rotatable coupler 2010 may be driven and communicate torque to the surgical tool 2030.

The surgical tool 2030 may be decoupled from the sterile adapter 2000 by reversing the coupling process described above. For example, a latch mechanism (not shown) may push down on a shifting plate member 2024 until the locking lever 2020 is restored its engaged position shown in FIG. 20A, whereupon the locking lever 2020 restrains the shifting plate 2022 and again retracts the rotatable coupler 2010. Upon retraction of the rotatable coupler 2010, the rotatable coupler 2010 is decoupled from the surgical tool 2030 so that the surgical tool 2030 may be removed.

Axially Shifting Plate Assembly Variation

In another variation as shown in FIGS. 21A-21C, a sterile adapter 2100 may include a plate 2110 having a tool-side face configured to couple to a surgical tool 2150. The plate 2110 may include one or more alignment features for facilitating the coupling and engagement of the surgical tool 2150. For example, as shown in FIG. 21A, the plate 2110 may include a female guide 2114 (e.g., one or more longitudinal rail pairs) configured to engage a male guide 2156 (FIG. 21B) (e.g., a longitudinally-directed projection) or other guiding feature on the surgical tool 2150 to help center the surgical tool 2150 as it is seated onto the sterile adapter 2100 as shown in FIG. 21C. As shown in FIG. 2B, a leading end of the male guide 2156 may be tapered to facilitate a gradual centering or alignment with the female guide 2114 as the surgical tool 2150 is attached to the sterile adapter 2100. Additionally or alternatively, the plate 2110 may include a male feature that projects outwardly and the surgical tool may include a female guide configured to receive the male guide on the plate 2110. As another example, as shown in FIG. 21A, the plate 2110 may include one or more magnets 2112 on the tool-side face that is configured to magnetically attract a magnetic component 2156 on the surgical tool 2150. For example, the plate may include a magnet 2112 generally along a centerline of the plate 2110 projection 2156 (FIG. 21B) that is configured to attract and thereby center a centrally-placed magnetic component on the surgical tool 2150 (e.g., the male guide 2156, which may include a ferromagnetic material) or other magnet component coupled to a centerline of the surgical tool 2150.

Figures 22A, 22B:
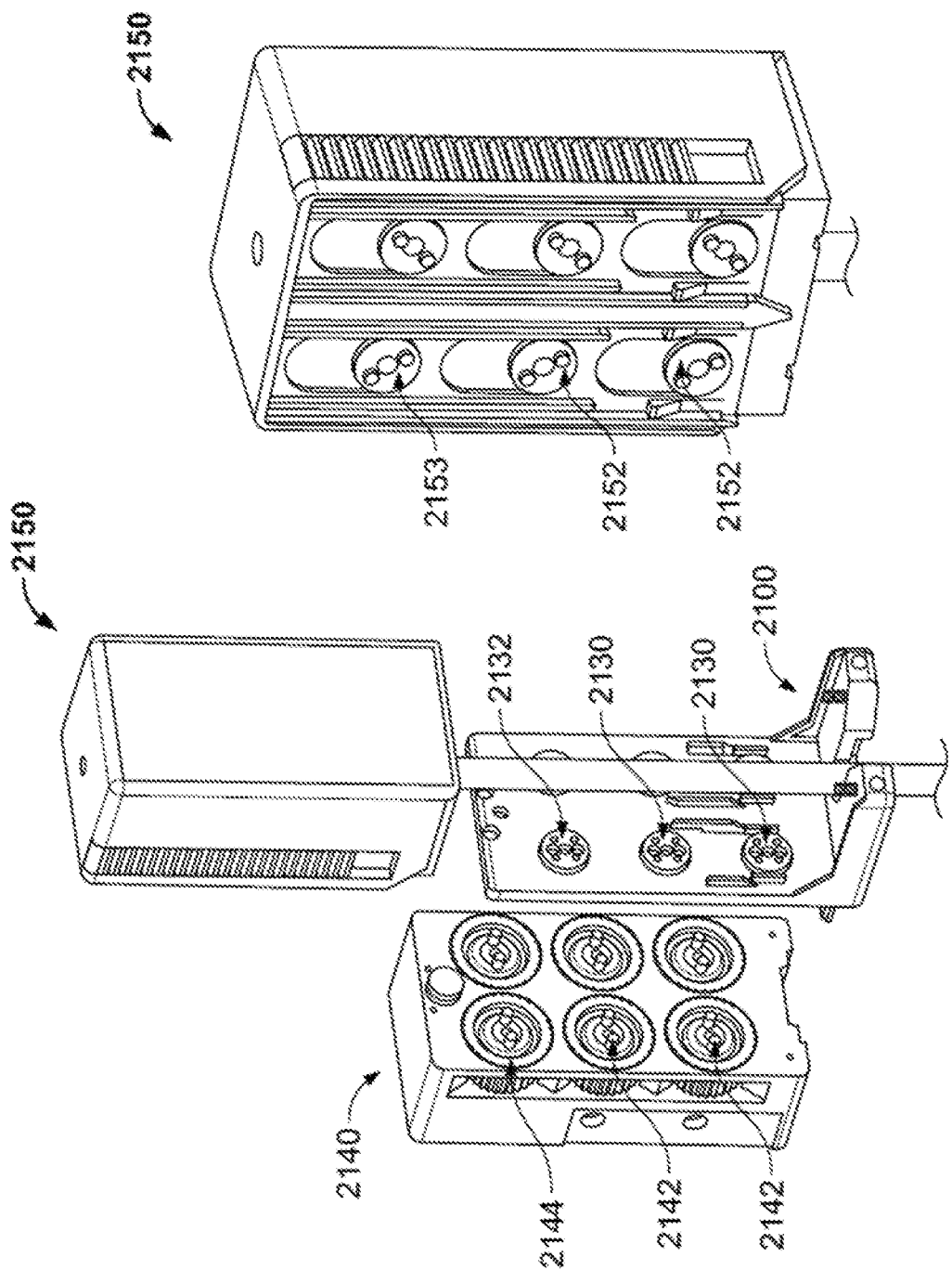
FIG. 22A is a perspective view of one variation of a sterile adapter with drive couplers configured to be magnetically attracted to one variation of a tool driver.
FIG. 22B is a perspective view of one variation of a surgical tool configured to be magnetically attracted to the sterile adapter depicted in FIG. 22A.

As shown in FIGS. 22A and 22B, magnetic and/or ferromagnetic material components may further be included in one or more output drives 2142 of the tool driver 2140, in one or more rotatable couplers 2130 in the tool driver 2100, and/or one or more input drives 2152 in the surgical tool 2150, including a suitable combination of magnetically attractive and/or magnetically repulsive materials or components, in order to encourage self-alignment of mating components. For example, at least one output drive 2142 on the tool driver 2140 may include one or more magnets 2144, and at least one corresponding coupler 2130 in the sterile adapter 2100 may include one or more magnets 2132. The magnet 2144 may attract the magnet 2132, thereby urging self-alignment and engagement of the output drive 2142 and the coupler 2130. As another example, at least one input drive 2152 on the surgical tool 2150 may include one or more magnets 2153. Magnet 2132 on the sterile adapter coupler may attract the magnet 2153 on the surgical tool input drive, thereby similarly urging self-alignment and engagement of the coupler 2130 and the input drive 2152.

In some variations, as shown in FIG. 23A, the sterile adapter 2100 may include a shifting plate 2120 configured to shift axially in-plane (e.g., in a longitudinal direction along the direction of the tool shaft of the surgical tool), where the shifting plate 2120 is configured to selectively permit extension and retraction of the rotatable couplers 2130 in the sterile adapter. For example, the shifting plate 2120 may include slots that are configured to enable translation of the shifting plate 2120 around the output drives 2120. Furthermore, each slot may have a raised border that is engaged with a corresponding output drive 2130, where the raised border may be ramped or sloped from one end of the slot to the other for selectively permitting extension and retraction of the couplers 2130 in the sterile adapter. For example, in a "couplers retracted" position shown in FIG. 23A, the couplers 2130 may be engaged with a highest point of the raised slot border, which forces the couplers 2130 to withdraw toward the tool driver-side of the sterile barrier (and away from the tool driver). For example, as shown in FIG. 23A, the retracted couplers 2130 may be substantially flush with a tool-side of the sterile adapter 2100. In a "couplers extended" position shown in FIG. 23B, the couplers 2130 may be engaged with a lowest point of the raised slot border, which permits the couplers 2130 (which may be urged outward due to spring-loading and/or magnets, etc.) to extend outward beyond the tool-side of the sterile adapter.

Similar to at least some of the above-described variations, the shifting of the plate 2120 between the "couplers retracted" and "couplers extended" positions may be triggered by engagement and/or disengagement of the surgical tool 2150 from the sterile adapter 2100. For example, as shown in FIG. 23C, the surgical tool 2150 may include a tool plate 2160 configured to shift up and down on a sterile adapter-facing side of the tool. The tool plate 2160 may include a slot around each input drive 2152 so as to enable shifting of the tool plate 2160 without interfering with the input drives 2152. The shifting of the tool plate 2160 may be controlled, for example, via a connection within the tool to the movable side grips 2162, which may be configured to be held and actuated by a user. For example, the side grips 2162 may slide within a groove in the surgical tool 2150, and may include frictional features such as a textured surface (e.g., ribs or fingerhold contours) and/or a high friction material (e.g., silicone). Additionally or alternatively, the shifting of the tool plate 2160 may be controlled by a latch, lever, button, turn wheel, or any suitable mechanism.

The tool plate 2160 may further include shifting plate actuating features 2163 (e.g., a cutout in longitudinal ribs). Furthermore, as shown in FIG. 23B, the shifting plate 2120 may include one or more extensions 2122 that extend through openings of the sterile adapter plate 2100 to a tool-side of the sterile adapter plate 2100. The process of attaching the surgical tool 2150 to the sterile adapter 2100 may cause the tool plate 2160 to shift downward. When the tool plate 2160 is shifted downward from the position shown in FIG. 23C, the shifting plate actuating features 2163 may engage the extensions 2122 and cause the shifting plate 2120 to transition from the "couplers retracted" position shown in FIGS. 23A and 23B to the "couplers extended" position shown in FIGS. 24A and 24B. In some variations, the tool plate 2160 may include one or more springs 2164 or other suitable biasing features (e.g., leaf spring) that are configured to bias the tool 2150 toward engagement with the sterile adapter. When the coupler discs 2130 are extended in this manner, they may be configured to rotationally align with and engage the input drives 2152 of the surgical drive.

To decouple the surgical tool 2150 from the sterile adapter 2100, a reverse process may be followed. For example, the side grips 2162 of the tool 2150 may be actuated upward, thereby causing the tool plate 2160 to shift upwards. When the tool plate 2160 is shifted upward from the position shown in FIG. 24C, the shifting plate actuating features 2163 may engage the extensions 2122 and overcome the biasing force provided by springs 2164 in order to cause the shifting plate 2120 to transition from the "couplers extended" positions shown in FIGS. 24A and 2B to the "couplers retracted" position shown in FIGS. 23A and 23B. When the coupler discs 2130 are retracted in this manner, they are disengaged from the input drives 2152 of the surgical tool, thereby permitting decoupling of the surgical tool 2150 from the sterile adapter 2100.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated. It is intended that the following claims and their equivalents define the scope of the invention.

The invention claimed is:

1. A sterile adapter for use in a robotic surgical system, the sterile adapter comprising:
   a frame;
   a plate assembly coupled to the frame; and
   at least one rotatable coupler supported by the plate assembly and configured to rotate relative to the plate assembly and the frame, and to communicate torque from an output drive of a tool driver to an input drive of a surgical tool;
   wherein the rotatable coupler comprises a tool driver side having a first face comprising a first engagement feature configured to engage the output drive of the tool driver, and wherein the coupler further comprises a tool side having a second face comprising a second engagement feature configured to engage the input drive of the surgical tool.

2. The sterile adapter of claim 1, wherein the first and second engagement features comprise a different shape, and at least one of the first or second engagement features comprises an arcuate channel.

3. The sterile adapter of claim 1, wherein the first and second engagement features comprise a different shape, and at least one of the first or second engagement features comprises an arcuate ridge.

4. The sterile adapter of claim 1, wherein the first and second engagement features extend in opposite axial directions.

5. The sterile adapter of claim 4, wherein the first engagement feature comprises an arcuate recess and the second engagement feature comprises a recess substantially centered on an axis of rotation of the rotatable coupler.

6. The sterile adapter of claim 1, wherein the rotatable coupler comprises an outer flange.

7. The sterile adapter of claim 6, wherein the plate assembly includes a first plate and a second plate, and the outer flange of the rotatable coupler is disposed between the first plate and the second plate.

8. The sterile adapter of claim 1, wherein the first face of the rotatable coupler comprises a plurality of first drive features configured to engage driving features of the output drive of the tool driver, and wherein the second face of the rotatable coupler comprises a plurality of second drive features configured to engage driven features of the input drive of the surgical tool.

9. The sterile adapter of claim 8, wherein the plurality of first drive features and the plurality of second drive features are equidistant from an axis of rotation.

10. The sterile adapter of claim 9, wherein the plurality of first drive features and the plurality of second drive features are rotationally offset from each other.

11. The sterile adapter of claim 10, wherein the plurality of first drive features and the plurality of second drive features are rotationally offset from each other by about 90 degrees.

12. The sterile adapter of claim 1, wherein the frame defines a generally planar opening and the plate assembly is movable within the opening.

13. The sterile adapter of claim 1, wherein the frame is configured to couple to a sterile drape.

14. A drive coupler for communicating torque from a tool driver to a surgical tool, the drive coupler comprising:
   a body configured to be interposed between an output drive of the tool driver and an input drive of the surgical tool, wherein the body comprises:
      a first face defining a first recess and a first set of pin holes for engaging with the output drive of the tool driver; and
      a second face defining a second recess and a second set of pin holes for engaging with the input drive of the surgical tool.

15. The drive coupler of claim 14, wherein the first and second recesses are different in shape and extend in opposite axial directions.

16. The drive coupler of claim 14, wherein the first recess comprises an arcuate channel and the second recess is substantially centered on an axis of rotation of the rotatable coupler.

17. The drive coupler of claim 14, wherein the body comprises an outer flange.

18. The drive coupler of claim 14, wherein the first set of pin holes and the second set of pin holes are equidistant from an axis of rotation.

19. The drive coupler of claim 18, wherein the first set of pin holes and the second set of pin holes are rotationally offset from each other.

20. The drive coupler of claim 19, wherein the first set of pin holes and the second set of pin holes are rotationally offset from each other by about 90 degrees.

* * * * *